(12) United States Patent
Errico et al.

(10) Patent No.: US 7,223,291 B2
(45) Date of Patent: May 29, 2007

(54) INTERVERTEBRAL SPACER DEVICE HAVING ENGAGEMENT HOLE PAIRS FOR MANIPULATION USING A SURGICAL TOOL

(75) Inventors: Joseph P. Errico, Green Brook, NJ (US); Michael W. Dudasik, Nutley, NJ (US); Rafail Zubok, Midland Park, NJ (US)

(73) Assignee: SpineCore, Inc., Summit, NJ (US)

( * ) Notice: Subject to any disclaimer, the term of this patent is extended or adjusted under 35 U.S.C. 154(b) by 423 days.

(21) Appl. No.: 10/663,492

(22) Filed: Sep. 16, 2003

(65) Prior Publication Data

US 2004/0158325 A1 Aug. 12, 2004

Related U.S. Application Data

(63) Continuation-in-part of application No. 10/282,356, filed on Oct. 29, 2002, now Pat. No. 7,169,182, and a continuation-in-part of application No. 10/309,585, filed on Dec. 4, 2002, now Pat. No. 7,115,132, and a continuation-in-part of application No. 10/425,267, filed on Apr. 29, 2003, said application No. 10/282, 356 and a continuation-in-part of application No. 10/256,160, filed on Sep. 26, 2002, now Pat. No. 6,989,032, is a continuation-in-part of application No. 10/175,417, filed on Jun. 19, 2002, which is a continuation-in-part of application No. 10/151,280, filed on May 20, 2002, which is a continuation-in-part of application No. 09/970,479, filed on Oct. 4, 2001, now Pat. No. 6,669,730, and a continuation-in-part of application No. 10/140,153, filed on May 7, 2002, now abandoned, said application No. 09/970,479 is a continuation-in-part of application No. 09/968,046, filed on Oct. 1, 2001, now abandoned, said application No. 10/140,153 is a continuation-in-part of application No. 09/970,479, filed on Oct. 4, 2001, now Pat. No. 6,669,730, which is a continuation-in-part of application No. 10/128,619, filed on Apr. 23, 2002, now Pat. No. 6,863,689, which is a continuation-in-part of application No. 09/906,119, filed on Jul. 16, 2001, now Pat. No. 6,607,559, and a continuation-in-part of application No. 09/982,148, filed on Oct. 18, 2001, now Pat. No. 6,673,113.

(51) Int. Cl.
 *A61B 17/56* (2006.01)
(52) U.S. Cl. ............................ 623/17.15; 623/17.14; 606/99
(58) Field of Classification Search .................. 606/61, 606/99, 53, 205, 207; 623/17.11, 17.13, 623/17.16, 17.14, 17.15
See application file for complete search history.

(56) References Cited

U.S. PATENT DOCUMENTS 3,867,728 A 2/1975 Stubstad et al.

(Continued)

*Primary Examiner*—Brian E. Pellegrino
(74) *Attorney, Agent, or Firm*—Lerner, David, Littenberg, Krumholz & Mentlik, LLP

(57) ABSTRACT

Instrumentation for implanting an artificial intervertebral disc includes static trials and a dynamic trial for determining the appropriate size of disc to be implanted, static trial holders for manipulating the static trials, inserter/impactors for inserting and removing the static trials and for inserting the artificial intervertebral discs, repositioners/extractors for repositioning and extracting the static trials or the artificial intervertebral discs, and a leveler for setting the proper position of the artificial intervertebral disc. Methods for using the same are also disclosed. Features for artificial intervertebral discs and intervertebral spacer devices useful for manipulation by the instrumentation are also disclosed.

20 Claims, 27 Drawing Sheets

U.S. PATENT DOCUMENTS

| | | |
|---|---|---|
| 4,309,777 A | 1/1982 | Patil |
| 4,605,417 A | 8/1986 | Fleischauer |
| 4,759,766 A | 7/1988 | Buettner-Janz et al. |
| 4,759,769 A | 7/1988 | Hedman et al. |
| 4,932,969 A | 6/1990 | Frey et al. |
| 4,997,432 A | 3/1991 | Keller |
| 5,236,460 A | 8/1993 | Barber |
| 5,314,477 A | 5/1994 | Marnay |
| 5,370,697 A | 12/1994 | Baumgartner |
| 5,401,269 A | 3/1995 | Buttner-Janz et al. |
| 5,425,773 A | 6/1995 | Boyd et al. |
| 5,507,816 A | 4/1996 | Bullivant |
| 5,556,431 A | 9/1996 | Buttner-Janz |
| 5,562,738 A | 10/1996 | Boyd et al. |
| 5,676,701 A | 10/1997 | Yuan et al. |
| 5,683,465 A | 11/1997 | Shinn et al. |
| 5,782,832 A | 7/1998 | Larsen et al. |
| 5,893,889 A | 4/1999 | Harrington |
| 5,895,428 A | 4/1999 | Berry |
| 5,899,941 A | 5/1999 | Nishijima et al. |
| 5,989,291 A | 11/1999 | Ralph et al. |
| 6,039,763 A | 3/2000 | Shelokov |
| 6,190,414 B1 * | 2/2001 | Young et al. ............ 623/17.15 |
| 6,368,350 B1 | 4/2002 | Erickson et al. |
| 6,375,682 B1 | 4/2002 | Fleischmann et al. |
| 6,517,580 B1 | 2/2003 | Ramadan et al. |
| 6,582,468 B1 | 6/2003 | Gauchet |
| 6,610,092 B2 | 8/2003 | Ralph et al. |
| 6,641,614 B1 * | 11/2003 | Wagner et al. ............ 623/17.15 |
| 6,645,249 B2 | 11/2003 | Ralph et al. |
| 6,673,113 B2 | 1/2004 | Ralph et al. |
| 6,682,562 B2 | 1/2004 | Viart et al. |
| 6,706,068 B2 | 3/2004 | Ferree |
| 2001/0016773 A1 | 8/2001 | Serhan et al. |
| 2002/0111681 A1 | 8/2002 | Ralph et al. |
| 2003/0014110 A1 | 1/2003 | Ralph et al. |
| 2003/0014112 A1 | 1/2003 | Ralph et al. |
| 2003/0028249 A1 | 2/2003 | Baccelli et al. |
| 2003/0055503 A1 | 3/2003 | O'Neil |
| 2003/0060886 A1 | 3/2003 | Van Hoeck et al. |
| 2003/0069586 A1 | 4/2003 | Errico et al. |
| 2003/0069642 A1 | 4/2003 | Ralph et al. |
| 2003/0074067 A1 | 4/2003 | Errico et al. |
| 2003/0149482 A1 | 8/2003 | Michelson |
| 2003/0204260 A1 | 10/2003 | Ferree |
| 2003/0208271 A1 | 11/2003 | Kuras |
| 2003/0233097 A1 | 12/2003 | Ferree |
| 2003/0233148 A1 | 12/2003 | Ferree |
| 2004/0002759 A1 | 1/2004 | Ferree |
| 2004/0002762 A1 | 1/2004 | Hawkins |
| 2004/0010316 A1 | 1/2004 | William et al. |
| 2004/0030389 A1 | 2/2004 | Ferree |
| 2004/0030390 A1 | 2/2004 | Ferree |
| 2004/0034426 A1 | 2/2004 | Errico et al. |

* cited by examiner (Section A-A of Fig. 1)

(Section B-B of Fig. 1)

(Section A-A of Fig. 7)

(Section B-B of Fig. 7)

(Section C-C on Fig.15)

(Perspective of Fig.14)

(Section A-A on Fig. 13)

(Section B-B on Fig. 13)

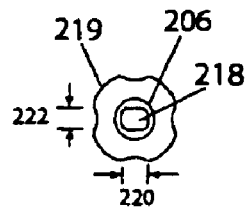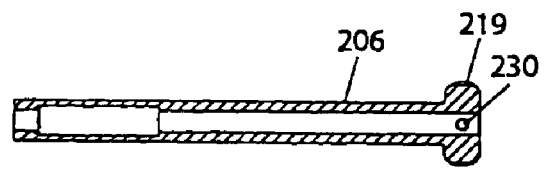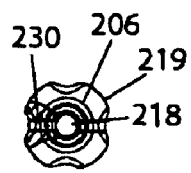
Fig. 25     Fig. 24     Fig. 26
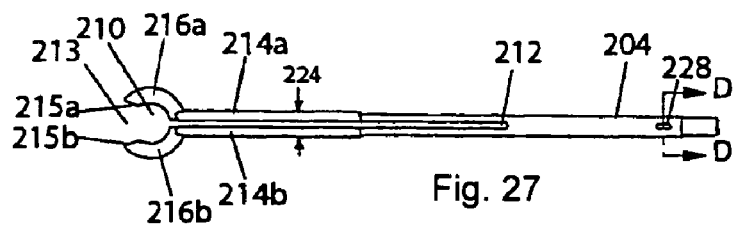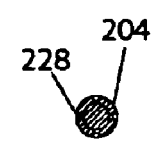
Fig. 27     Fig. 28
(D-D of Fig.27)
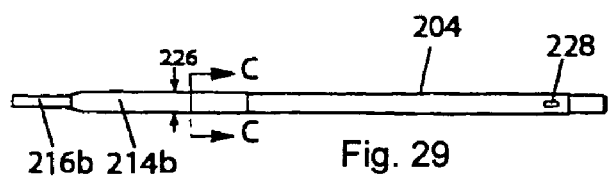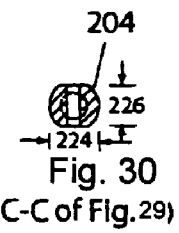
Fig. 29     Fig. 30
(C-C of Fig.29)
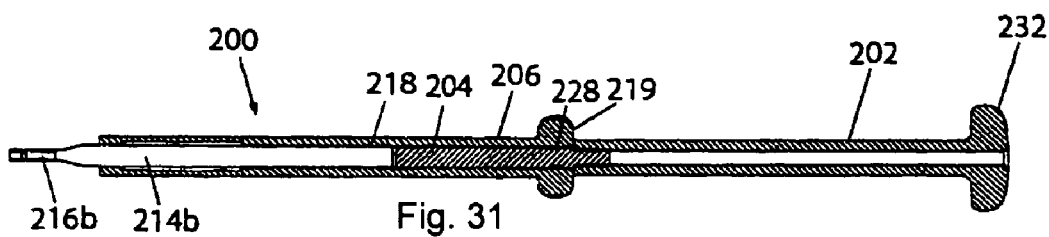
Fig. 31
(Section A-A of Fig.22)

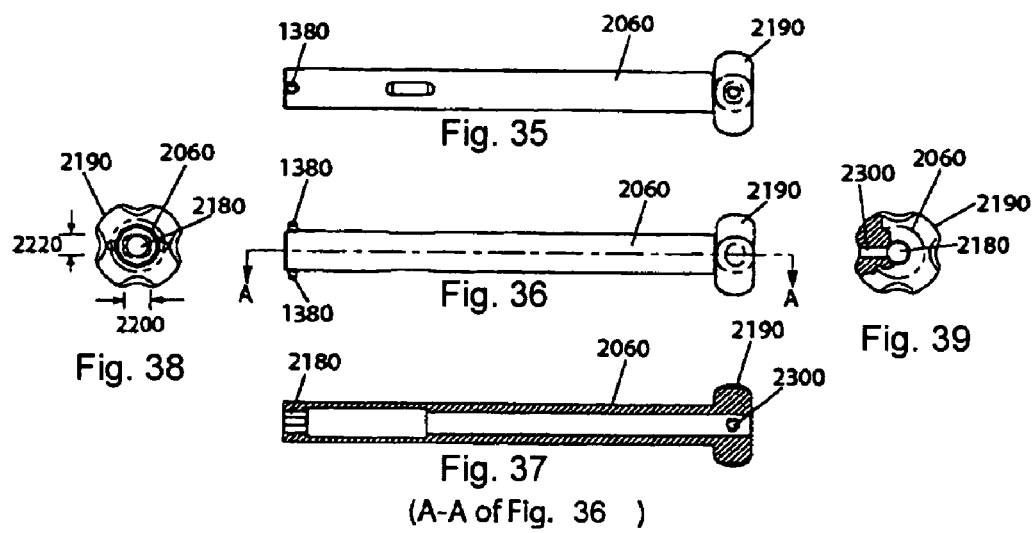
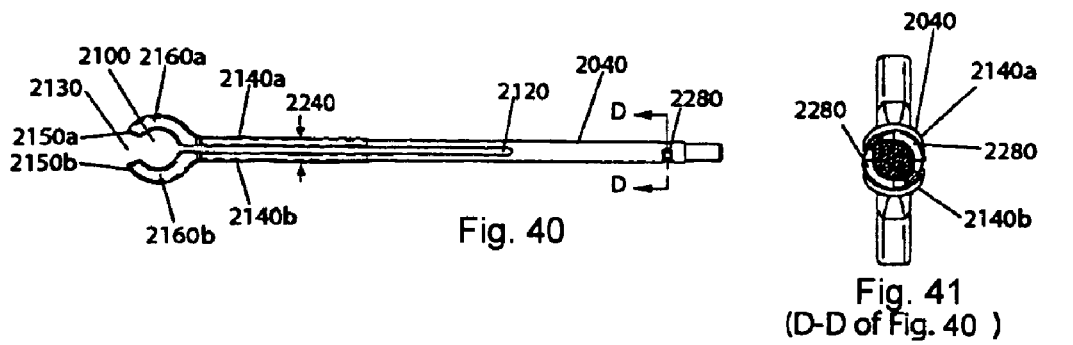
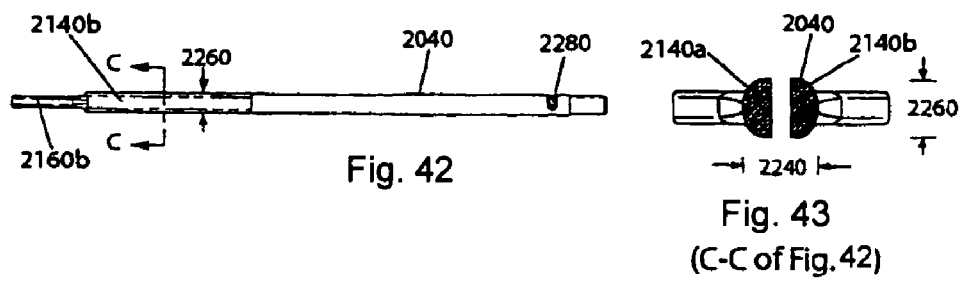
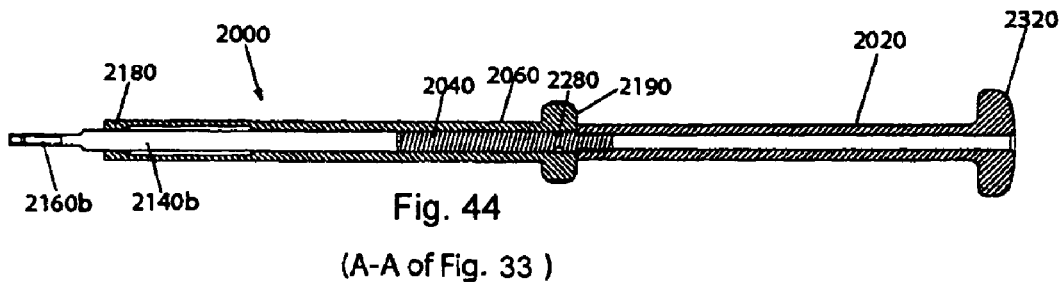

(Section A-A of Fig. 52)

(Section A-A of Fig. 56)

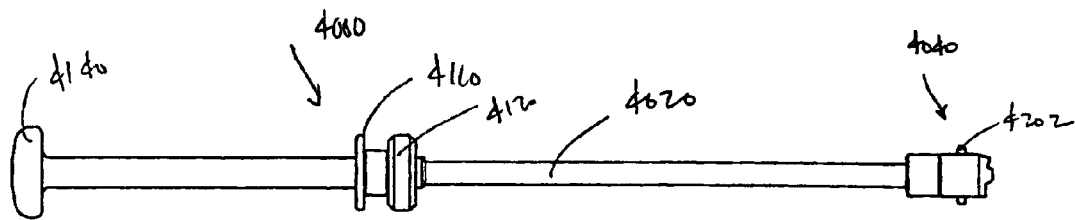
Fig. 71
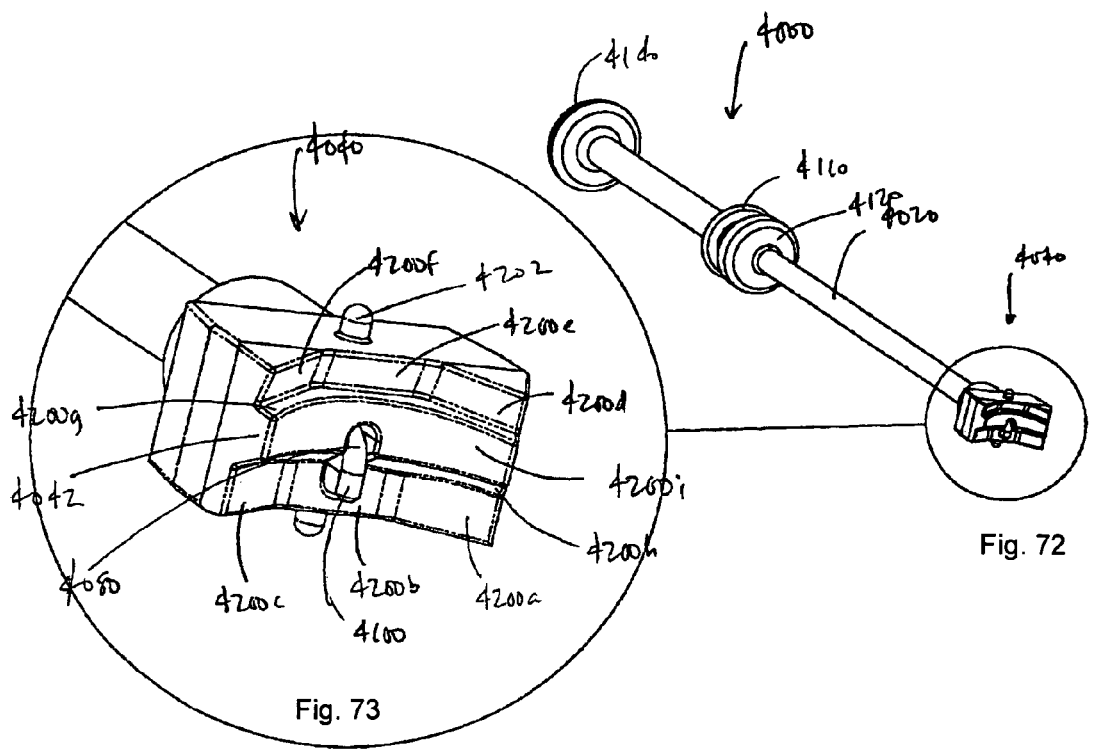
Fig. 72
Fig. 73

INTERVERTEBRAL SPACER DEVICE HAVING ENGAGEMENT HOLE PAIRS FOR MANIPULATION USING A SURGICAL TOOL

CROSS-REFERENCE TO RELATED APPLICATIONS

The present application is a continuation-in-part application of U.S. patent application Ser. No. ("USPASN") 10/282,356 (filed Oct. 29, 2002) entitled "Instrumentation and Methods for use in Implanting an Artificial Intervertebral Disc" ("the '356 application") and a continuation application of U.S. patent application Ser. No. 10/309,585 (filed Dec. 4, 2002) now U.S. Pat. No. 7,115,132 entitled "Static Trials and Related Instruments and Methods for use in Implanting an Artificial Intervertebral Disc" ("the '585 application") and a continuation-in-part application of U.S. patent application Ser. No. 10/425,267 (filed Apr. 29, 2003) entitled "Wedge Plate Inserter/Impactor and Related Methods for use in Implanting an Artificial Intervertebral Disc" ("the '267 application"), the '585 application and the '267 application are continuation-in-part applications of the '356 application, which is a continuation-in-part application of U.S. patent application Ser. No. 10/256,160 (filed Sep. 26, 2002) now U.S. Pat. 6,989,032 entitled "Artificial Intervertebral Disc Having Limited Rotation Using a Captured Ball and Socket Joint With a Solid Ball and Compression Locking Post" ("the '160 application"), which is a continuation-in-part application of U.S. patent application Ser. No. 10/175,417 (filed Jun. 19, 2002) entitled "Artificial Intervertebral Disc Utilizing a Ball Joint Coupling", which is a continuation-in-part application of U.S. patent application Ser. No. 10/151,280 (filed May 20, 2002) entitled "Tension Bearing Artificial Disc Providing a Centroid of Motion Centrally Located Within an Intervertebral Space", which is a continuation-in-part application of both U.S. patent application Ser. No. 09/970,479 (filed Oct. 4, 2001) now U.S. Pat. No. 6,669,730 entitled "Intervertebral Spacer Device Utilizing a Spirally Slotted Belleville Washer Having Radially Extending Grooves" as well as U.S. patent application Ser. No. 10/140,153 (filed May 7, 2002 now abandoned) entitled "Artificial Intervertebral Disc Having a Flexible Wire Mesh Vertebral Body Contact Element", the former being a continuation-in-part application of U.S. patent application Ser. No. 09/968,046 (filed Oct. 1, 2001) now abandoned entitled "Intervertebral Spacer Device Utilizing a Belleville Washer Having Radially Extending Grooves" and the latter being a continuation-in-part application of both U.S. patent application Ser. No. 09/970,479 (detailed above) as well as U.S. patent application Ser. No. 10/128,619 (filed Apr. 23, 2002) now U.S. Pat. No. 6,863,689 entitled "Intervertebral Spacer Having a Flexible Wire Mesh Vertebral Body Contact Element", which is a continuation-in-part application of both U.S. patent application Ser. No. 09/906,119 (filed Jul. 16, 2001) now U.S. Pat. No. 6,607,559 and entitled "Trial Intervertebral Distraction Spacers" as well as U.S. patent application Ser. No. 09/982,148 (filed Oct. 18, 2001) now U.S. Pat. No. 6,673,113 and entitled "Intervertebral Spacer Device Having Arch Shaped Spring Elements". All of the above mentioned applications are hereby incorporated by reference herein in their respective entireties.

FIELD OF THE INVENTION

This invention relates generally to systems and methods for use in spine arthroplasty, and more specifically to instruments for distracting an intervertebral space, inserting and removing trial artificial intervertebral discs, and inserting, impacting, repositioning, leveling and extracting artificial intervertebral discs, and methods of use thereof, and also more specifically to intervertebral spacer devices and artificial intervertebral discs having features rendering them suitable for manipulation thereby.

BACKGROUND OF THE INVENTION

The bones and connective tissue of an adult human spinal column consists of more than twenty discrete bones coupled sequentially to one another by a tri-joint complex that consists of an anterior disc and the two posterior facet joints, the anterior discs of adjacent bones being cushioned by cartilage spacers referred to as intervertebral discs. These more than twenty bones are anatomically categorized as being members of one of four classifications: cervical, thoracic, lumbar, or sacral. The cervical portion of the spine, which comprises the top of the spine, up to the base of the skull, includes the first seven vertebrae. The intermediate twelve bones are the thoracic vertebrae, and connect to the lower spine comprising the five lumbar vertebrae. The base of the spine is the sacral bones (including the coccyx). The component bones of the cervical spine are generally smaller than those of the thoracic spine, which are in turn smaller than those of the lumbar region. The sacral region connects laterally to the pelvis. While the sacral region is an integral part of the spine, for the purposes of fusion surgeries and for this disclosure, the word spine shall refer only to the cervical, thoracic, and lumbar regions.

The spinal column is highly complex in that it includes these more than twenty bones coupled to one another, housing and protecting critical elements of the nervous system having innumerable peripheral nerves and circulatory bodies in close proximity. In spite of these complications, the spine is a highly flexible structure, capable of a high degree of curvature and twist in nearly every direction.

Genetic or developmental irregularities, trauma, chronic stress, tumors, and degenerative wear are a few of the causes that can result in spinal pathologies for which surgical intervention may be necessary. With respect to the failure of the intervertebral disc, and the insertion of implants and/or height restorative devices, several methods and devices have been disclosed in the prior art that achieve immobilization and/or fusion of adjacent bones by implanting artificial assemblies in or on the spinal column. More recently, the development of non-fusion implant devices, which purport to permit continued natural movement in the tri-joint complex, have provided great promise as a preferably alternative to fusion devices. The region of the back that needs to be corrected, as well as the individual variations in anatomy, determine the appropriate surgical protocol and implantation assembly. Generally, the preparation of the intervertebral space for the receipt of fusion or non-fusion devices involves removing the damaged disc material and thereafter distracting the adjacent vertebral bones to their appropriate distance apart. Once the proper height of the intervertebral space is restored, the fusion or non-fusion device can be implanted.

It is an object of the invention to provide artificial intervertebral disc and intervertebral spacer device features, as well as instrumentation and methods, that enable surgeons to more accurately, easily, and efficiently prepare the intervertebral space and implant fusion or non-fusion devices. Other objects of the invention not explicitly stated will be set forth and will be more clearly understood in conjunction with the descriptions of the preferred embodiments disclosed hereafter.

SUMMARY OF THE INVENTION

The preceding objects are achieved by the invention, which includes artificial intervertebral disc and intervertebral spacer device features suitable for manipulation thereof by surgical instrumentation, and further includes static trial artificial intervertebral discs (sometimes referred to herein as a "static trial"), static trial artificial intervertebral disc holders (sometimes referred to herein as "static trial holders"), a dynamic trial artificial intervertebral disc (sometimes referred to herein as a "dynamic trial"), artificial intervertebral disc inserter/impactors (sometimes referred to herein as "inserter/impactors"), an artificial intervertebral disc repositioner/extractor (sometimes referred to herein as a "repositioner/extractor"), and an artificial intervertebral disc leveler (sometimes referred to herein as a "leveler").

More particularly, the features, systems, and methods disclosed herein are intended for use in spine arthroplasty procedures, and specifically for use with the features, systems, and methods described herein in conjunction with the features, systems, and methods described in the '356, '585, '267, '160, and '528 applications, as well as those described in U.S. patent application Ser. No. 09/906,127 (filed Jul. 16, 2001) entitled "Insertion Tool For Use With Intervertebral Spacers" ("the '127 application"), which is hereby incorporated by reference herein. However, it should be understood that the features, systems, and methods described herein are also suitable for use with other features, systems, and methods without departing from the scope of the invention.

For example, while the static trials described herein are primarily intended for use in determining the appropriate size of particular embodiments of the artificial intervertebral disc implants described in the '160 and '528 applications to be implanted (or whether a particular size can be implanted) into the distracted intervertebral space, they can also be used for determining the appropriate size of any other suitably configured orthopedic implant or trial to be implanted (or whether a particular size can be implanted) into the distracted intervertebral space. They can also be used to distract an intervertebral space (e.g., in the same manner in which the trial spacers in the '127 application are used as described in the '127 application).

And, for example, while the static trial holders described herein are primarily intended for use in holding, inserting, removing, and otherwise manipulating the static trials described herein, they can also be used for manipulating any embodiment of the trial spacers described in the '127 application (also referred to therein and herein as distraction spacers), and can also be used for manipulating any other suitably configured orthopedic device.

And, for example, while the dynamic trial described herein is primarily intended for use in distracting an intervertebral space according to the procedures described herein and/or for determining the appropriate size of particular embodiments artificial intervertebral disc implants described in the '160 and '528 applications to be implanted (or whether a particular size can be implanted) into the distracted intervertebral space, it can also be used for distracting an intervertebral space according to other procedures and/or for determining the appropriate size of any other suitably configured orthopedic implant or trial to be implanted (or whether a particular size can be implanted) into the distracted intervertebral space.

And, for example, while the inserter/impactors described herein are primarily intended for use in holding, inserting, removing, impacting, extracting, and otherwise manipulating particular embodiments of the artificial intervertebral disc implants described in the '160 and '528 applications, they can also be used for manipulating any other suitably configured orthopedic implant or trial.

And, for example, while the repositioners/extractors described herein are primarily intended for use in repositioning and/or extracting and/or otherwise manipulating particular embodiments of the artificial intervertebral disc implants described in the '160 and '528 applications, they can also be used for manipulating any other suitably configured orthopedic implant or trial.

And, for example, while the leveler described herein is primarily intended for use in setting the proper position of, and/or otherwise manipulating, particular embodiments of the artificial intervertebral disc implants described in the '160 and '528 applications, it can also be used for manipulating any other suitably configured orthopedic implant or trial.

While the instrumentation described herein (e.g., the static trials, static trial holders, dynamic trial, inserter/impactors, repositioners/extractors, and leveler) will be discussed for use with the artificial intervertebral disc of FIGS. 13-20, such discussions are merely by way of example and not intended to be limiting of their uses. Thus, it should be understood that the tools can be used with any of the artificial intervertebral discs disclosed in the '160 and '528 applications, or any other artificial intervertebral disc having (or being modifiable or modified to have) suitable features therefor. Moreover, it is anticipated that the features of the artificial intervertebral disc (e.g., the angled flat surfaces and accompanying holes and inwardly facing baseplate surfaces) and/or the static trials (e.g., the cylindrical trunks and angled flat surfaces and opposing notches and accompanying holes) that are used by the tools discussed herein to hold and/or manipulate these devices (such features, it should be noted, were first shown and disclosed in the '356, '585, '267, '160, and/or '528 applications) can be applied, individually or collectively or in various combinations, to other trials, spacers, artificial intervertebral discs or other orthopedic devices as stand-alone innovative features for enabling such trials, spacers, artificial intervertebral discs, or other orthopedic devices to be more efficiently and more effectively held and/or manipulated by the tools described herein or by other tools having suitable features. In addition, it should be understood that the invention encompasses artificial intervertebral discs, spacers, trials (static or dynamic), and/or other orthopedic devices, that have one or more of the features disclosed herein, in any combination, and that the invention is therefore not limited to artificial intervertebral discs, spacers, trials, and/or other orthopedic devices having all of the features simultaneously.

More particularly with regard to the static trials described herein, a plurality of static trials are provided primarily for use in determining the appropriate size of an artificial intervertebral disc to be implanted (or whether a particular size of the artificial intervertebral disc can be implanted) into the distracted intervertebral space (e.g., the artificial intervertebral disc 160 of FIGS. 13-20). Preferably, for each artificial intervertebral disc to be implanted, a plurality of sizes of the artificial intervertebral disc would be available. That is, preferably, a plurality of the same type of artificial intervertebral disc would be available, each of the plurality having a respective width and depth dimension combination that allows it to fit within a correspondingly dimensioned intervertebral space. For example, the plurality of artificial intervertebral discs could include artificial intervertebral discs having widths being either 35 mm or 40 mm, and depths ranging from 14 mm to 18 mm in 1 mm increments, for a total of 10 discs. Accordingly, preferably, each of the plurality of static trials for use with a particular plurality of differently sized artificial intervertebral discs would have a respective width and depth dimension set corresponding to the width and depth of a respective one of the plurality of differently sized artificial intervertebral discs. For example, the plurality of static trials for use with the set of artificial intervertebral discs described for example could include static trials having widths being either 35 mm or 40 mm, and depths ranging from 14 mm to 18 mm in 1 mm increments, for a total of 10 static trials. It should be understood that the artificial intervertebral discs and/or the static trials can be offered in a variety of dimensions without departing from the scope of the invention, and that the dimensions specifically identified and quantified herein are merely exemplary. Moreover, it should be understood that the set of static trials need not include the same number of trials for each artificial intervertebral disc in the set of artificial intervertebral discs, but rather, none, one, or more than one trial can be included in the trial set for any particular artificial intervertebral disc in the set.

Each of the plurality of static trials preferably further includes features that can be used by the static trial holders (described below), the inserter/impactors (described below), and the repositioners/extractors (described below). With regard to a feature that can be used by the static trial holder, each static trial preferably includes a recess that can be engaged by the opposing semicircular extents of the static trial holder. Preferably, this recess forms a perimetrical groove (a groove that extends around at least a portion of the perimeter of the static trial, e.g., an annular groove) that establishes a trunk (e.g., a cylindrical trunk) between the baseplates of the static trial, such that the baseplates extend as flanges from either end of the trunk. Accordingly, preferably, the opposing semicircular extents each have a thickness smaller than the width of the annular groove, and as such fit into the annular groove to grip the cylindrical trunk between them.

Additional features that can be used by the static trial holders include (on any static trial surface that faces the desired engagement approach direction of the static trial holder, e.g., on each of the anteriorly facing and anteriorlaterally facing flat surfaces of the static trial as described below) opposing recesses, preferably formed as upper and lower notches, an upper notch in the upper baseplates and a lower notch in the lower baseplate. Preferably, the notches are sized so that the opposing notches of each pair form a volume that is dimensioned to closely accommodate the dimensions of the static trial holder's prongs' cross-section. That is, as described below, the body of each prong is thicker than the semicircular extent that extends from the body, and as such, whereas the semicircular extents fit into the annular groove, the prongs do not because their thickness is greater than the width of the annular groove opening. Each notch pair accommodates this greater thickness, and as such, as the opposing semicircular extents of the static trial holder are placed into the annular groove, the bodies of the prongs of the static trial holder pass into the notches so that the semicircular extents can continue into the annular groove and be seated around the cylindrical trunk. Once the prongs are fitted within the notch pair, interference between the prongs and the notch walls limits or prevents rotation of the static trial about a longitudinal axis (e.g., an axis parallel to the longitudinal axis of the cylindrical trunk) with respect to the static trial holder.

With regard to features that can be used by the inserter/impactors, each static trial (and each artificial intervertebral disc that the trials approximate) preferably includes an anteriorly facing flat surface, flanked by two anteriolaterally facing flat surfaces (one on each side of the anteriorly facing flat surface), and, to provide for holding of the static trial or disc for an anterior insertion approach, a hole spaced from the anteriorly facing flat surface, the hole having a longitudinal axis parallel to the anteriorly facing flat surface. The holding pin of the inserter/impactor fits within the hole, and the angled flat surfaces of the static trial or disc fit against the correspondingly angled flat surfaces of the inserter/impactor, and operation of the inserter/impactor pulls the holding pin toward the flat surface of the inserter/impactor opposite the pin, to rigidly hold the static trial or disc by the baseplate.

In some embodiments of the inserter/impactor having a wedge plate, the holding pin protrudes from a wedge-shaped extended surface of the distal end of the inserter/impactor and is restricted from upward movement with respect to the distal head by the presence of the wedge-shaped extended surface of the distal end of the inserter/impactor. More particularly, with any attempted upward movement of the holding pin, the pin encounters the upper surface of the channel in which the pin travels, preventing any such upward movement.) When the static trial or artificial disc is held in this manner, rotation of the static trial or disc about a longitudinal axis (e.g., in the case of the trials, an axis parallel to the longitudinal axis of the cylindrical trunk) relative to the inserter/impactor is prevented by interference of the corners of the static trial's or disc's flat surfaces and the corners of the inserter/impactor's flat surfaces, similar to the manner in which a wrench holding a nut prevents rotation of the nut relative to the wrench. Further, the holding of the static trial or disc in this manner allows for some repositioning of the static trial or disc in the intervertebral space via rotation of the static trial or disc in either direction about the longitudinal axis of the intervertebral space.

Further, in some embodiments of the inserter/impactor having a wedge plate, when the trial or disc is held in this manner, rotation of the trial or disc about a lateral axis of the trial or disc relative to the inserter/impactor is prevented by interference of the inwardly facing surface of the first baseplate (e.g., upper baseplate) of the trial or disc and the corresponding surface (e.g., upper surface) of the wedge on the distal end, and by interference of the inwardly facing surface of the second baseplate (e.g., lower baseplate) of the trial or disc and the corresponding surface (e.g., lower surface) of the wedge on the distal end. With regard to artificial discs, it is preferable that the wedge on the inserter/impactor will interfere between the first and second baseplates (e.g., upper and lower) so that the surfaces of the first and second baseplates align at a preferred 15 degrees angle of lordosis when the disc is held by the inserter/impactor.

Preferably, both of the baseplates of the static trial or disc have similarly configured flat surfaces, and both baseplates' flat surfaces fit against the angled flat surfaces of the inserter/impactor to provide for a more secure holding of the static trial or disc by the inserter/impactor. Also preferably, in order to provide for a holding of the static trial or disc for two additional (here, anteriolateral) insertion approaches, each static trial or disc also includes two additional holes, one spaced apart from one of the anteriolaterally facing flat surfaces, and the other spaced apart from the other of the anteriolaterally facing flat surfaces. Accordingly, operation of the inserter/impactor can fit the holding pin into either of these two additional holes, and hold the anteriolaterally facing flat surface (the one associated with the hole into which the pin is fit) of the static trial or disc against the flat surface of the inserter/impactor opposite the pin. It should be understood that preferably, in order to facilitate these two additional approaches, the angle separating the anteriorly facing flat surface of the static trial or disc and one of the anteriolaterally facing flat surfaces of the static trial or disc is equal to the angle separating the anteriorly facing flat surface and the other of the anteriolaterally facing flat surfaces.

With regard to features that can be used by the repositioners/extractors, each static trial (and each artificial intervertebral disc that the trials approximate) preferably includes at least two holes extending longitudinally into one of the baseplates of the trial or disc from the inwardly facing surface of the base plate. More than two holes can be used to provide for multiple repositioning/extracting approaches. Preferably, in order for the same repositioning/extracting tool to be used for multiple approaches on the same trial or artificial intervertebral disc, adjacent holes should be separated by the same distance separating other adjacent holes.

As discussed in greater detail below with regard to the repositioners/extractors, in order to engage two of the holes, each repositioner/extractor has two pins extending in parallel from a central shaft, perpendicular to the longitudinal axis of the central shaft. The pins can be inserted into the holes, and pulling or pushing on the central shaft along its longitudinal axis when the holes are engaged pulls or pushes the static trial or artificial intervertebral disc in the intervertebral space. Further, because two holes are engaged, the static trial or artificial intervertebral disc can be rotated in either direction about a longitudinal axis passing through the intervertebral space, by rotating of the central shaft of the repositioner/extractor about its distal end, about an axis parallel to the longitudinal axes of the pins.

On each repositioner/extractor, the pins are formed on prongs that extend laterally from the central shaft. The direction of the prongs, and the location of the pins relative to the central shaft, determine the angle or angles of surgical approach for which a particular repositioner/extractor can be used. Further, the number and location of holes further determine the angle or angles of surgical approach for which a particular repositioner/extractor can be used. Accordingly, the present invention contemplates a variety of repositioner/extractors, and a variety of holes configurations, to provide the surgeon with a variety of possible surgical approach angles.

As described in greater detail below, three repositioner/extractors are illustrated and described (symmetric, offset left, and offset right) for example, and, for example, two hole configurations are illustrated and described. A first hole configuration includes the hole configuration described above, that is, three holes on one of the baseplates (e.g., the lower baseplate), the holes being configured so that a first hole is located in the anterior-posterior plane, and the adjacent (second and third) holes are located in respective opposing anteriolateral planes on either side of the first hole. A second hole configuration includes four holes on one of the baseplates (e.g., the upper baseplate), the holes being configured so that first and second holes straddle the anterior-posterior plane, a third hole is located so that the third hole and the first hole straddle one of the opposing anteriolateral planes, and a fourth hole is located so that the fourth hole and the second hole straddle the other of the opposing anteriolateral planes.

With regard to the static trial holders described herein, the static trial holders are provided primarily for use in holding, inserting, removing, and otherwise manipulating the static trials described herein. Preferably, the static trial holder has (in some embodiments, at an end of an extension of the static trial holder) a pair of opposing prongs that open away from one another and close toward one another. Each of the prongs has a semicircular extent and the semicircular extents face one another to define a circular holding enclosure that is useful for capturing the cylindrical trunk of the static trial between them. The prongs are spring biased toward a neutral position such that the holding enclosure is spring biased to a receptive state in which the cylindrical trunk can be snapped into (or out of the holding enclosure by temporarily placing the holding enclosure in an expanded state (by forcing the cylindrical trunk against the mouth of the enclosure) that allows passage of the cylindrical trunk through the mouth of the enclosure.

Once the cylindrical trunk is in the enclosure, the holding enclosure can be placed in a contracted state, or locked, where the trial is more securely held, so that the trial will not escape the holding enclosure as it is experiencing greater forces while being inserted and removed from the intervertebral space. This locking is effected by rotating a sleeve that surrounds the prongs. The bore of the sleeve is configured to press the prongs together when the sleeve is rotated a quarter turn (ninety degrees), and to allow them to separate when the sleeve is again (or in some embodiments, reverse) rotated a quarter turn (in either direction). (In some embodiments, either quarter turn is in either direction; e.g., in certain embodiments illustrated herein, the quarter turn that separates the prongs is a reverse rotation of the quarter turn that presses them together). In some embodiments, the sleeve is biased toward stopping its rotation at either the "locked" or "unlocked" states of the holding enclosure, by the cooperation of recesses on the extension's outer surface and corresponding spring plungers radially disposed to project from the sleeve's inner surface. In other embodiments, the sleeve stops its rotation at either the "locked" or "unlocked" states of the holding enclosure, due to radially inwardly directed screw heads on the sleeve's inner surface that ride in ninety-degree arc grooves on the extension's outer surface and that stop when the end of the groove is reached.

Further, the sleeve of the static trial holder preferably has on its exterior surface at least one stop protrusion that is positioned and dimensioned to extend dorsally or ventrally from the exterior surface when the holding enclosure is in its "locked" state, so that when the surgeon inserts the static trial into the intervertebral space, the stop protrusions prevent the static trial from being inserted too far into the space (that is, so that the stop protrusions hit against the lips of the adjacent vertebral body endplates before the static trial is inserted too far).

It should be understood that when a static trial is being held (either when the holding enclosure is in its receptive state or in its contracted state), because the semicylindrical extents fit within the annular groove of the static trial, the static trial will not escape from the enclosure along the longitudinal axis of the cylindrical trunk. While the static trial holders are discussed herein as primarily used for manipulating the static trials, they are preferably is also useful for manipulating the distraction spacers described in the '127 application, in that the semicircular extents of the pincers preferably also interact with the annular grooves and cylindrical trunks of those distraction spacers in the same manner as described herein.

With regard to the dynamic trial described herein, the dynamic trial is provided primarily for distracting an intervertebral space according to the procedures described herein and/or for determining the appropriate size of an artificial intervertebral disc to be implanted (or whether a particular size can be implanted) into the distracted intervertebral space. While the distraction systems and methods described in the '127 application are also useful for distracting an intervertebral space, the dynamic trial is provided as an additional or alternate distraction tool. Further, while the static trials described herein as useful for determining the appropriate size of an artificial intervertebral disc to be implanted (or whether a particular size can be implanted), the dynamic trial is provided as an additional or alternate sizing tool.

The dynamic trial preferably includes a shaft having a bifurcated trial at a distal end. Each half of the bifurcated trial preferably has on its outwardly facing surface a convex dome that is shaped like the convex dome of the corresponding baseplate of the artificial intervertebral disc that the dynamic trial approximates. The shaft includes an inner shaft portion that centrally divides into upper and lower distal extensions that, from the point of division to their distal ends, are each biased toward positions in which they converge toward one another. The lower distal extension is connected to the lower half of the bifurcated trial, and the upper distal extension is connected to the upper half of the bifurcated trial. Preferably, the upper half is adjustably connected to the upper distal extension by a pivot pin that allows the upper half to rotate about a lateral axis that passes through the longitudinal and lateral center of the bifurcated trial. This axis of rotation allows the upper half, when separating from the lower half, to adjust to the orientation of the upper vertebral bone without causing the bone to hinge relative to the lower vertebral bone. In order to effect the separation of the upper and lower halves, the shaft further includes an outer shaft potion that is translatable adjacent the inner shaft portion, the outer shaft portion having a pin that passes between the distal extensions.

The outer shaft portion is preferably translatable distally by the forward movement of a control knob near the proximal end of the shaft, and translatable proximally by backward movement of the control knob. As the outer shaft portion is pushed distally, the pin is pushed distally to overcome the bias of the divided extensions to separate them and correspondingly separate the halves of the bifurcated trial. Preferably, markings are provided on the inner shaft portion to quantify the depth (to which the bifurcated trial has been expanded) corresponding to the distance that the outer shaft portion has been translated with respect to the inner shaft portion. It is anticipated that the pushing force required to separate the halves will increase as they separate, due to the compression of the spine seeking to close the intervertebral space and the annulus seeking to prevent the adjacent vertebral discs from separating beyond a certain point. Therefore, to provide a mechanical advantage to the operator in the event that greater distraction is required, but the operator cannot push the control knob farther with unaided human effort, an fine control knob is provided. The fine control knob is preferably threaded onto the proximal end of the inner shaft portion, proximal to the control knob. Thus, rotation of the fine control knob about the longitudinal axis of the inner shaft portion will cause the body of the fine control knob to press against the control knob to move it farther distally. The interference of the threads of the fine control knob-inner shaft portion interface prevents the fine control knob from backing up proximally unless the fine control knob is reverse rotated to effect that result. Finally, the proximal end of the shaft is preferably flanged to serve as a slap hammer for impaction, if necessary for proper positioning of the bifurcated trial, and/or forced extraction of the bifurcated trial.

With further regard to the inserter/impactors described herein, the inserter/impactors are provided primarily for holding, inserting, repositioning, removing, impacting, extracting, and otherwise manipulating an artificial intervertebral disc (or static trial) having features suitable for being manipulated by the inserter/impactors. Exemplary suitable artificial intervertebral discs are described in the '160 and '528 applications with regard to FIGS. 8a-z, 9a-u, 10a-u, 11a-k, and 12a-p thereof and by the accompanying descriptions therefor (e.g., embodiments identified as the first, second, third, fourth, and fifth preferred embodiments of the fourth embodiment family, etc.). Regarding the features suitable for being manipulated by the inserter/impactors, such features include those discussed above as being suitable features on the static trials and artificial intervertebral disc, namely, an anteriorly facing flat surface on the second (e.g., lower) baseplate of the trial or disc, flanked by two anteriolaterally facing flat surfaces (one on each side of the anteriorly facing flat surface), and, to provide for holding of the trial or disc for an anterior insertion approach, a hole spaced from the anteriorly facing flat surface, the hole having a longitudinal axis parallel to the anteriorly facing flat surface.

The inserter/impactors include a shaft having a distal end that has angled flat surfaces corresponding to and fittable against the angled flat surfaces of the static trial or artificial intervertebral disc, and a holding pin that extends from the center flat surface along a longitudinal axis of the shaft, the pin having a distal end that bends downward. The holding pin is spring loaded in a central channel of the shaft, so that it is biased toward and against a central flat surface (preferably, the bent end of the pin prevents it from entering the central channel). A flange, mechanically connected to the pin and translating adjacent the shaft, can be pushed distally to overcome the bias of the spring to space the pin away from the central flat surface. In this position, the pin can be inserted in the hole in the baseplate of the artificial intervertebral disc. Releasing the knob allows the spring to pull the pin back, causing the anteriorly facing surface of the baseplate to be held against the central flat surface of the inserter/impactor and the anteriolaterally facing flat surfaces of the artificial intervertebral disc to be held against the other corresponding flat surfaces of the inserter/impactor. A knob on the inserter/impactor can be rotated about the longitudinal axis of the shaft to pull the pin tighter and lock its position to more securely hold the baseplate, and reverse rotated to unlock and loosen the pin. (In some embodiments of the inserter/impactor having a wedge plate, the holding pin protrudes from a wedge-shaped extended surface of the distal end of the inserter/impactor and is restricted from upward movement with respect to the distal head by the presence of the wedge-shaped extended surface of the distal end of the inserter/impactor. More particularly, with any attempted upward movement of the holding pin, the pin encounters the upper surface of the channel in which the pin travels, preventing any such upward movement.)

When the static trial or artificial intervertebral disc is held in this manner, rotation of the trial or disc about its longitudinal axis relative to the inserter/impactor is prevented by interference of the corners of the trial's or disc's flat surfaces and the corners of the inserter/impactor's flat surfaces, similar to the manner in which a wrench holding a nut prevents rotation of the nut relative to the wrench. Further, the holding of the trial or disc in this manner allows for some repositioning of the trial or disc in the intervertebral space via rotation of the trial or disc in either direction about the longitudinal axis of the intervertebral space. Further, in some embodiments of the inserter/impactor having a wedge plate, when the trial or disc is held in this manner, rotation of the trial or disc about a lateral axis of the trial or disc relative to the inserter/impactor is prevented by interference of the inwardly facing surface of the first baseplate (e.g., upper baseplate) of the trial or disc and the corresponding surface (e.g., upper surface) of the wedge on the distal end, and by interference of the inwardly facing surface of the second baseplate (e.g., lower baseplate) of the trial or disc and the corresponding surface (e.g., lower surface) of the wedge on the distal end. With regard to artificial discs, it is preferable that the wedge on the inserter/impactor will interfere between the first and second baseplates (e.g., upper and lower) so that the surfaces of the first and second baseplates align at a preferred 15 degrees angle of lordosis when the disc is held by the inserter/impactor.

Preferably, both of the baseplates of the static trial or disc have similarly configured flat surfaces, and both baseplates' flat surfaces fit against the angled flat surfaces of the inserter/impactor to provide for a more secure holding of the static trial or disc by the inserter/impactor. Also preferably, in order to provide for a holding of the static trial or disc for two additional (here, anteriolateral) insertion approaches, each static trial or disc also includes two additional holes, one spaced apart from one of the anteriolaterally facing flat surfaces, and the other spaced apart from the other of the anteriolaterally facing flat surfaces. Accordingly, operation of the inserter/impactor can fit the holding pin into either of these two additional holes, and hold the anteriolaterally facing flat surface (the one associated with the hole into which the pin is fit) of the static trial or disc against the flat surface of the inserter/impactor opposite the pin. It should be understood that preferably, in order to facilitate these two additional approaches, the angle separating the anteriorly facing flat surface of the static trial or disc and one of the anteriolaterally facing flat surfaces of the static trial or disc is equal to the angle separating the anteriorly facing flat surface and the other of the anteriolaterally facing flat surfaces.

Also preferably, as shown, the baseplates of each of the plurality of static trials are appropriately lordotically angled relative to one another to ease insertion of the static trial into the intervertebral space and to mimic how the artificial intervertebral disc will typically be oriented as it is being inserted. In some embodiments, the inserter/impactor holds the artificial intervertebral disc by the lower baseplate such that the upper baseplate is permitted to adjust its degree of lordosis relative to the lower baseplate during insertion, as described in greater detail below. In other embodiments, the inserter/impactor holds the baseplates in a fixed degree of lordosis relative to one another, as described in greater detail below.

With further regard to the repositioners/extractors described herein, each repositioner/extractor is provided primarily for repositioning and/or extracting a static trial or artificial intervertebral disc having features suitable for being manipulated by the repositioner/extractor. Exemplary suitable artificial intervertebral discs are described in the '160 and '528 applications with regard to FIGS. 8a-z, 9a-u, 10a-u, 11a-k, and 12a-p thereof and by the accompanying descriptions therefor (e.g., embodiments identified as the first, second, third, fourth, and fifth preferred embodiments of the fourth embodiment family, etc.). Regarding the features suitable for being manipulated by each repositioner/extractor, such features include at least two holes extending longitudinally into one of the baseplates of the static trial or artificial intervertebral disc from the inwardly facing surface of the baseplate. More than two holes can be used to provide for multiple repositioning/extracting approaches. Preferably, in order for the same repositioning/extracting tool to be used for multiple approaches on the same trial or artificial intervertebral disc, adjacent holes should be separated by the same distance separating other adjacent holes.

In order to engage the two holes, each repositioner/extractor has two pins extending in parallel from a central shaft, perpendicular to the longitudinal axis of the central shaft. The pins are spaced to engage the two holes simultaneously, and each pin has a diameter smaller than the diameter of the hole it is to engage. Therefore, the pins can be inserted into the holes, and pulling or pushing on the central shaft along its longitudinal axis when the holes are engaged pulls or pushes the static trial or artificial intervertebral disc in the intervertebral space. Further, because two holes are engaged, the static trial or artificial intervertebral disc can be rotated in either direction about a longitudinal axis passing through the intervertebral space, by rotating of the central shaft of the repositioner/extractor about its distal end, about an axis parallel to the longitudinal axes of the pins. A handle at a proximal end of the central shaft is useful for pushing or pulling on the shaft. A flange adjacent the proximal end of the shaft is useful for impaction (either with a distally directed force or a proximally directed force), if necessary to manipulate the shaft.

On each repositioner/extractor, the pins are formed on prongs that extend laterally from the central shaft. The direction of the prongs, and the location of the pins relative to the central shaft, determine the angle or angles of surgical approach for which a particular repositioner/extractor can be used. Further, the number and location of holes further determine the angle or angles of surgical approach for which a particular repositioner/extractor can be used. Accordingly, the present invention contemplates a variety of repositioner/extractors, and a variety of holes configurations, to provide the surgeon with a variety of possible surgical approach angles.

With further regard to the leveler described herein, the leveler is provided primarily for establishing a parallel orientation of the baseplates (relative to one another), and/or securing the purchase of the stabilizing spikes, of an artificial intervertebral disc having features suitable for being manipulated by the leveler. Exemplary suitable artificial intervertebral discs are described in the '160 and '528 applications with regard to FIGS. 8a-z, 9a-u, 10a-u, 11a-k, and 12a-p thereof and by the accompanying descriptions therefor (e.g., embodiments identified as the first, second, third, fourth, and fifth preferred embodiments of the fourth embodiment family, etc.). Regarding the features suitable for being manipulated by the leveler, such features include suitably formed inwardly facing surfaces of the baseplates of the artificial intervertebral disc.

More particularly, the leveler includes a shaft having a forked distal end formed by two opposing tongs that are symmetric to one another about a longitudinal axis of the shaft. Each of the tongs has an extent that initially curves laterally outward away from the shaft and from the other tong's extent, to define a central pocket forward of the shaft between the tongs' extents. Each tong's extent then resumes a distal direction to become parallel to the shaft and to the other tong's extent.

Each tong's extent has an upper surface and a lower surface. The upper surface is preferably shaped to conform against the inwardly facing surface of a first (e.g., upper) baseplate of an artificial intervertebral disc, and the lower surface is preferably shaped to conform against the inwardly facing surface of a second (e.g., lower) baseplate of the artificial intervertebral disc, so that insertion of the forked distal end of the leveler between the baseplates, with the central pocket of the distal end avoiding the central portion of the artificial intervertebral disc, and with the upper and lower surfaces so engaging the inwardly facing surfaces of the baseplates, causes the baseplates to be placed in parallel orientation with respect to one another. A handle is provided at a proximal end of the shaft for pushing, pulling, and otherwise manipulating the leveler as needed.

When the artificial intervertebral disc is inserted into the intervertebral space, its baseplates will typically be lordotically angled with respect to one another. The leveler can be applied to the artificial intervertebral disc to bring the baseplates parallel to one another. The forked distal end of the leveler is inserted so that the tongs' extents are placed between the inwardly facing surfaces of the baseplates, and so that the central pocket of the leveler avoids that portion of the artificial intervertebral disc that joins the baseplates. As the leveler is inserted, the tongs act as wedges to force the posterior portions of the baseplates away from one another. Accordingly, as the posterior portions are being separated, the stabilizing spikes on the outwardly facing surfaces of the baseplates find or secure their purchase in the hard bone of the outer ring of the vertebral body endplates. When the forked distal end is fully seated, the extents of the tongs hold the baseplates parallel to one another, and so that the spikes are fully engaged in the endplates.

BRIEF DESCRIPTION OF THE DRAWINGS

FIGS. 21-31 show top (FIG. 21), side (FIG. 22), perspective (FIG. 23), disassembly (FIGS. 24-30), and side cutaway (FIG. 31) views of a static trial holder of the present invention.

FIGS. 32-34 and 44 show side (FIG. 32), top (FIG. 33), perspective (FIG. 34), and side cutaway (FIG. 44) views of an alternate static trial holder 2000 of the present invention. FIGS. 35, 36, 37 and 38-39 show a sleeve of the alternate static trial holder 2000 in side (FIG. 35), top (FIG. 36), side cutaway (FIG. 37), front (FIG. 38), and back (with partial cutaway) (FIG. 39) views. FIGS. 40-42 show an extension of the alternate static trial holder 2000 in top (FIG. 40), proximal cutaway (FIG. 41), side (FIG. 42), and distal cutaway (FIG. 43) views.

FIGS. 71-73 show side (FIG. 71), perspective (FIG. 72), and close-up perspective (FIG. 73) views of a wedge plate inserter/impactor of the present invention.

DETAILED DESCRIPTION OF THE PREFERRED EMBODIMENTS

Figure 1:
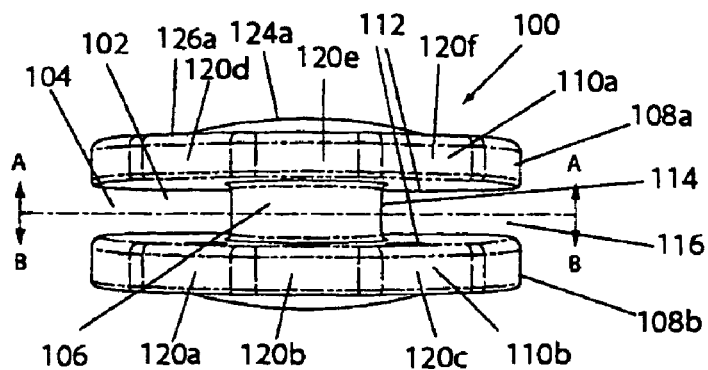
FIGS. 1-6 show front, (FIG. 1), side, (FIG. 2), perspective (FIG. 3), top (FIG. 4), bottom cutaway (FIG. 5) and top cutaway (FIG. 6) views of a static trial of the present invention.
Figure 2:
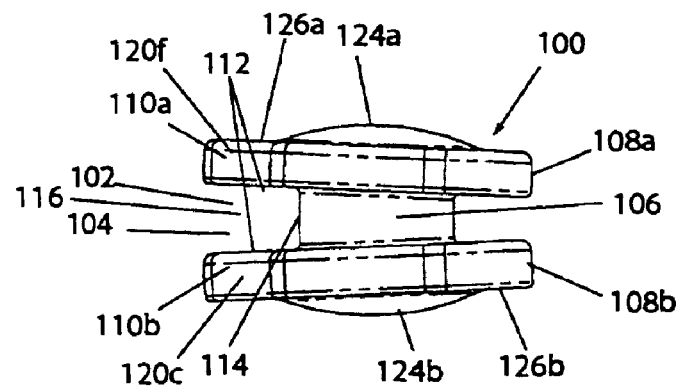
Figure 3:
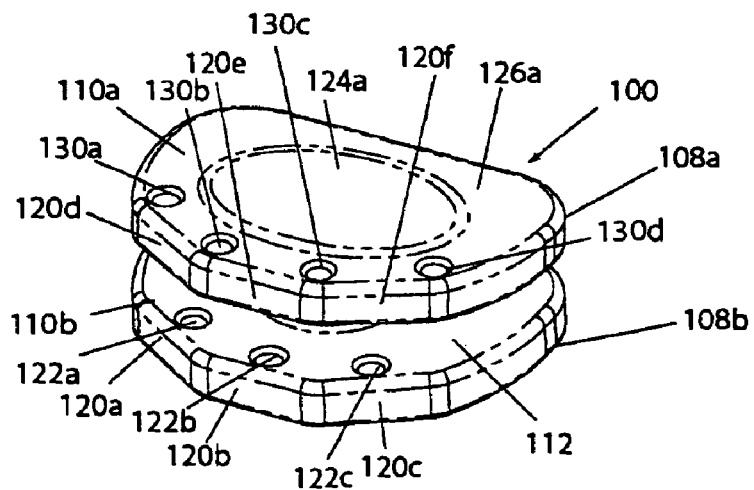
Figure 4:
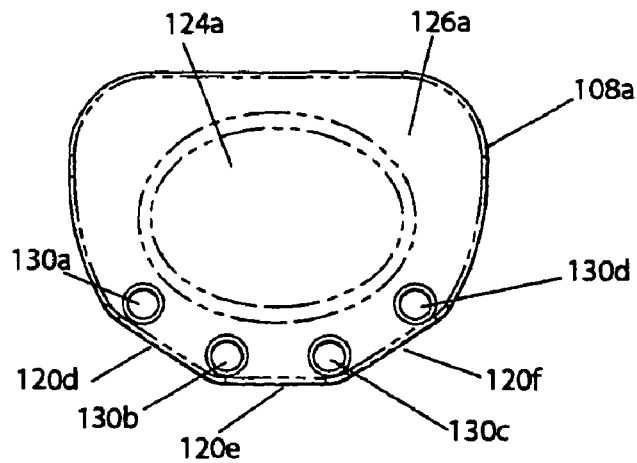
Figure 5:
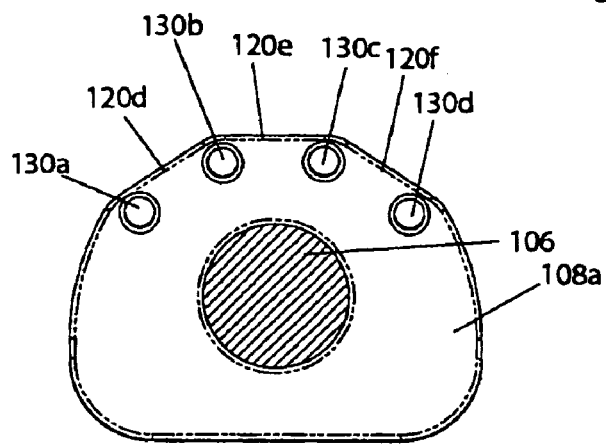
Figure 6:
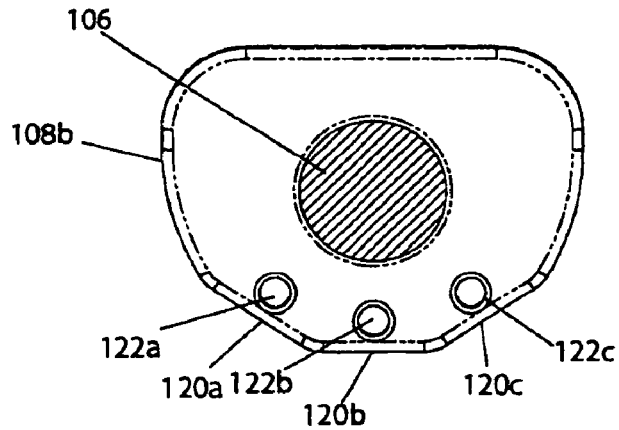
Figure 7:
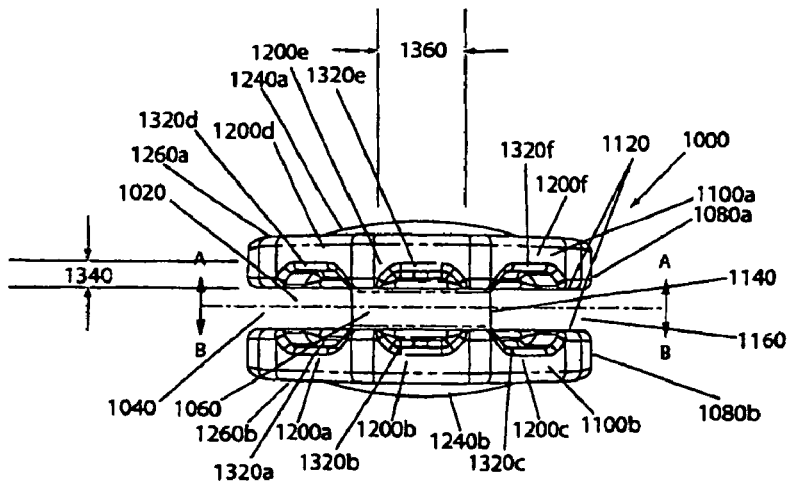
FIGS. 7-12 show front (FIG. 7), side (FIG. 8), perspective (FIG. 9), top (FIG. 10), bottom cutaway (FIG. 11), and top cutaway (FIG. 12) views of an alternate static trial of the present invention.
Figure 8:
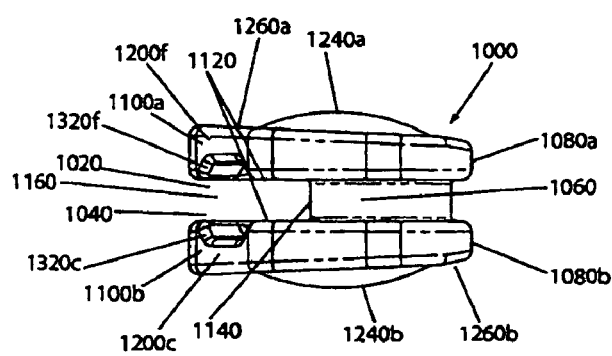
Figure 9:
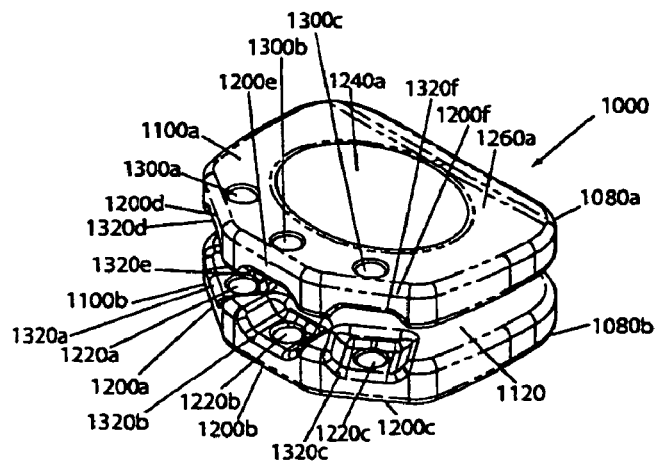
Figure 10:
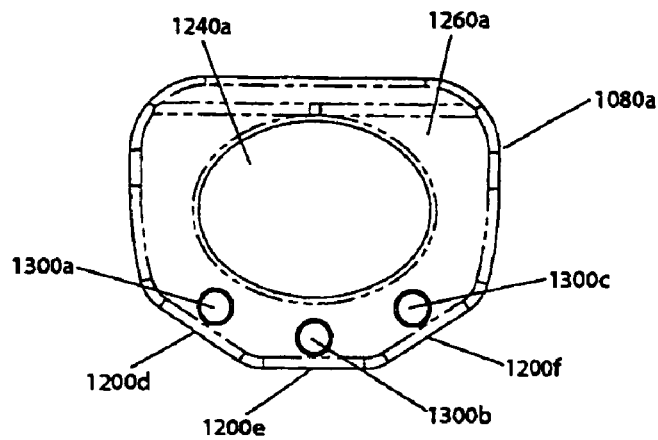
Figure 11:
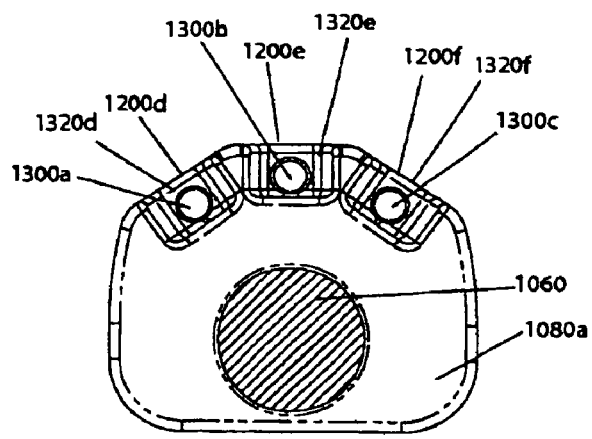
Figure 12:
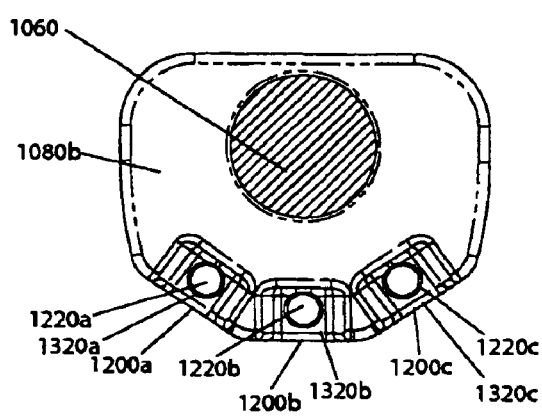
Figure 13:
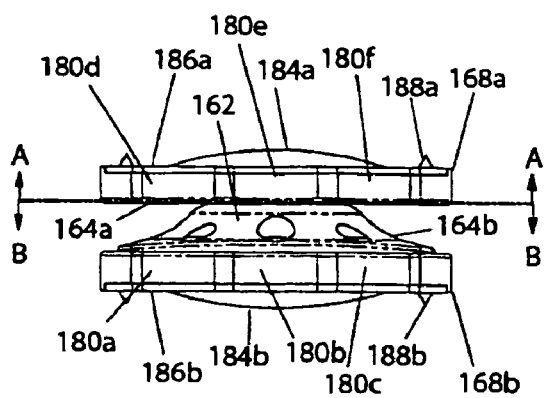
FIGS. 13-20 show front (FIG. 13), side cutaway (FIG. 14), top (FIG. 15), side cutaway (FIG. 16), bottom cutaway (FIG. 17), top cutaway (FIG. 18), bottom perspective (FIG. 19), and top perspective (FIG. 20) views of an exemplary artificial intervertebral disc of the present invention.
Figure 14:
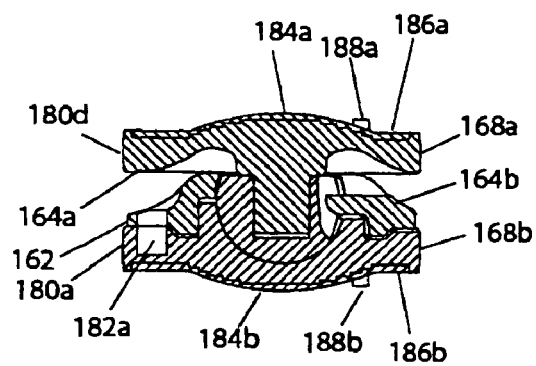
Figure 15:
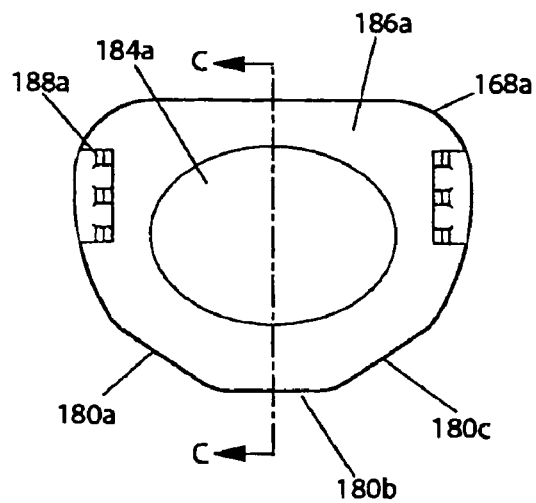
Figure 16:
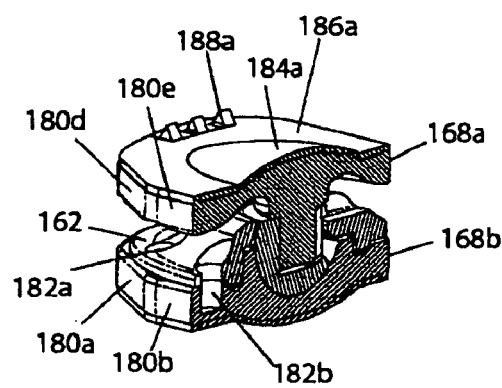
Figure 17:
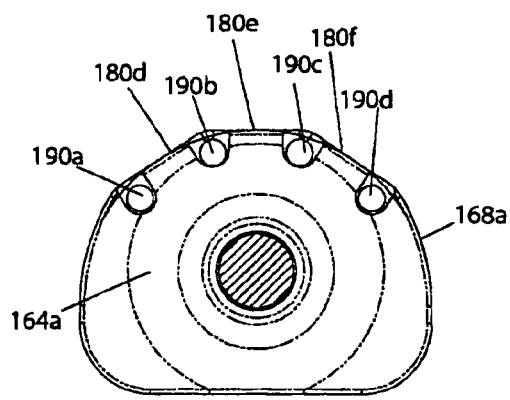
Figure 18:
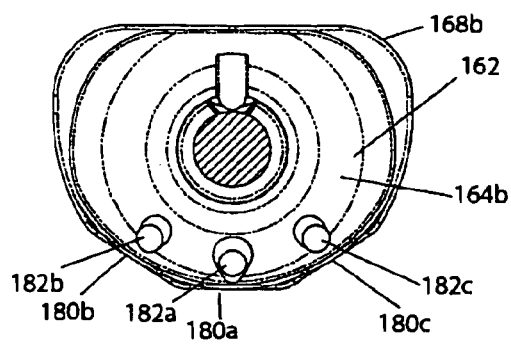
Figure 19:
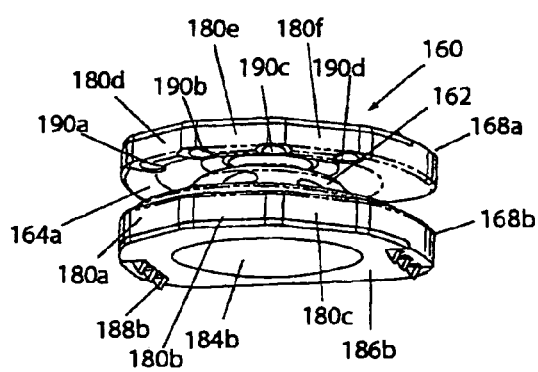
Figure 20:
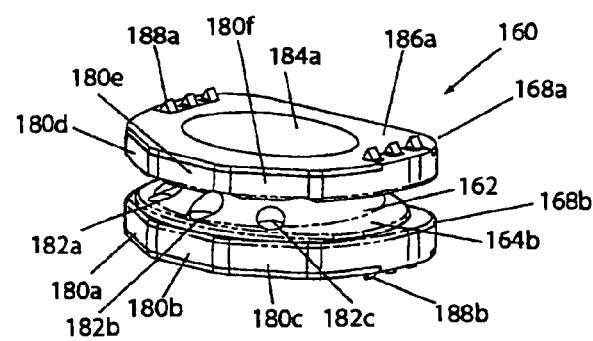
Figure 21:
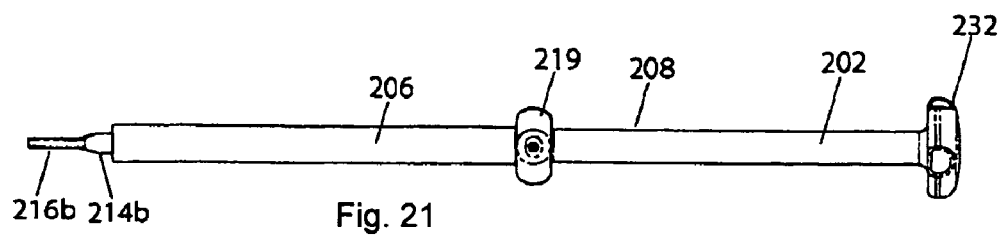
Figure 22:
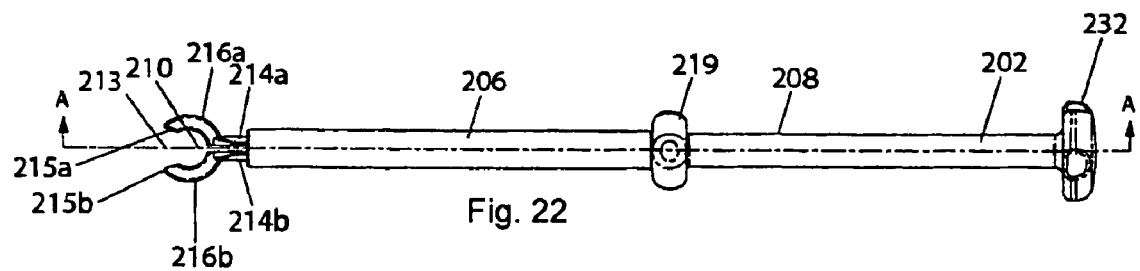
Figure 23:
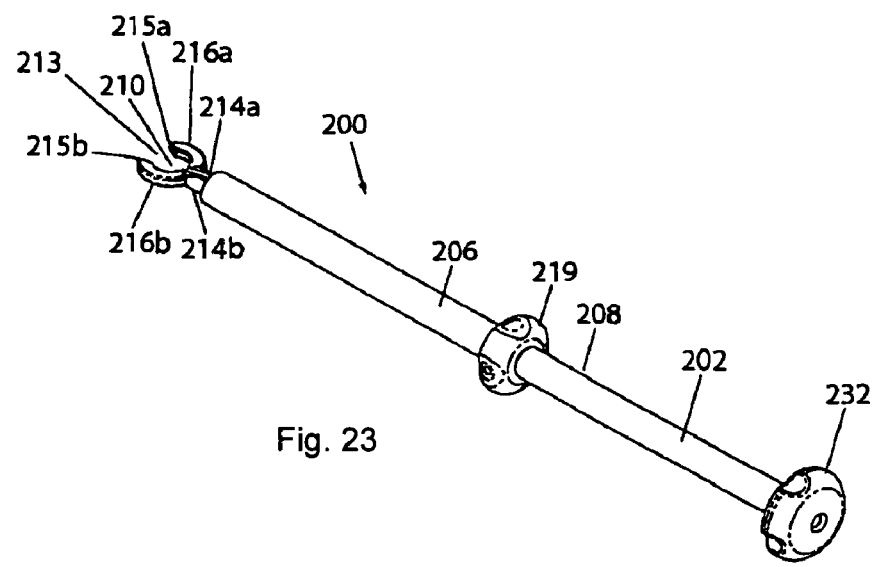
Figure 32:
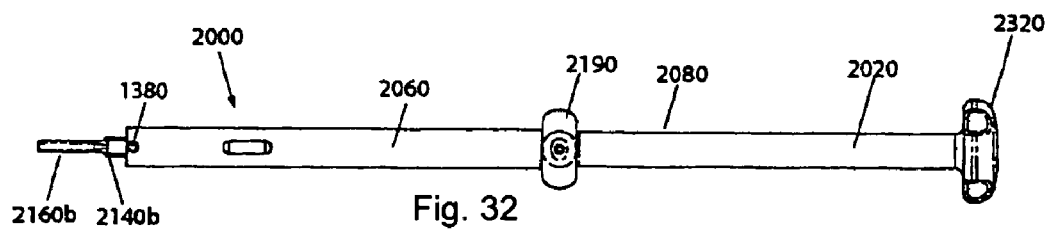
Figure 33:
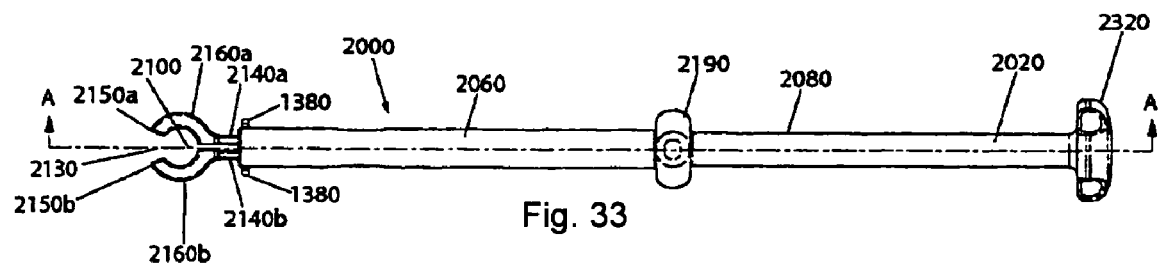
Figure 34:
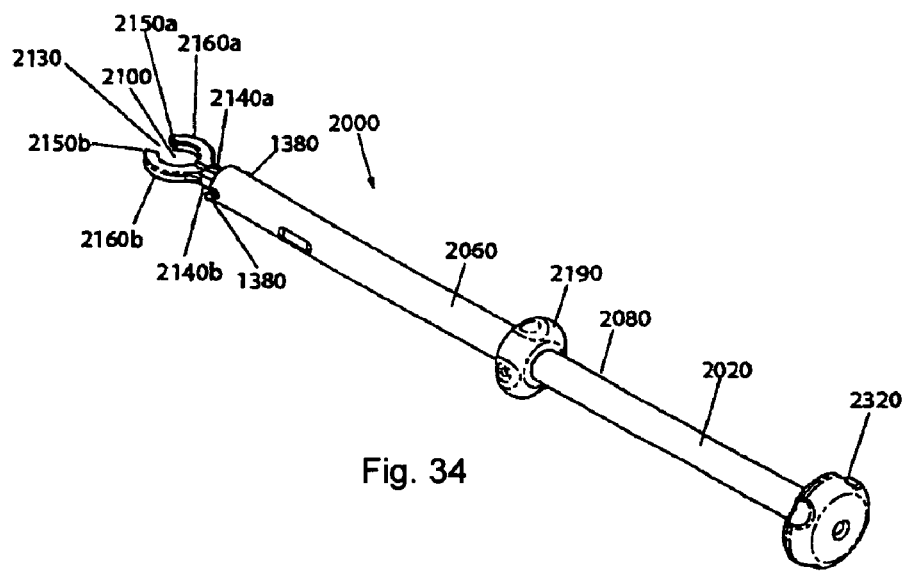
Figure 45:
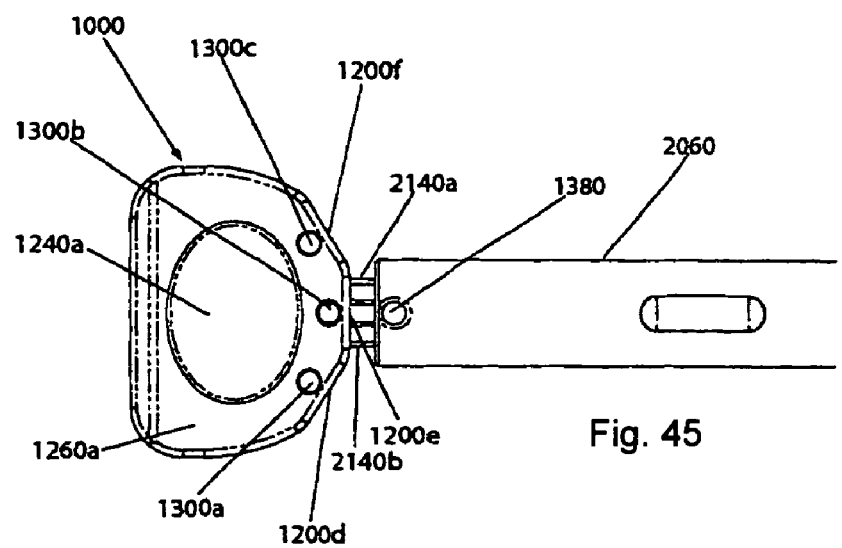
FIGS. 45-47 show top (FIG. 45), side (FIG. 46), and perspective (FIG. 47) views of the alternate static trial holder of FIGS. 32-44 holding an alternate static trial of FIGS. 7-12 from an anterior approach hold.

While the invention will be described more fully hereinafter with reference to the accompanying drawings, it is to be understood at the outset that persons skilled in the art may modify the invention herein described while achieving the functions and results of the invention. Accordingly, the descriptions that follow are to be understood as illustrative and exemplary of specific structures, aspects and features within the broad scope of the invention and not as limiting of such broad scope. Like numbers refer to similar features of like elements throughout.

Preferred embodiment of static trials of the present invention, and a preferred embodiment of an artificial intervertebral disc of the present invention, both for use with the instrumentation of the present invention, will now be described.

Referring now to FIGS. 1-6, a static trial of the present invention is shown in front (FIG. 1), side (FIG. 2), perspective (FIG. 3), top (FIG. 4), bottom cutaway (FIG. 5) and top cutaway (FIG. 6) views. Referring now to FIGS. 7-12 an alternate static trial of the present invention is shown in front (FIG. 7), side (FIG. 8), perspective (FIG. 9), top (FIG. 10), bottom cutaway (FIG. 11) and top cutaway (FIG. 12) views. Referring now to FIGS. 13-20 an artificial intervertebral disc of the present invention is shown in front (FIG. 13), side cutaway (FIG. 14), top (FIG. 15), side cutaway (FIG. 16), bottom cutaway (FIG. 17), top cutaway (FIG. 18), bottom perspective (FIG. 19), and top perspective (FIG. 20) views.

It should be understood that the illustration and reference herein to the artificial intervertebral disc shown in FIGS. 13-20 is merely to show an example of one type of artificial intervertebral disc that is contemplated by, encompassed by, and suitable for use with, the present invention, and that such illustration and reference herein is not meant to limit the scope of the present invention or limit the uses of the present invention. Rather, any other artificial intervertebral disc (or any other orthopedic device) having suitable features for being used with the instrumentation and methods described herein are contemplated by the present invention. Indeed, the features suitable for manipulation (e.g., the angled flat surfaces and adjacent holes and inwardly facing surfaces) are encompassed by the present invention, regardless of to what orthopedic device they may be applied. Other exemplary suitable artificial intervertebral discs include, but are not limited to, the artificial intervertebral discs described in the '160 and '528 applications with regard to FIGS. 8a-z, 9a-u, 10a-u, 11a-k, and 12a-p thereof and by the accompanying descriptions therefor (e.g., embodiments identified as the first, second, third, fourth, and fifth preferred embodiments of the fourth embodiment family, etc.). It should be noted that, as can be seen from FIGS. 13-20 that the artificial intervertebral disc shown in FIGS. 13-20 has features similar to those of these other suitable artificial intervertebral discs of the '160 and '528 applications, and it should be understood that such similar features are structurally and functionally as described in the '160 and '528 applications. Such similar features include an inwardly facing surface 164a of the upper baseplate 164a, and a convex structure 162 on the lower baseplate 168b, the convex structure 162 having an inwardly facing surface 164b.

And, while the instrumentation described herein (e.g., the static trials, static trial holders, dynamic trial, inserter/impactors, repositioners/extractors, and leveler) will be discussed for use with the artificial intervertebral disc of FIGS. 13-20, such discussions are merely by way of example and not intended to be limiting of their uses. Thus, it should be understood that the tools can be used with any of the artificial intervertebral discs disclosed in the '160 and '528 applications, or any other artificial intervertebral disc having (or being modifiable or modified to have) suitable features therefor. Moreover, it is anticipated that the features of the artificial intervertebral disc (e.g., the angled flat surfaces and accompanying holes and inwardly facing baseplate surfaces) and/or the static trials (e.g., the cylindrical trunks and angled flat surfaces and accompanying holes and/or engagement notches) that are used by the tools discussed herein to hold and/or manipulate these devices (such features, it should be noted, were first shown and disclosed in the '356, '585, '267, '160, and '528 applications) can be applied, individually or collectively or in various combinations, to other trials, spacers, artificial intervertebral discs or other orthopedic devices as stand-alone innovative features for enabling such trials, spacers, artificial intervertebral discs, or other orthopedic devices to be more efficiently and more effectively held and/or manipulated by the tools described herein or by other tools having suitable features. In addition, it should be understood that the invention encompasses artificial intervertebral discs, spacers, trials (static or dynamic), and/or other orthopedic devices, that have one or more of the features disclosed herein, in any combination, and that the invention is therefore not limited to artificial intervertebral discs, spacers, trials, and/or other orthopedic devices having all of the features simultaneously.

Referring to FIGS. 1-6 and 7-12, a plurality of static trials 100,1000 are provided primarily for use in determining the appropriate size of an artificial intervertebral disc to be implanted (or whether a particular size of the artificial intervertebral disc can be implanted) into the distracted intervertebral space (e.g., the artificial intervertebral disc 160 of FIGS. 13-20). Preferably, for each artificial intervertebral disc to be implanted, a plurality of sizes of the artificial intervertebral disc would be available. That is, preferably, a plurality of the same type of artificial intervertebral disc would be available, each of the plurality having a respective width and depth dimension combination that allows it to fit within a correspondingly dimensioned intervertebral space. For example, the plurality of artificial intervertebral discs could include artificial intervertebral discs having widths being either 35 mm or 40 mm, and depths ranging from 14 mm to 18 mm in 1 mm increments, for a total of 10 discs. Accordingly, preferably, each of the plurality of static trials 100,1000 for use with a particular plurality of differently sized artificial intervertebral discs would have a respective width and depth dimension set corresponding to the width and depth of a respective one of the plurality of differently sized artificial intervertebral discs. For example, the plurality of static trials 100,1000 for use with the set of artificial intervertebral discs described for example could include static trials having widths being either 35 mm or 40 mm, and depths ranging from 14 mm to 18 mm in 1 mm increments, for a total of 10 static trials. It should be understood that the artificial intervertebral discs and/or the static trials 100,1000 can be offered in a variety of dimensions without departing from the scope of the invention, and that the dimensions specifically identified and quantified herein are merely exemplary. Moreover, it should be understood that the set of static trials 100,1000 need not include the same number of trials for each artificial intervertebral disc in the set of artificial intervertebral discs, but rather, none, one, or more than one trial can be included in the trial set for any particular artificial intervertebral disc in the set.

Each of the static trials 100,1000 shown is exemplary for all of the static trials in the plurality of static trials; preferably the static trials in the plurality differ from one another only with regard to overall dimensions as described above) includes at least one feature that can be engaged by a tool. Suitable tools include, but are not limited to, the static trial holders described below, the inserter/impactors described below, and the repositioners/extractors described below.

Specifically, the static trial 100,1000 includes a recess 102,1020 that can be engaged by the opposing semicircular extents 216a-b,2160a-b of the static trial holder 200,2000. Preferably, this recess 102,1020 forms an annular groove 104,1040 that establishes a cylindrical trunk 106,1060 between the upper and lower baseplates 108a-b,1080a-b of the static trial 100,1000, such that the baseplates 108a-b, 1080a-b extend as flanges 110a-b,110a-b from either end of the cylindrical trunk 106,1060. Accordingly, preferably, the opposing semicircular extents 216a-b,2160a-b each have a thickness smaller than the width of the annular groove 104,1040, and as such fit into the annular groove 104,1040 to grip the cylindrical trunk 106,1060 between them. (Importantly, with regard to the alternate static trials 1000 being engaged by the alternate static trial holder 2000, as discussed in greater detail below, the body of the prongs 2140a-b (from which the semicircular extents 2160a-b extend) has a thickness greater than the width of the annular groove 1040 (and as such does not fit within the annular groove) but small enough to be accommodated by the opposing notches 1320a-b of the alternate static trial 1000 as described below.)

In some embodiments, while not shown in FIGS. 1-6 or FIGS. 7-12, it is also preferable that the annular groove 104,1040 radially widen outwardly, such that the walls 112,1120 of the annular groove 104,1040 are tapered toward one another with the increasing depth of the groove 104, 1040, such that the floor 114,1140 of the groove 104,1040 is more narrow than the opening 116,1160 of the groove 104,1040. Accordingly, preferably, in such embodiments, each semicircular extent 216a-b,2160a-b correspondingly radially widens outwardly, such that the thinner portion of the extent 216a-b,2160a-b fits closer to the floor 114,1140 of the annular groove 104,1040, so that the tapered surfaces of the extents 216a-b,2160a-b compress against the tapered walls 112,1120 of the annular groove 104,1040 when the static trial 100,1000 is engaged by the static trial holder 200,2000. This taper locking provides for a secure grip so that the static trial 100,1000 can be manipulated accurately and efficiently.

In some embodiments, while not shown in FIGS. 1-6 or FIGS. 7-12, it is also preferable that the floor of the annular groove 104,1040 of the cylindrical trunk 106,1060 be ridged (e.g., have ridges that run parallel to the longitudinal axis of the cylindrical trunk), and the surfaces of the semicircular extents 216a-b,2160a-b of the static trial holder 200,2000 that compress against the floor of the annular groove 104, 1040 when the static trial holder 200,2000 grips the static trial 100,1000 be correspondingly provided with ridges. The interlocking of the ridges of the static trial 100,1000 with the ridges of the static trial holder 200,2000 when the static trial 100,1000 is engaged prevents rotation of the static trial 100,1000 about the longitudinal axis of the cylindrical trunk 106,1060 with respect to the static trial holder 200,2000.

Preferably, as shown in FIGS. 7-12, each alternate static trial 1000 includes (on any alternate static trial surface that faces the desired engagement approach direction of the alternate static trial holder 2000) opposing recesses, preferably formed as upper and lower notches, an upper notch in the upper baseplate and a lower notch in the lower baseplate.

For example, opposing notches 1320b and 1320e are on each of the anteriorly facing flat surfaces of the upper 1080a and lower 1080b baseplates. And, for example, opposing notches 1320a and 1320d are on one of the anterior-laterally facing flat surfaces of the upper 1080a and lower 1080b baseplates. And, for example, opposing notches 1320c and 1320f are on the other of the anterior-laterally facing flat surfaces of the upper 1080a and lower 1080b baseplates. Preferably, the notches 1320a-f are sized so that the opposing notches of each pair (1320a,d, 1320b,e, and 1320c,f) form a volume that closely accommodates the dimensions of the alternate static trial holder's 2000 prongs' 2140a-b cross-section. That is, as described below, the body of each prong 2140a-b is thicker than the semicircular extent 2160a-b that extends from the body, and as such, whereas the semicircular extents 2160a-b fit into the annular groove 1040, the prongs 2140a-b do not because the depth 2260 of their cross-section (described below) is greater than the width of the annular groove opening 1160. However, each notch pair (1320a,d, 1320b,e, and 1320c,f) accommodates this greater thickness, in that each notch 1320a-f has a depth 1340, and, when the two notch depths 1340 of the opposing notches of the notch pair are taken together with the width of the annular groove 1040, the combined distance accommodates the depth 2260 of the static trial holder's 2000 prongs' 2140a-b cross-section. Further, each notch 1320a-f has a width 1360 that accommodates the width 2240 of the alternate static trial holder's 2000 prongs' 2140a-b cross-section. (It should be noted that the width 1360 accommodates the width 2240 of the alternate static trial holder's 2000 prongs' 2140a-b cross-section even when the prongs 2140a-b are separated to place the holding enclosure 2100 in an expanded state as described below. This enables the notches 1320a-f to accommodate the width 2240 of the prongs' cross-section as the cylindrical trunk 1060 of the static trial 1000 is being snapped into the holding enclosure 2100 as described below.) As such, as the opposing semicircular extents 2160a-b of the alternate static trial holder 2000 are placed into the annular groove 1040, the bodies of the prongs 2140a-b pass into the notches of the pair so that the semicircular extents 2160a-b can continue into the annular groove 1040 and be seated around the cylindrical trunk 1060. More specifically, the prongs 2140a-b of the alternate static trial holder 2000 fit into the notches above and below it (e.g., 1320b and 1320e for an anterior approach; 1320a and 1320d for an anterior-lateral approach; and 1320c and 1320f for another anterior-lateral approach). Once the prongs 2140a-b are fitted within the notch pair, interference between the prongs 2140a-b and the notch walls limits or prevents rotation of the alternate static trial 1000 about a longitudinal axis (e.g., an axis parallel to the longitudinal axis of the cylindrical trunk 1060) with respect to the alternate static trial holder 2000.

It should be understood that configurations having more or fewer notches, and in a variety of locations, are contemplated by the invention, and the detailed descriptions of only one type of notch configuration is not meant to limit the invention to only this configuration. Importantly, the invention encompasses using a single notch in a baseplate a single notch pair, or any number of notches or notch pairs, formed in any suitable manner with any suitable dimensions, in any number of locations on a spacer, a trial or an artificial intervertebral disc (not limited to locations on the baseplates), for purposes of enabling the spacer, trial, or disc to be engaged by a manipulation instrument (not limited to a static trial holder) that engages the notch, for the purpose of limiting rotation of the spacer, trial, or disc (or other orthopedic implant) with respect to the instrument or for any other purpose, and/or to enable the surgeon to work from a variety of approaches. For example, the notch configuration described herein, in cooperation with the alternate static trial holder, provides the surgeon with the ability to work from a directly anterior approach, as well as two anteriolateral approaches. It should be understood that additional notch configurations can enable the surgeon to work from a directly posterior approach, posteriolateral approaches, directly lateral approaches, or anteriolateral approaches that are different than those illustrated. For example, the placement of one or more suitably spaced notches (or the addition of one or more notches) on the posterior edge, and/or one or both of the lateral edges of one or both of the baseplates, would enable the surgeon to use the alternate static trial holder of the present invention to achieve such approaches.

Additionally with regard to features that can be engaged by a tool, each of the static trials 100,1000 includes at least one feature that can be engaged by a tool that preferably is also used to engage the artificial intervertebral disc that the trial approximates. Suitable tools that can engage both the trials and the artificial intervertebral disc include, but are not limited to, the inserter/impactors described below. Specifically, for being engaged by the inserter/impactors 400,4000, each static trial 100,1000 and artificial intervertebral disc 160 includes an anteriorly facing flat surface 120b,1200b, 180b, flanked by two anteriolaterally facing flat surfaces 120a,1200a,180a and 120c,1200c,180c (one on each side of the anteriorly facing flat surface 120b,1200b,180b), and, to provide for holding of the static trial 100,1000 or disc 160 for an anterior insertion approach, a hole 122b,1220b,182b spaced from the anteriorly facing flat surface 120b,1200b, 180b, the hole 122b,1220b,182b having a longitudinal axis parallel to the anteriorly facing flat surface 120b,1200b, 180b.

The holding pin 408,4080 of the inserter/impactor 400, 4000 fits within the hole 122b,1220b,182b, and the angled flat surfaces 120a-c,1200a-c,180a-c of the static trial 100, 1000 or disc 160 fit against the correspondingly angled flat surfaces 420a-c,4200a-c of the inserter/impactor 400,4000, and operation of the inserter/impactor 400,4000 pulls the holding pin 408,4080 toward the flat surface 120b,1200b, 180b of the inserter/impactor 400,4000 opposite the pin 408,4080, to rigidly hold the static trial 100,1000 or disc 160 by the structure of the static trial 100,1000 or disc 160 having the hole 122b,1220b,182b (e.g., the baseplate 108b, 1080b,168b).

When the static trial 100,1000 or disc 160 is held in this manner, rotation of the static trial 100,1000 or disc 160 about a longitudinal axis (of the static trial 100,1000 or disc 160) relative to the inserter/impactor 400,4000 is prevented by interference of the corners of the static trial's 100,1000 or disc's 160 flat surfaces 120a-c,1200a-c,180a-c and the corners of the inserter/impactor's 400,4000 flat surfaces 420a-c,4200a-c, similar to the manner in which a wrench holding a nut prevents rotation of the nut relative to the wrench. Further, the holding of the static trial 100,100 or disc 160 in this manner allows for some repositioning of the static trial 100,1000 or disc 160 in the intervertebral space via rotation of the static trial 100,1000 or disc 160 in either direction about the longitudinal axis of the intervertebral space.

Further, with regard to the wedge plate inserter/impactor 4000, when the static trial 100,1000 or disc 160 is held in this manner, rotation of the static trial 100,1000 or disc 160 about a lateral axis (of the static trial 100,1000 or disc 160) relative to the inserter/impactor 4000 is prevented by interference of the inwardly facing surface (e.g., 164a) of the first baseplate (e.g., upper baseplate) of the static trial 100,1000 or disc 160 and the upper surface 4200g of the wedge on the distal end 4040, and by interference of the inwardly facing surface (e.g., 164b) of the second baseplate (e.g., lower baseplate) of the static trial 100,1000 or disc 160 and the lower surface 4200h of the wedge on the distal end 4040. Accordingly, the holding of the static trial 100,1000 or disc 160 in this manner allows for some repositioning of the static trial 100,1000 or disc 160 in the intervertebral space via rotation of the static trial 100,1000 or disc 160 in either direction about the longitudinal or latitudinal axis of the intervertebral space.

Preferably, both of the baseplates of the static trial 100, 1000 or disc 160 have similarly configured flat surfaces. For example, the lower baseplate's 108b,1080b,168b flat surfaces 120a-c,1200a-c,180a-c have similarly configured and similarly oriented counterpart flat surfaces 120d-f,1200d-f, 180d-f on the upper baseplate 108a,1080a,168a. Further preferably, both baseplates' 108a-b,1080a,168a-b flat surfaces 120a-f,1200a-f,180a-f face the angled flat surfaces 420a-c,4200a-f of the inserter/impactor 400,4000 when the static trial 100,1000 or disc 160 is held by the inserter/impactor 400,4000. For example, in an anterior approach for the trial 100,1000 (as shown in FIGS. 59-62, showing the trial 100 being held by the inserter/impactor 400 as an example for of how either trial 100,1000 can be held by either inserter/impactor 400,4000), 120a,1200a and 120d, 1200d facing 420a (or 4200a and 4200d), 120b,1200b and 120e,1200e facing 420b (or 4200b and 4200e), and 120c, 1200c and 120f,1200f facing 420c (or 4200c and 4200f), and in an anterior approach for the disc 160 (as shown in FIGS. 65-68, showing the disc 160 being held by the inserter/impactor 400 as an example for of how the disc 160 can be held by either inserter/impactor 400,4000), 180a and 180d facing 420a (or 4200a and 4200d), 180b and 180e facing 420b (or 4200b and 4200e), and 180c and 180f facing 420c (or 4200c and 4200f.

It should be noted that preferably, when the static trial 100,1000 is held by the inserter/impactor 400,4000, the flat surfaces 120a-c,1200a-c and the counterpart flat surfaces 120d-f,1200d-f are tightly held against the angled flat surfaces 420a-c,4200a-f of the inserter/impactor 400,4000 as described above. It is also preferable that the baseplates 108a-b,1080a-b of each of the plurality of static trials 100,1000 be appropriately lordotically angled relative to one another to ease insertion of the static trial 100,1000 into the intervertebral space and to mimic how the artificial intervertebral disc 160 will typically be oriented as it is being inserted using the inserter/impactor 400,4000. While not shown in FIGS. 1-6 or FIGS. 7-12 in some embodiments, when the static trials 100,1000 are formed in such a lordotically oriented configuration, it is preferable that the flat surfaces 120d-f,1200d-f on the first (e.g., upper) baseplate 108a,1080a be parallel to the flat surfaces 120a-c,1200a-c of the second (e.g., lower) baseplate 108b,1080b in the static trial's 100,1000 appropriately lordotically oriented configuration, so that when the static trial 100,1000 is held tightly by the inserter/impactor 400,4000, the flat surfaces 120a-f, 1200a-f are flush with the flat surfaces 420a-c,4200a-f of the inserter/impactor 400,4000 even though the baseplates 108a-b,1080a-b are lordotically angled with respect to one another.

With regard to the inserter/impactor 400, by contrast, preferably, when the artificial intervertebral disc 160 is held by the inserter/impactor 400, the flat surfaces 180a-c are tightly held against the angled flat surfaces 420a-c of the inserter/impactor 400 as described above, but the counterpart flat surfaces 180*d-f* are loosely held against the angled flat surfaces 420*a-c* of the inserter/impactor 400. As such, the structure of the artificial intervertebral disc 160 having the counterpart flat surfaces 180*d-f* (e.g., the upper baseplate 168*a*) is able to angulate and rotate to a limited extent relative to the structure of the artificial intervertebral disc 160 having the flat surfaces 180*a-c*. This permits the artificial intervertebral disc 160 to adjust to the intervertebral space (e.g., to the angulation of the adjacent vertebral endplates, defining the intervertebral space, relative to one another) as it is being inserted thereinto. That is, typically, the adjacent vertebral endplates will be lordotically angled with respect to one another as a result of the intervertebral space being prepared and distracted. As the artificial intervertebral disc 160 is then inserted into the intervertebral space using the inserter/impactor 400, then, the baseplates 168*a-b* will be permitted to lordotically angle with respect to one another to squeeze into the intervertebral space.

With regard to the wedge plate inserter/impactor 4000, when the artificial intervertebral disc 160 is held by the inserter/impactor 4000, the wedge surfaces of the distal end 4040 protrude from a distance midway with respect to the top and bottom of the distal end 4040 and span (e.g., right to left or vice-versa) the entire distal face of the distal end 4040, and the surfaces 4200*d-f* above the wedge on the distal end 4040 are respectively perpendicular to the wedge's upper surface 4200*g* such that each is disposed in parallel with its respective corresponding surface of the disc 160 when the disc 160 is held by the inserter/impactor 4000 at the appropriate lordosis angle. (And, accordingly, are angled approximately 15 degrees with respect to the surfaces below the wedge 4200*a-c*.)

Preferably, for an anterior approach, the wedge-shaped extension 4042 is designed and shaped to fit with its antero-lateral confronting surfaces (4200*d,f* and 4200*a,c*) tightly against the correspondingly antero-laterally facing surfaces (180*d,f* and 180*a,c*) of the disc 160, but such that its anterior confronting surfaces (4200*e* and 4200*b*) are slightly spaced from the anteriorly facing surfaces (180*d* and 180*b*) of the disc 160, when the disc is held by the inserter/impactor 4000. This is primarily to address manufacturing issues (in some instances, tolerances may not be adequately defined to ensure that all of those surfaces fit tightly against their corresponding surfaces), so that if there are manufacturing anomalies, any slight tolerance differences that may exist are nevertheless still adequate to ensure at least the tight fitting of the antero-lateral confronting surfaces, so that manipulation of the disc 160 is possible (e.g., in the manner of a wrench against an angled nut). This can be achieved; e.g., by designing the anterior confronting surfaces (4200*e* and 4200*b*) to each be slightly greater in length than the corresponding anteriorly facing surfaces (180*e* and 180*b*) of the disc baseplates, while still being angled with respect to the antero-lateral confronting surfaces (4200*d,f* and 4200*a,c*) at the same angle the antero-laterally facing surfaces (180*d,f* and 180*a,c*) of the disc baseplates are angled with respect to the anteriorly facing surfaces (180*e* and 180*b*) of the disc. The increased length of the anterior confronting surfaces on the wedge extension results in the slight clearance between the anteriorly facing surfaces (180*e* and 180*b*) of the disc and the corresponding anterior confronting surface (4200*e* and 4200*b*) of the wedged distal end, thereby ensuring that the disc will be fully seated against the antero-lateral confronting surfaces of the distal end despite possible manufacturing, material or other inevitable variations in tolerances of the artificial intervertebral disc or the inserter/impactor. As noted above, similar in this regard to the manner in which a wrench engages a nut, this fitting increases the mechanical advantage toward repositioning the disc in the intervertebral space. It should be noted, inasmuch as the inserter/impactor 4000 described herein can engage the disc from the antero-lateral angles as well, the anterior confronting surfaces (4200*e* and 4200*b*) should also be longer than the antero-laterally facing surfaces (180*d,f* and 180*a,c*) of the disc, so that a similar fitting occurs when the disc is held from the antero-lateral angles. Stated broadly, the primary confronting surfaces (e.g., the anterior confronting surfaces) of the inserter/impactor are preferably slightly longer than the primary confronted surfaces (e.g., anteriorly facing surfaces) of the disc for any given holding orientation.

Figure 63:
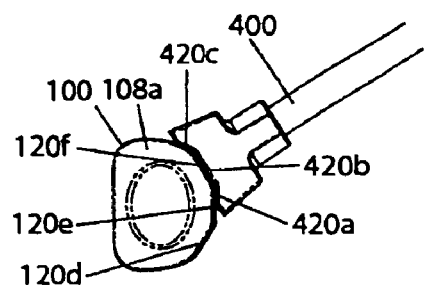
FIGS. 63-64 show top views of an inserter/impactor of the present invention holding a static trial of the present invention in two alternative ways.
Figure 64:
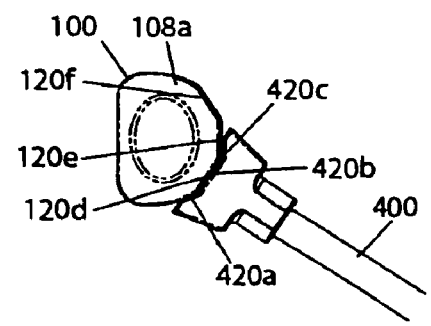
Figure 65:
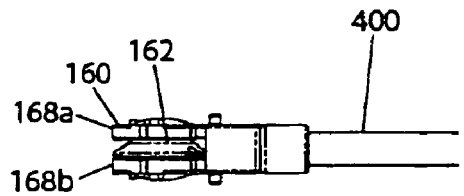
FIGS. 65-68 show side (FIG. 65), top (FIG. 66), side cutaway (FIG. 67), and perspective (FIG. 68) views of an inserter/impactor of the present invention holding an exemplary artificial intervertebral disc of the present invention.
Figure 66:
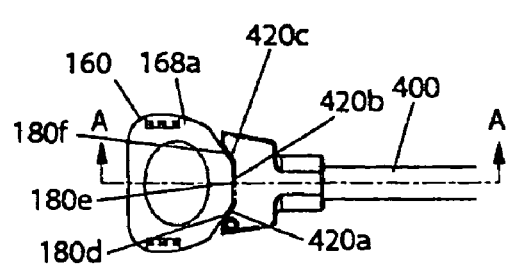
Figure 68:
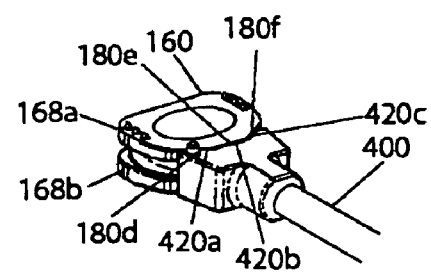
Figure 67:
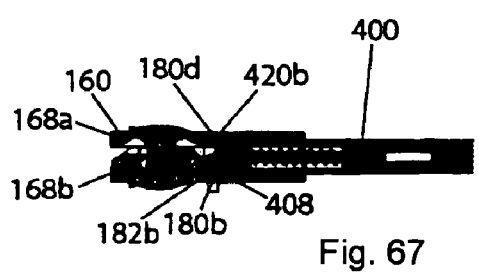
Figure 69:
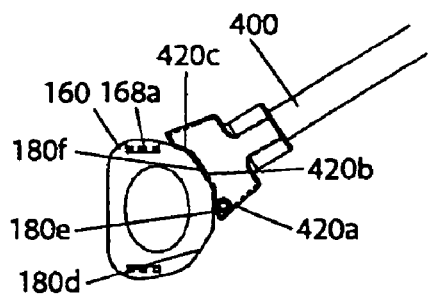
FIGS. 69-70 show top views of an inserter/impactor of the present invention holding an exemplary artificial intervertebral disc of the present invention in two alternative ways.
Figure 70:
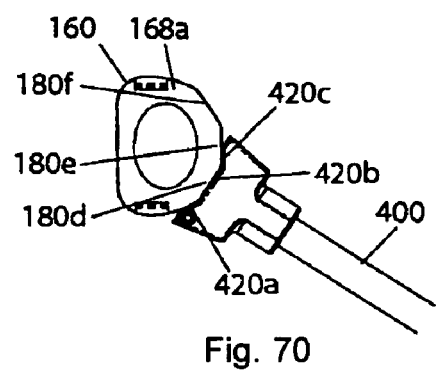
Figure 74:
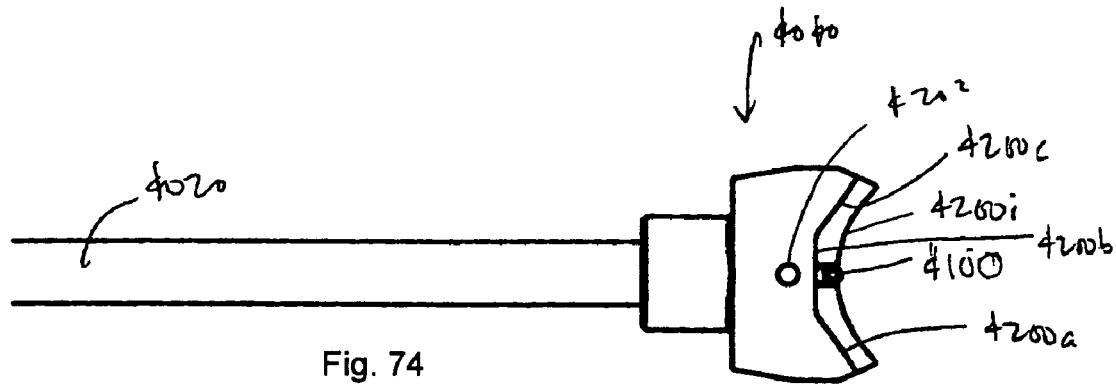
FIGS. 74-77 show bottom (FIG. 74), side (FIG. 75), top (FIG. 76), and side cutaway (FIG. 77) views of a distal end of a wedge plate inserter/impactor of the present invention.
Figure 75:
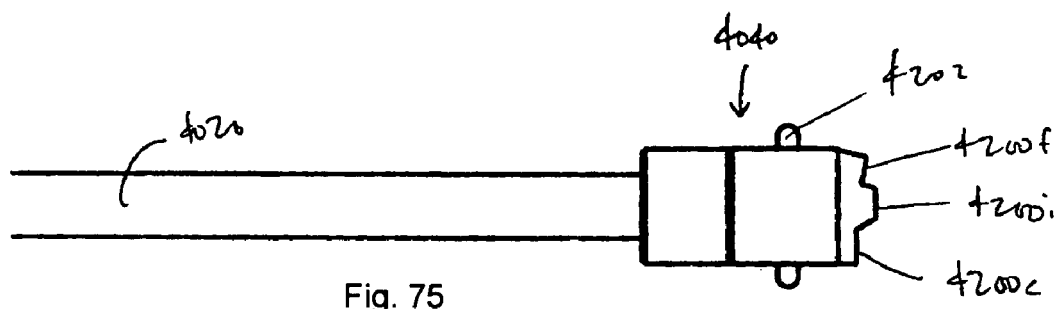
Figure 76:
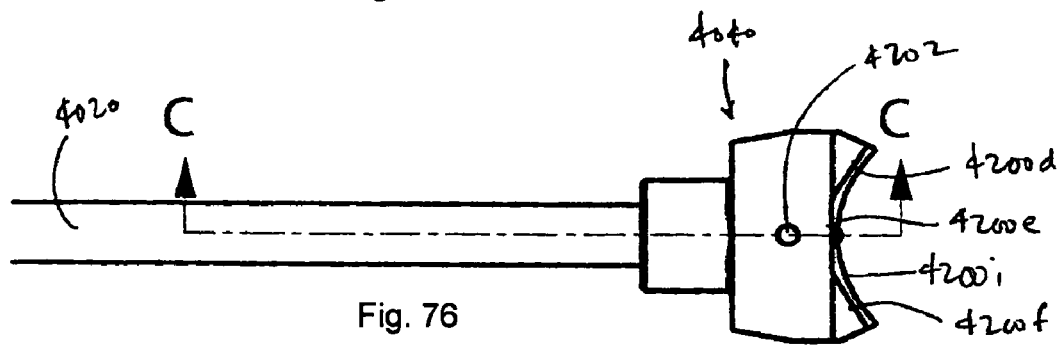
Figure 77:
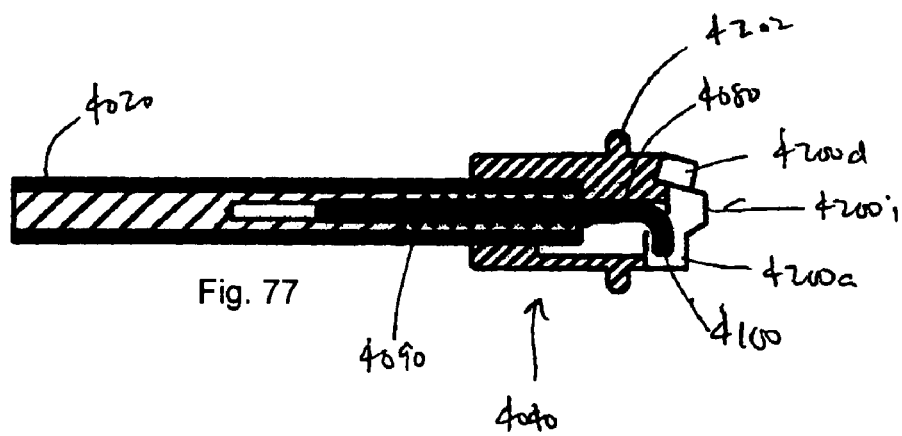

In order to provide for a holding of the static trial 100,1000 or disc 160 for two additional (here, anteriolateral) insertion approaches, each static trial 100,1000 or disc 160 also preferably includes two additional holes 122*a*,1220*a*, 182*a* and 122*c*,1200*c*,182*c*, one (e.g., 122*a*,1220*a*,182*a*) spaced apart from one of the anteriolaterally facing flat surfaces (e.g., 120*a*,1200*a*,180*a*), and the other (e.g., 122*c*, 1200*c*,182*c*) spaced apart from the other of the anteriolaterally facing flat surfaces (e.g., 120*c*,1200*c*,180*c*). Accordingly, operation of the inserter/impactor 400,4000 can fit the holding pin 408,4080 into either of these two additional holes 122*a*,1220*a*,182*a* or 122*c*,1200*c*,182*c*, and hold the associated anteriolaterally facing flat surface (the one associated with the hole into which the pin 408,4080 is fit) of the static trial 100,1000 or disc 160 against the flat surface of the inserter/impactor 400,4000 opposite the pin 408,4080. For example, in a first anteriolateral approach for the trial 100,1000 (as shown in FIG. 63 as an example of how either trial 100,1000 can be engaged by either inserter/impactor 400,4000), 120*a*,1200*a* and 120*d*,1200*d* not confronted, 120*b*,1200*b* and 120*e*,1200*e* facing 420*a* (or 4200*a* and 4200*d*), and 120*c*,1200*c* and 120*f*,1200*f* facing 420*b* (or 4200*b* and 4200*e*), and a first anteriolateral approach for the disc 160 (as shown in FIG. 69 as an example of the how the disc 160 can be engaged by either inserter/impactor 400, 4000), 180*a* and 180*d* not confronted, 180*b* and 180*e* facing 420*a* (or 4200*a* and 4200*d*), and 180*c* and 180*f* facing 420*b* (or 4200*b* and 4200*e*). And, for example, in a second anteriolateral approach for the trial 100 (as shown in FIG. 64 as an example of how either trial 100,1000 can be engaged by either inserter/impactor 400,4000), 120*a*,1200*a* and 120*d*,1200*d* facing 420*b* (or 4200*b* and 4200*e*), 120*b*,1200*b* and 120*e*,1200*e* facing 420*c* (or 4200*c* and 4200*f*), and 120*c*,1200*c* and 120*f*,1200*f* not confronted, and a second anteriolateral approach for the disc 160 (as shown in FIG. 70 as an example of how the disc 160 can be engaged by either inserter/impactor 400,4000), 180*a* and 180*d* facing 420*b* (or 4200*b* and 4200*e*), 180*b* and 180*e* facing 420*c* (or 4200*c* and 42000, and 180*c* and 180*f* not confronted.

It should be understood that preferably, in order to facilitate these additional approaches, the angle separating the anteriorly facing flat surface of the static trial 100,1000 or disc 160 and one of the anteriolaterally facing flat surfaces of the static trial 100,1000 or disc 160 is equal to the angle separating the anteriorly facing flat surface and the other of the anteriolaterally facing flat surfaces. Preferably, the surfaces are angled with respect to one another at an angle of 33.4 degrees.

It should also be understood that the inclusion of additional adjacent angulated surfaces and/or additional notches (or placing the angulated surfaces or notches in other locations on the trial or disc), and/or including corresponding holes adjacent to such angulated surfaces or notches, can provide the surgeon with additional approaches, e.g., other anteriolateral approaches, directly lateral approaches, posteriolateral approaches, and/or directly posterior approaches. For example, a trial or disc can have angled surfaces (and corresponding holes) along the entire perimeter of one or both of the baseplates, and thus enable the surgeon to engage the trial or disc from a number of angles, including anterior, posterior, lateral, anteriolateral, and posteriolateral angles. Or, for example, a trial (or disc) can have notches located on directly laterally facing surfaces or posterior surfaces or posterior-laterally facing surfaces, and thus enable the surgeon to engage the trial (or disc) with a static trial holder from a number of angles, including anterior, posterior, lateral, anteriolateral, and posteriolateral angles. (It should be noted that, while the opposing notches of the alternate static trials are shown formed in conjunction with the angulated surfaces of the baseplates, neither the number nor the placement of the opposing notches need coincide or be related to the number or placement of the angulated surfaces of the baseplates. For example, the notches can be applied to a trial or disc having curved approach surfaces.)

Additionally with regard to features that can be engaged by a tool, each of the static trials 100,1000 includes at least one feature that can be engaged by a tool that preferably is also used to engage the artificial intervertebral disc that the trial approximates. Suitable tools that can engage both the trial and the artificial intervertebral disc include, but are not limited to, the repositioners/extractors 500,510,520,530,540 described below. Specifically, for being engaged by the repositioners/extractors, each static trial 100,1000 and artificial intervertebral disc 160 includes at least two holes extending longitudinally into one of the baseplates of the static trial 100,1000 or artificial intervertebral disc 160 from the inwardly facing surface of the baseplate. More than two holes can be used to provide for multiple repositioning/extracting approaches. Preferably, in order for the same repositioning/extracting tool to be used for multiple approaches on the same trial or artificial intervertebral disc, adjacent holes should be separated by the same distance separating other adjacent holes.

As discussed in greater detail below with regard to the repositioners/extractors 500,510,520,530,540, in order to engage two of the holes, each repositioner/extractor has two pins extending in parallel from a central shaft, perpendicular to the longitudinal axis of the central shaft. The pins are spaced to engage the two holes simultaneously, and each pin has a diameter smaller than the diameter of the hole it is to engage. Therefore, the pins can be inserted into the holes, and pulling or pushing on the central shaft along its longitudinal axis when the holes are engaged pulls or pushes the static trial or artificial intervertebral disc in the intervertebral space. Further, because two holes are engaged, the static trial or artificial intervertebral disc can be rotated in either direction about a longitudinal axis passing through the intervertebral space, by rotating the central shaft of the repositioner/extractor about its distal end, about an axis parallel to the longitudinal axes of the pins. A handle at a proximal end of the central shaft is useful for pushing or pulling on the shaft. A flange adjacent the proximal end of the shaft is useful for impaction (either with a distally directed force or a proximally directed force), if necessary to manipulate the shaft.

On each repositioner/extractor, the pins are formed on prongs that extend laterally from the central shaft. The direction of the prongs, and the location of the pins relative to the central shaft, determine the angle or angles of surgical approach for which a particular repositioner/extractor can be used. Further, the number and location of holes further determine the angle or angles of surgical approach for which a particular repositioner/extractor can be used. Accordingly, the present invention contemplates a variety of repositioner/extractors, and a variety of holes configurations, to provide the surgeon with a variety of possible surgical approach angles.

As described in greater detail below, three repositioner/extractors are illustrated and described (symmetric, offset left, and offset right) for example, and, for example, two hole configurations are illustrated and described. Referring again to FIGS. 1-20 and FIGS. 7-12, a first hole configuration includes the hole configuration described above, that is, three holes on one of the baseplates (e.g., the lower baseplate 108b,1080b,168b), the holes being configured so that a first hole 122b,1220b,182b is located in the anterior-posterior plane, and the adjacent (second 122a,1220a,182a and third 122c,1200c,182c) holes are located in respective opposing anteriolateral planes on either side of the first hole 122b, 1220b,182b. (This hole configuration is also shown in FIGS. 98-103, each of which shows a top cutaway view of the artificial intervertebral disc 160 of FIGS. 13-20, showing its lower baseplate 168b, having the first hole configuration, engaged by one of the repositioners/extractors 500,510,520. Each view of the lower baseplate 168b shows the first hole 182b, the second hole 182a, and the third hole 182c of the first hole configuration.)

Referring again to FIGS. 1-20, a second hole configuration includes four holes on one of the baseplates (e.g., the upper baseplate 108a,168a), the holes being configured so that first (e.g., 130c,190c) and second (e.g., 130b,190b) holes straddle the anterior-posterior plane, a third hole (e.g., 130d,190d) is located so that the third hole and the first hole straddle one of the opposing anteriolateral planes, and a fourth hole (e.g., 130a,190a) is located so that the fourth hole and the second hole straddle the other of the opposing anteriolateral planes. While this second hole configuration is not illustrated with regard to the static trials 1000, it should be understood that the static trials 1000 can be configured with such second hole configuration, or any other hole configuration, without departing from the scope of the present invention. (It should be noted that, while the opposing notches of the static trials 1000 are shown formed in conjunction with the holes in the baseplates, neither the number nor the placement of the opposing notches need coincide or be related to the number or placement of the holes in the baseplates.) (This second hole configuration is also shown in FIGS. 104-112, each of which shows a bottom cutaway view of the artificial intervertebral disc of FIGS. 1-20, showing its upper baseplate 168a, having the second hole configuration, engaged by one of the repositioners/extractors 500,510,520. Each view of the upper baseplate shows the first hole 190c, the second hole 190b, the third hole 190d, and the fourth hole 190a, of the second hole configuration.)

It should be understood that configurations having more or fewer holes, and in a variety of locations, are contemplated by the invention, and the detailed descriptions of only two hole configurations is not meant to limit the invention to only these two configurations. Importantly, the invention encompasses using a hole or any number of holes, bored at any suitable angle, whether parallel to other holes or not, in any number of locations on a spacer, a trial or an artificial intervertebral disc (not limited to locations on the baseplates), for purposes of enabling the spacer, trial, or disc to be engaged by a manipulation instrument (not limited to a repositioner/extractor) that engages the hole, and/or to enable the surgeon to work from a variety of approaches. For example, as described in more detail below, the first and second hole configurations described herein, in cooperation with the repositioner/extractors, provide the surgeon with the ability to work from a directly anterior approach, as well as several anteriolateral approaches. It should be understood that additional hole configurations can enable the surgeon to work from a directly posterior approach, posteriolateral approaches, directly lateral approaches, or anteriolateral approaches that are different that those illustrated. For example, the placement of one or more suitably spaced holes (or the addition of one or more holes) on the posterior edge, and/or one or both of the lateral edges of one or both of the baseplates, would enable the surgeon to use the repositioner/extractors of the present invention to achieve such approaches.

Thus, it can be seen that each of the repositioner/extractors can be used in more than one manner depending on the tool desired and the approach desired. These manners are described in greater detail below and illustrated in FIGS. 98-112 with regard to the detailed description of the repositioners/extractors.

Also preferably, the baseplates 108a-b,1080a-b of each of the plurality of static trials 100,1000 preferably has a convex dome 124a-b,1240a-b on its outwardly facing surface 126a-b,1260a-b that is shaped like the convex dome 184a-b on the outwardly facing surface 186a-b of the corresponding baseplate 168a-b of the artificial intervertebral disc 160 that the static trial 100,1000 approximates. Preferably, each convex dome 124a-b,1240a-b is smooth, rather than having a porous coating that is preferred for the convex domes 184a-b of the artificial intervertebral disc 160, and each outwardly facing surface 126a-b,1260a-b does not have stabilizing spikes such as the stabilizing spikes 188a-b on the outwardly facing surfaces 186a-b of the artificial intervertebral disc 160. The omission of these device stabilizing and bone ingrowth encouraging structures and surfaces on the static trials 100,1000 enables the surgeon to test the size of the artificial intervertebral disc 160 to be implanted without traumatically engaging the vertebral body endplates.

Accordingly, the surgeon can prepare and distract the intervertebral space, and then insert and remove at least one of the static trials (or more, as necessary) to find the size that is most appropriate for the intervertebral space.

Preferred embodiments of static trial holders of the present invention will now be described.

Referring to FIGS. 21-23 and 31, a static trial holder 200 of the present invention is shown in side (FIG. 21), top (FIG. 22), perspective, (FIG. 23), and side cutaway (FIG. 31) views. In addition, referring to FIGS. 24-26, a sleeve of the static trial holder is shown in side cutaway (FIG. 24), front (FIG. 25), and back (with partial cutaway) (FIG. 26) views. In addition, referring to FIGS. 27-29, an extension of the static trial holder is shown in top (FIG. 27), proximal cutaway (FIG. 28), side (FIG. 29), and distal cutaway (FIG. 30) views.

Referring to FIGS. 32-34 and 44, an alternate static trial holder 2000 of the present invention is shown in side (FIG. 32), top (FIG. 33), perspective (FIG. 34), and side cutaway (FIG. 44) views. In addition, referring to FIGS. 35, 36, 37, and 38-39, a sleeve of the alternate static trial holder 2000 is shown in side (FIG. 35), top (FIG. 36), side cutaway (FIG. 37), front (FIG. 38), and back (with partial cutaway) (FIG. 39) views. In addition, referring to FIGS. 40-42, an extension of the alternate static trial holder 2000 is shown in top (FIG. 40), proximal cutaway (FIG. 41), side (FIG. 42), and distal cutaway (FIG. 43) views.

The static trial holders 200,2000 are provided primarily for use in holding, inserting and removing the static trials 100,1000 described herein, or distraction spacers having suitable features therefor, such as the distraction spacers disclosed in the '127 application.

More specifically, each static trial holder 200,2000 includes a handle 202,2020, an extension 204,2040, and a sleeve 206,2060. As shown in FIGS. 31 and 44, the handle 202,2020 and the extension 204,2040 are fixed to one another (preferably by the distal end of the handle 202,2020 being fixed to the proximal end of the extension 204,2040) to form a shaft 208,2080. The sleeve 206,2060 surrounds the extension 204,2040 and is rotatable with respect to the handle 202,2040 and the extension 204,2040 about the longitudinal axis of the shaft 208,2080. The handle 202,2020 preferably has an flange 232,2320 at its proximal end for use in applying a distally or proximally directed force to position the static trial 100,1000 (or distraction spacer) into or out of the intervertebral space, and/or for use in helping the surgeon rotate the sleeve 206,2060 with respect to the extension 204,2040 (by engaging the flange 232,2320 and the control knob 219,2190 described below).

The distal end of the extension 204,2040 forms a contractable and expandable holding enclosure 210,2100 in that the distal end is divided at a fulcrum 212,2120 into two prongs 214a-b,2140a-b, each of which terminates in a semicircular extent 216a-b,2160a-b, each of which has a tapered end 215a-b,2150a-b. The extents 216a-b,2160a oriented such that the tapered ends 215a-b,2150a-b face one another to define a radially inwardly tapering mouth 213, 2130, and such that the semicircular openings oppose one another to define the holding enclosure 210,2100. The prongs 214a-b,2140a-b are spring biased toward a neutral position (preferably by the formation of the fulcrum 212, 2120 in combination with the strength of the material of which the extension 204,2040 is made) such that the holding enclosure 210,2100 is spring biased to a receptive state (described below), but the prongs 214a-b,2140a-b can be brought together to contract the holding enclosure 210,2100 to a contracted state, (described below) or the prongs 214a-b,2140a-b can be further separated to expand the holding enclosure 210,2100 to an expanded state (described below).

When the holding enclosure 210,2100 is in the receptive state, the width of the mouth 213,2130 of the holding enclosure 210,2100 does not accommodate the diameter of the cylindrical trunk 106,1060 of the static trial 100,1000 (or distraction spacer) for passage therethrough. However, from this receptive state, the mouth 213,2130 can be temporarily widened (placing the holding enclosure 210,2100 in its expanded state) to accommodate the diameter (for passage of the cylindrical trunk 106,1060 through the mouth 213, 2130), if a sufficient force is applied to overcome the neutral position bias of the prongs 214a-b,2140a-b and thus widen the mouth 213,2130. (Preferably, there is enough space between the outer surfaces of the prongs 214a-b,2140a-b and the inner surface of the bore 218,2180 of the sleeve, when the prongs 214a-b,2140a-b are in their neutral position, so that the prongs 214a-b,2140a-b can be separated without interference.) The sufficient force can be applied by pressing the cylindrical trunk 106,1060 against the tapered ends 215a-b,2150a-b of the mouth 213,2130, in that the separating force component of the radially inward force of the pressing will be applied to the semicircular extents 216a-b,2160a-b by the taper of the tapered ends 215a-b, 2150a-b. Because the holding enclosure 210,2100 is biased toward the receptive state, after the cylindrical trunk 106, 1060 is passed through the mouth 213,2130 and into the holding enclosure 210,2100, the holding enclosure 210,2100 will return to its receptive state in which the width of the mouth 213,2130 does not allow passage of the cylindrical trunk 106,1060 without the sufficient force. Preferably, the force required to widen the mouth 213,2130 is greater than gravity and/or the greatest force that will be experienced by moving the static trial holder 200,2000 prior to placing the holding enclosure 210,2100 in the contracted state. Therefore, once the cylindrical trunk 106,1060 is in the holding enclosure 210,2100, even before the holding enclosure 210, 2100 is placed in its contracted state, the cylindrical trunk 106,1060 will not escape the holding enclosure 210,2100 as the static trial holder 200,2000 is oriented with the holding enclosure 210,2100 downward, or is moved about.

It should be understood that when the static trial 100,1000 (or distraction spacer) is being held (either when the holding enclosure 210,2100 is in its receptive state or in its contracted state discussed below), because the semicylindrical extents 216a-b,2160a-b fit within the annular groove 104, 1040 of the static trial 100,1000 (or distraction spacer), the static trial 100,1000 (or distraction spacer) will not escape from the enclosure along the longitudinal axis of the cylindrical trunk 106,1060. That is, as noted above, the recess 102,1020 of each static trial 100,1000 (or distraction spacer) forms an annular groove 104,1040 that establishes the cylindrical trunk 106,1060 between the baseplates of the static trial (or distraction spacer), such that the baseplates extend as flanges from either end of the cylindrical trunk 106,1060. Accordingly, preferably, the opposing semicircular extents each have a thickness smaller than the width of the annular groove 104,1040, and as such fit into the annular groove 104,1040 to engage the cylindrical trunk 106,1060 between them.

In some embodiments, while not shown in FIGS. 1-6 or FIGS. 7-12 or FIGS. 21-31 or FIGS. 32-44, it is preferable that the annular groove 104,1040 radially widen outwardly, such that the walls of the annular groove 104,1040 taper toward one another with the increasing depth of the groove, such that the floor of the groove is more narrow than the opening 116,1160 of the groove. Accordingly, preferably, in such embodiments, each semicircular extent 216a-b, 2160a-b correspondingly radially widens outwardly, such that the thinner portion of the extent 216a-b,2160a-b fits closer to the floor of the annular groove 104,1040, so that the tapered surfaces 215a-b,215a-b of the extents 216a-b, 2160a-b compress against the tapered walls of the annular groove 104,1040 when the static trial 100,1000 is engaged by the static trial holder 200,2000. This taper locking provides for a secure grip so that the static trial 100,1000 can be manipulated accurately and efficiently.

In some embodiments, while not shown in FIGS. 1-6 or FIGS. 7-12 or FIGS. 21-31 or FIGS. 32-44, it is also preferable that the floor of the annular groove 104,1040 of the cylindrical trunk 106,1060 be ridged (e.g., have ridges that run parallel to the longitudinal axis of the cylindrical trunk), and the surfaces of the semicircular extents 216a-b, 2160a-b of the static trial holder 200,2000 that compress against the floor of the annular groove 104,1040 when the static trial holder 200,2000 engages the static trial 100,1000 be correspondingly provided with ridges. The interlocking of the ridges of the static trial 100,1000 with the ridges of the static trial holder 200,2000 when the static trial 100,1000 is engaged prevents rotation of the static trial 100,1000 about the longitudinal axis of the cylindrical trunk 106,1060 with respect to the static trial holder 200,2000.

In order to more tightly hold the static trial 100,1000 (or distraction spacer) for manipulation of the static trial 100, 1000 (or distraction spacer) during surgical procedures in which greater forces will be experienced by the static trial 100,1000 (or distraction spacer) and the static trial holder 200,2000, the holding enclosure 210,2100 can be placed in a contracted state. The holding enclosure 210,2100 can be considered "unlocked" in its receptive or expanded states, and "locked" in its contracted state, with respect to the nature of the hold that the static trial holder 200,2000 potentially can have or has on the cylindrical trunk 106, 1060. Preferably, when the holding enclosure 210,2100 is locked, a force greater than that which is applicable by an unaided surgeon or nurse (i.e., that which can be applied to remove the cylindrical trunk 106,1060 from the holding enclosure 210,2100 when the holding enclosure 210,2100 is in its receptive state), and greater than that which will be experienced by the static trial 100,1000 (or distraction spacer) and the static trial holder 200,2000 during surgical procedures) would be required to pull the cylindrical trunk 106,1060 out of the holding enclosure 210,2100. The placement of the holding enclosure 210,2100 in its locked state or unlocked state is effected by operation of a holding assembly that includes the extension 204,2040 and the sleeve 206, 2060 and the manner in which they are configured and interact.

More particularly, the prongs 214a-b,2140a-b can be brought together (or brought closer to one another; it should be understood that they need not touch to be encompassed by the present invention), to lock the holding enclosure 210,2100, by a rotation of the sleeve 206,2060 with respect to the handle 202,2020 and the extension 204,2040 about the longitudinal axis of the shaft 208,2080. A rotation control knob 219,2190 is provided to ease the rotation of the sleeve 206,2060. As shown in FIGS. 27 and 29-30 in view of FIGS. 24-25 and FIGS. 40 and 42-43 in view of FIGS. 35-38, the bore 218,2180 of the sleeve 206,2060 (shown in cutaway in FIGS. 25 and 38) defines a cross-section that has a width 220,2200 that is greater than its depth 222,2220. Further as shown in those figures, the prongs 214a-b,2140a-b when separated (shown in cutaway in FIGS. 30 and 43) define a cross-section having a width 224,2240 that is greater than its depth 226,2260, the width 224,2240 and depth 226,2260 of the prongs' cross-section being closely accommodated by the width 220,2200 and depth 222,2220 of the bore's cross-section. When the prongs 214a-b,2140a-b are together, the width of prongs' cross-section is closely accommodated by the depth 222,2220 of the bore's cross-section. Thus, when the sleeve 206,2060 is rotated with respect to the extension 204,2040, the sides of the bore defining the depth 222,2220 of its cross-section bear against the sides of the prongs 214a-b,2140a-b defining the width of their cross-section.

It should be noted that in order to ease the rotation of the sleeve 206,2060 so that the side of the bore 218,2180 can bear against the sides of the prongs 214a-b,2140a-b, the corners of the bore 218,2180 are radiused, and at least the sides (that face away from one another) of the prongs 214a-b,2140a-b are curved. Preferably, as shown, the prongs 214a-b,2140a-b when separated define a partial cylindrical cross-section. The effect of the bearing (of the sides of the bore 218,2180 against the sides of the prongs 214a-b,2140a-b) is borne by the space between the prongs 214a-b,2140a-b, so that the space narrows and the prongs 214a-b,2140a-b are brought toward one another until they are accommodated within the bore's depth 222,2220. The bringing together of the prongs 214a-b,2140a-b brings the semicircular extents 216a-b,2160a-b together to place the holding enclosure 210,2100 into its contracted state, locking it.

Preferably, with regard to the static trial holder 200, the sleeve 206 is biased toward establishing the holding enclosure 210 in either an unlocked position or a locked position. Stated alternatively, when the holding enclosure 210 is unlocked (or locked), the force required to begin rotation of the sleeve 206 is greater than the force required to continue rotating the sleeve 206 once rotation has begun. And, as the sleeve 206 is rotated toward a position that will unlock (or lock), the holding enclosure 210, it is biased toward stopping its rotation at that upcoming position. Stated alternatively, as the sleeve 206 is being rotated, the force required to rotate the sleeve 206 past that upcoming position is greater than the force that is required to rotate it prior to reaching that upcoming position.

This biasing of the sleeve 206 of the static trial holder 200 toward positions that will either unlock or lock the holding enclosure 210 is effected by the inclusion of at least one spaced recess 228 on the outer surface of the extension 204, and at least one radial bore 230 through the wall of the sleeve 206 (preferably through the rotation control knob 219 as shown), which bores 230 each have secured therein a spring plunger (not shown) (it should be understood that functionally equivalent devices can also be used in place of a spring plunger). Preferably, each recess 228 is associated with a respective cooperating bore 230 and spring plunger. When a given bore 230 (and spring plunger) is aligned with its associated recess 228, the sleeve 206 is in a position at which the holding enclosure 210 is either unlocked or locked. Each of the spring plungers is biased radially inwardly from the inner surface of the sleeve 206, and as such presses against the outer surface of the extension 204 as the sleeve 206 is being rotated. Thus, when a recess 230 is presented to the spring plunger, it plunges into the recess 230, stopping the rotation of the sleeve 206. In order to restart (or continue) rotation of the sleeve 206, the bias of the spring plunger must be overcome when the restarting (or continuing) rotational force is applied. In order to lower the overcoming force required to restart or continue the rotation, the end of the spring plunger is preferably convexly curvate, and the recess is concavely curvate. Preferably, four recesses 228 and bores 230 (and spring plungers) are provided, each pair representing one of four quarter-turn rotated positions of the sleeve 206. At each position of the sleeve 206, all four plungers plunge into the recesses 228, securing the sleeve 206 at that position until a sufficient force is applied to overcome their plunging bias.

Preferably, with regard to the alternate static trial holder 2000, the movement of the sleeve 2060 toward positions that will either unlock or lock the holding enclosure 2100, and the stopping of the sleeve 2060 at such positions, is effected by the inclusion of at least one groove 2280 that extends in a 90 degree arc on the outer surface of the extension 2040, and at least one radial bore 2300 through the wall of the sleeve 2060 (preferably through the rotation control knob 2190 as shown), which bores 2300 each have secured therein a dog headed screw (not shown) so that a head of the screw protrudes into interior of the sleeve (it should be understood that functionally equivalent devices can also be used in place of a dog headed screw). Preferably, each groove 2280 is associated with a respective cooperating bore 2300 and dog headed screw. When a given bore 2300 (and dog headed screw) is aligned with an end of its associated groove 2280, the sleeve 2060 is in a position at which the holding enclosure 2100 is either unlocked or locked (unlocked when the head of the screw is positioned at one end of the groove, locked when it is positioned at the other end of the groove). The head of the dog headed screw protrudes into the interior of the sleeve and into the groove 2280 and rides therein as the sleeve 2060 is rotated. When an end of the groove 2280 is reached by the head of the screw, the head of the screw stops against the wall of the groove 2280 at the end of the groove 2280, stopping the rotation of the sleeve 2060, and setting the holding enclosure 2100 to either the unlocked or locked position. In order to set the holding enclosure 2100 to the alternative position, the sleeve 2060 is reverse rotated, causing the head of the screw to ride in the groove 2280 in the opposite direction toward the other end of the groove 2280. When the head of the screw reaches the other end of the groove 2280, the head of the screw stops against the wall of the groove 2280 at that end of the groove 2280, stopping the rotation of the sleeve 2060, and setting the holding enclosure 2100 to the alternative position.

Further, with regard to the alternate static trial holder 2000, the sleeve 2060 preferably has on its exterior surface at least one stop protrusion 1380 that is positioned and dimensioned to extend dorsally or ventrally from the exterior surface when the holding enclosure is in its "locked" state (see FIGS. 45-50), so that when the surgeon inserts the static trial 100,1000 into the intervertebral space, the stop protrusions 1380 prevent the static trial 100,1000 from being inserted too far into the space (that is, so that the stop protrusions 1380 hit against the lips of the adjacent vertebral body endplates before the static trial 100,1000 is inserted too far). It should be understood that stop protrusions can be applied to the static trial holder 200 without departing from the scope of the invention.

Accordingly, the static trials 100,1000 of the invention (or distraction spacers such as those disclosed in the '127 application) can be held and manipulated with either static trial holder 200,2000, and from a variety of approach angles. Holding the handle 202,2020 of the static trial holder 200,2000 in one hand, an operator can push the cylindrical trunk 106,1060 of the static trial 100,1000 (or the distraction spacer) against the mouth 213,2130 of the holding enclosure 210,2100 with enough force to temporarily expand the mouth 213,2130 to a width that will accommodate the diameter of the cylindrical trunk 106,1060 for passage through the mouth 213,2130. The radially inward tapering of the sides of the mouth 213,2130 (the facing ends 215a-b, 2150a-b of the semicircular extents 216a-b,2160a-b of the prongs 214a-b,2140a-b) facilitates this insertion. It should be noted that, with regard to the alternate static trial holder 2000, as shown in FIGS. 45-50 with reference to FIGS. 7 and 43, the depth 2260 of the prongs' cross-section is closely accommodated by the depth of the opening establishing by the width of the annular groove 1020 of the alternate static trial 1000 and the depths 1340 of the notches in the pair of opposing notches (1320a,d, 1320b,d, or 1320c,f), and the width 2240 of the prongs' cross-section is accommodated by the width 1360 of the notches in the pair of opposing notches (1320a,d, 1320b,d, or 1320c,f), so that the prongs' cross-section fits into the opposing notches as, and when, the cylindrical trunk 1060 is surrounded by the semicircular extents 2160a-b. (That is, that the width 1360 of the notch pair accommodates the width 2240 of the static trial holder's 2000 prongs' 2140a-b cross-section even when the prongs 2140a-b are separated to place the holding enclosure 2100 in an expanded state as described below. This enables the notch pair to accommodate the width 2240 of the prongs' cross-section as the cylindrical trunk 1060 of the static trial 1000 is being snapped into the holding enclosure 2100.)

Once the cylindrical trunk 106,1060 has passed into the holding enclosure 210,2100, the operator can let go of the static trial 100,1000 (or distraction spacer) because the prongs 214a-b,2140a-b will be overcome by their bias toward their neutral state and thus hold the static trial 100,1000 in the holding enclosure 210,2100 to prevent the static trial 100,1000 from falling out or slipping out as the static trial holder 200,2000 is moved with the static trial 100,1000 prior to closing (e.g., locking) the holding enclosure 210,2100. (When the static trial 100,1000 (or distraction spacer) is being held in this manner, and the holding enclosure 210,2100 is unlocked, the static trial 100,1000 can be removed from the holding enclosure 210,2100 by a pulling of the static trial 100,1000 through the mouth 213,2130 of the holding enclosure 210,2100 with a force required to again temporarily overcome the bias of the prongs 214a-b,2140a-b toward their neutral state, to separate them and make the width of the mouth 213,2130 accommodate the diameter of the cylindrical trunk 106,1060.)

With regard to the static trial holder 200, once the operator is ready to lock the holding enclosure 210, while still gripping the handle 202 of the static trial holder 200, he rotates the rotation control knob 219 either clockwise or counterclockwise to move the sleeve 206 to the next quarter-turn position. If the rotation control knob 219 is rotated with enough force to cause the spring plungers in the bores 230 to back out of the recesses 228, the sleeve 206 will rotate as desired. Once the sleeve 206 has reached the next quarter-turn position, the spring plungers will find the recesses 228 associated with that position, and plunge into the recesses 228 to snap the sleeve 206 into the proper position. As the sleeve 206 rotates, the sides of the sleeve's bore's inner surface bear against the curved outer surfaces of the prongs 214a-b to push the prongs 214a-b together so that they are accommodated by the depth 222 of the bore 218. When the prongs 214a-b are pressed against one another and held in that closed position by the maintenance of the sleeve 206 in the new position (maintained by the spring plungers in the recesses 228), the semicircular extents 216a-b move toward one another and are correspondingly maintained together about the cylindrical trunk 106,1060. When the prongs 214a-b are held in this manner, the cylindrical trunk 106,1060 cannot be removed through the mouth 213 of the now-tighter (e.g., locked) holding enclosure 210 without the application of forces preferably greater than will be encountered when inserting and removing the static trial 100,1000 from the intervertebral space during the surgical procedures. Once the static trial 100,1000 has been inserted and removed from the intervertebral space (or the distraction spacer has been inserted and removed from the intervertebral space after being used to distract the space), the operator can lock the holding enclosure 210 by rotating the sleeve 206 another quarter turn (in either the clockwise or the counterclockwise direction). Again, if the rotation control knob 219 is rotated with enough force to cause the spring plungers to back out of the recesses 228, the sleeve 206 will rotate as desired. Once the sleeve 206 has reached the next quarter-turn position, the spring plungers will find the recesses 228 associated with that position, and plunge into the recesses 228 to snap the sleeve 206 into the proper position. As the sleeve 206 rotates, the sides of the sleeve's bore's inner surface move away from the curved outer surfaces of the prongs 214a-b and allow the prongs 214a-b to separate (under their own bias toward the neutral position) as they are accommodated by the width 220 of the bore 218. When the prongs 214a-b are separated and allowed to remain in that position by the maintenance of the sleeve 206 in the new position (maintained by the spring plungers in the recesses 228), the semicircular extents 216a-b are separated from one another and hold the cylindrical trunk 106,1060 against falling or slipping out. That is, the cylindrical trunk 106,1060 can be removed by the operator if the operator applies a sufficient force to widen the mouth 213 of the holding enclosure 210 enough to let the cylindrical trunk 106,1060 pass through the mouth 213. Once the static trial 100,1000 (or distraction spacer) is removed, another one can be inserted and manipulated if required.

With regard to the static trial holder 2000, once the operator is ready to lock the holding enclosure 2100, while still gripping the handle 2020 of the static trial holder 2000, he rotates the rotation control knob 2190 clockwise (or counterclockwise depending on how the grooves 2280 are configured; that is, they are illustrated as being configured to enable a locking with a clockwise rotation, and an unlocking with a subsequent counterclockwise rotation, although other embodiments can enable a locking with a counterclockwise rotation, and an unlocking with a clockwise rotation, to accommodate left-handed persons or right-handed persons or for other reasons) to rotate the sleeve 2060 ninety degrees to the next position. As the sleeve 2060 rotates, the head of the dog headed screw rides freely in the groove 2280, and the sides of the sleeve's bore's inner surface bear against the curved outer surfaces of the prongs 2140a-b to push the prongs 2140a-b together so that they are accommodated by the depth 2220 of the bore 2180. As the dog headed screw reaches the end of the groove 2280, the prongs 2140a-b are pressed against one another and the semicircular extents 2160a-b move toward one another. The prongs 2140a-b are held in and biased toward the closed position, and the semicircular extents 2160a-b are correspondingly maintained together about the cylindrical trunk 106,1060, by the fitting of the bore's surfaces against the prongs' surfaces. When the prongs 2140a-b are held in this manner, the cylindrical trunk 106,1060 cannot be removed through the mouth 2130 of the now-tighter (e.g., locked) holding enclosure 2100 without the application of forces preferably greater than will be encountered when inserting and removing the static trial 100,1000 from the intervertebral space during the surgical procedures.

Figure 46:
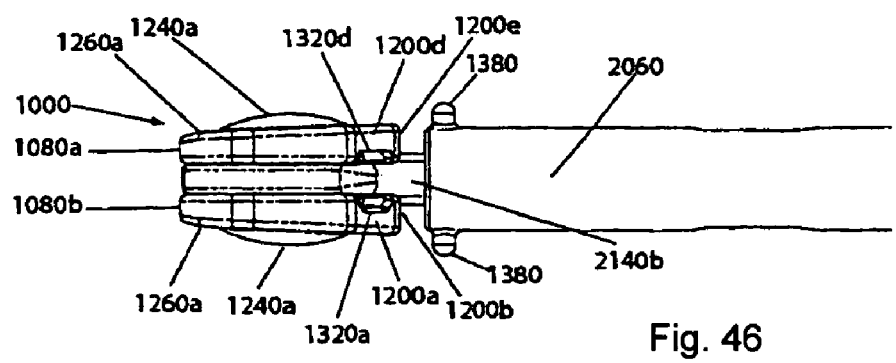
Figure 47:
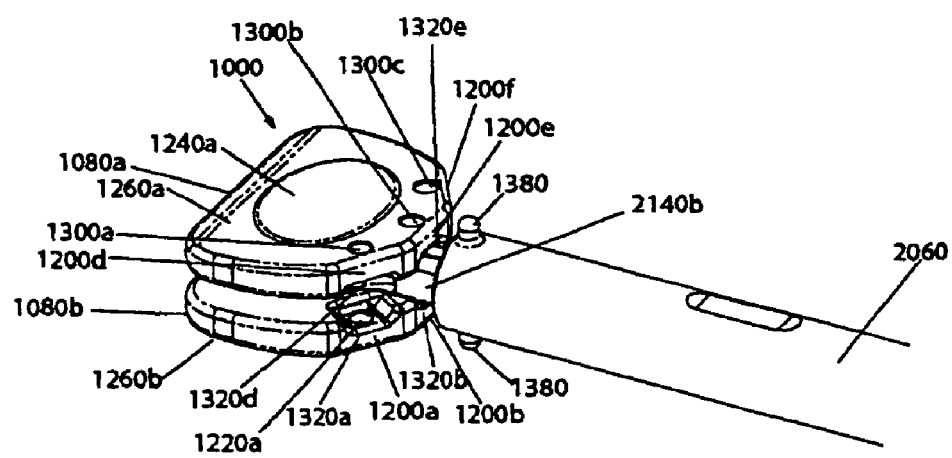

Further with regard to the static trial holder 2000 engaging the static trials 1000, the interference between the prongs 2140a-b and the opposing notches in the notch pair in which the prongs 2140a-b are disposed prevents rotation of the static trial 1000 about a longitudinal axis (e.g., an axis parallel to the longitudinal axis of the cylindrical trunk 1060) with respect to the static trial holder 2000. That is, if the static trial 1000 is encouraged, by forces encountered during manipulation of the static trial 1000, to rotate about such an axis with respect to the static trial holder 2000, the side walls of the notches will be confronted by the prong 2140a-b bodies and such rotational movement of the static trial 1000 will be stopped. (As can be seen in FIGS. 46-47, the prongs 2140a-b are too deep to fit into the annular groove 1060 without the notch pair accommodating their depth.) The same will happen if a reverse rotation about such an axis is attempted.

Figure 48:
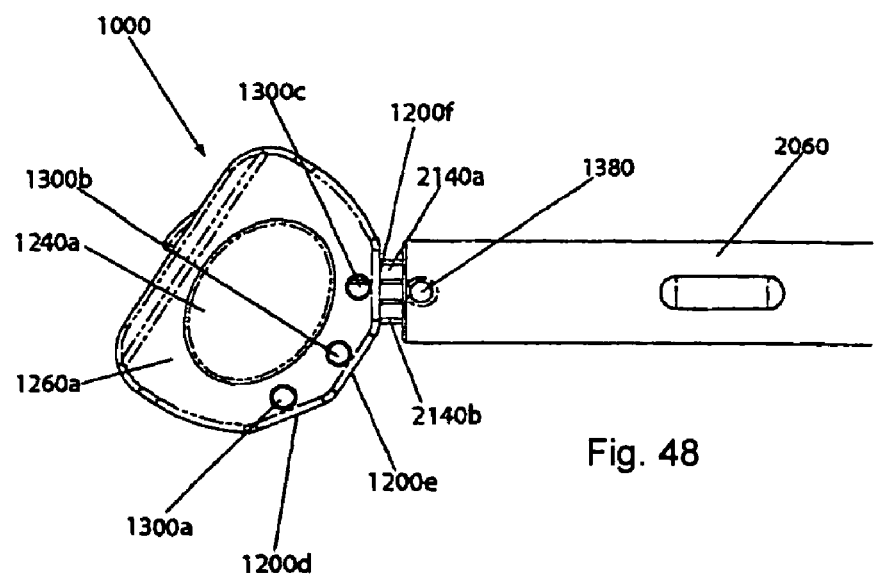
FIGS. 48-49 show top views of the alternate static trial holder of FIGS. 32-44 holding an alternate static trial of FIGS. 7-12 from two anterior-lateral approach holds.
Figure 49:
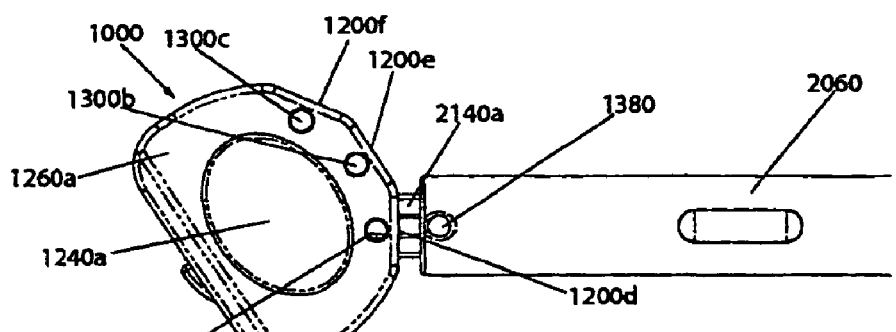
Figure 50:
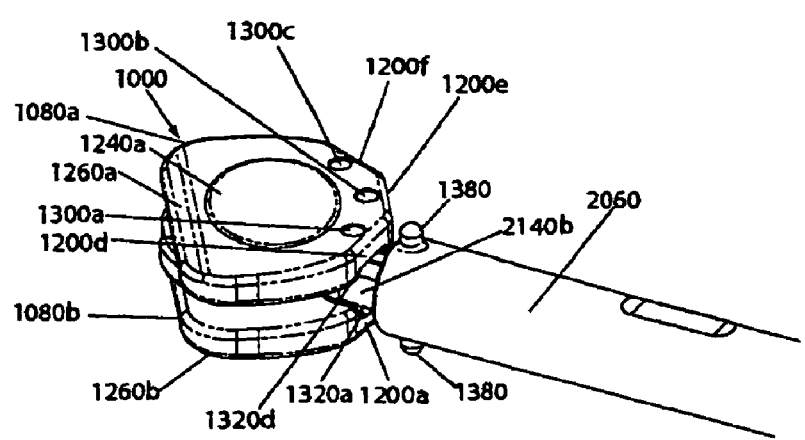
FIG. 50 shows a perspective view of the alternate static trial holder of FIGS. 32-44 holding an alternate static trial of FIGS. 7-12 from the anterior-lateral approach hold of FIG. 49.
Figure 51:
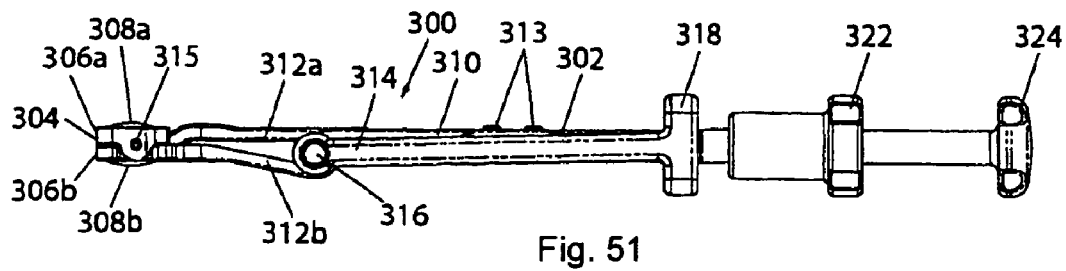
FIGS. 51-54 show side (FIG. 51), top (FIG. 52), side cutaway (FIG. 53), and perspective (FIG. 54) views of a dynamic trial of the present invention.
Figure 52:
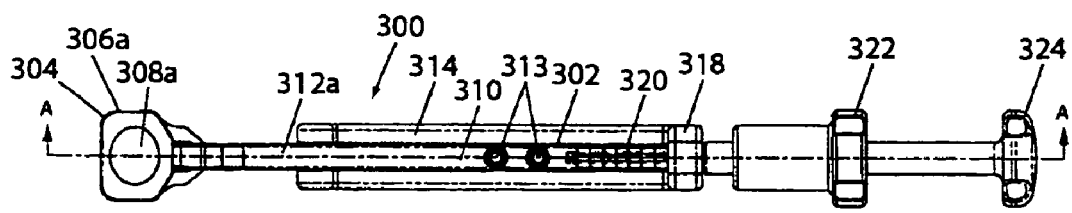
Figure 53:
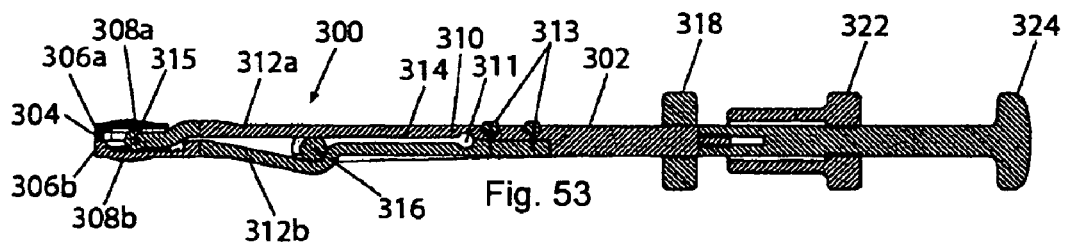
Figure 54:
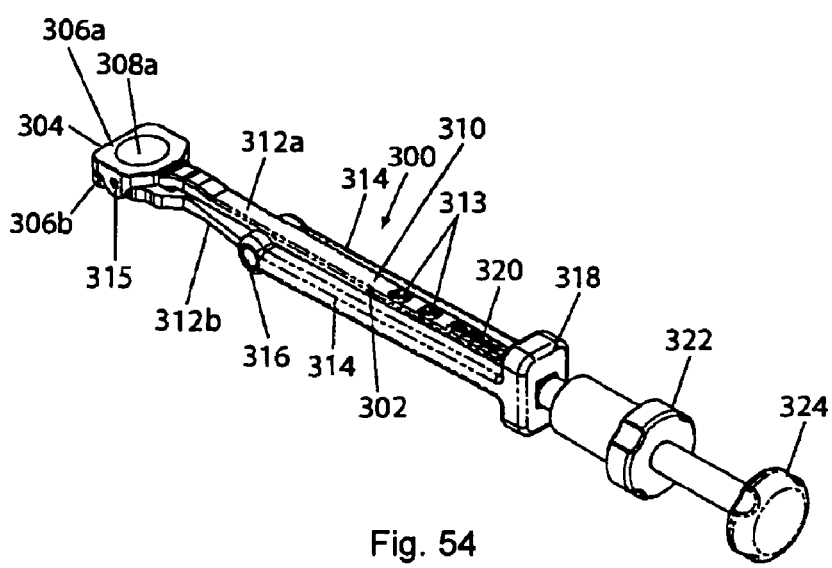
Figure 55:
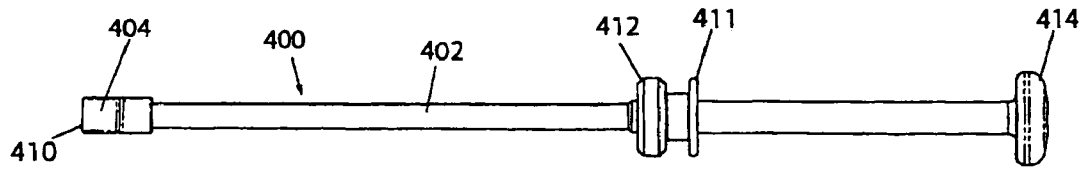
FIGS. 55-58 show side (FIG. 55), top (FIG. 56), side cutaway (FIG. 57), and perspective (FIG. 58) views of an inserter/impactor of the present invention.
Figure 56:
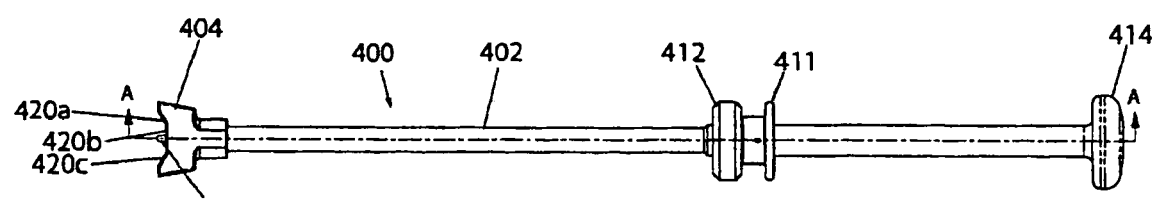
Figure 57:
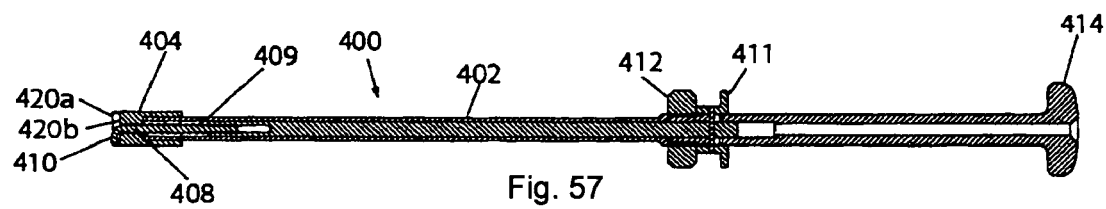
Figure 58:
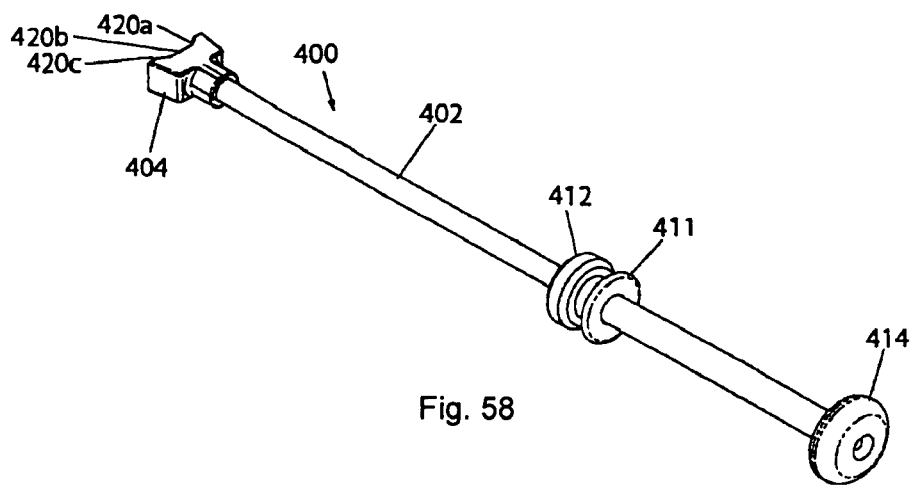
Figure 59:
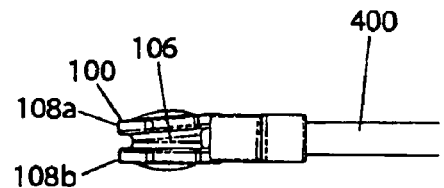
FIGS. 59-62 show side (FIG. 59), top (FIG. 60), side cutaway (FIG. 61), and perspective (FIG. 62) views of an inserter/impactor of the present invention holding a static trial of the present invention.
Figure 60:
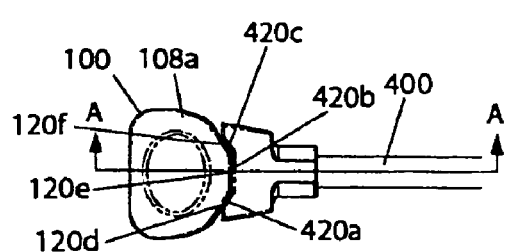
Figure 62:
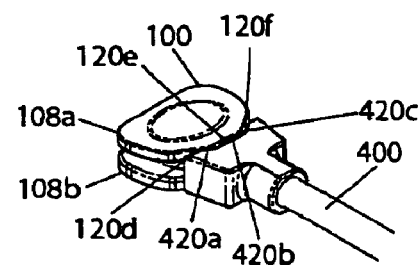
Figure 61:
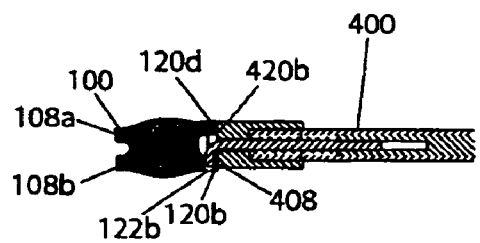

Further with regard to the static trial holder 2000, once the static trial 100,1000 has been inserted and removed from the intervertebral space (or the distraction spacer has been inserted and removed from the intervertebral space after being used to distract the space), the operator can unlock the holding enclosure 2100 by reverse rotating the sleeve 2060 (with enough initial force to overcome the biasing of the fitting of the bore's and the prongs' surfaces) ninety degrees. Again, as the sleeve 2060 rotates, the sides of the sleeve's bore's inner surface move away from the curved outer surfaces of the prongs 2140*a-b* and allow the prongs 2140*a-b* to separate (under their own bias toward the neutral position) as they are accommodated by the width 2200 of the bore 2180. When the prongs 2140*a-b* are separated and allowed to remain in that position by the maintenance of the sleeve 2060 in the new position (with the head of the dog headed screw against the wall of the groove 2280 at the other end of the groove 2280), the semicircular extents 2160*a-b* are separated from one another and hold the cylindrical trunk 106,1060 against falling or slipping out. That is, the cylindrical trunk 106,1060 can be removed by the operator if the operator applies a sufficient force to widen the mouth 2130 of the holding enclosure 2100 enough to let the cylindrical trunk 106,1060 pass through the mouth 2130. Once the static trial 100,1000 (or distraction spacer) is removed, another one can be inserted and manipulated if required. As shown in FIGS. 48-50, in addition to the anterior approach angle shown in FIGS. 45-47, the illustrated notch configuration accommodates two anterior-lateral approach angles as well.

Accordingly, the static trial holder 200,2000 can be used to insert and remove the distraction spacers of the '127 application to distract the intervertebral space as described in the '127, and thereafter (or during the distraction) hold to insert and remove the static trials 100/1000 to find the appropriate size of artificial intervertebral disc to be implanted.

A preferred embodiment of a dynamic trial of the present invention will now be described.

Referring now to FIGS. 51-54, a dynamic trial of the present invention is shown in top (FIG. 51), side (FIG. 52), side cutaway (FIG. 53) and perspective (FIG. 54) views.

The dynamic trial 300 is provided primarily for distracting an intervertebral space according to the procedures described herein and/or for determining the appropriate size of an artificial intervertebral disc to be implanted (or whether a particular size can be implanted) into the distracted intervertebral space. While the distraction systems and methods described in the '127 application, as well as the static trials described herein (e.g., when used in the manner that the distraction spacers of the '127 application are used), are also useful for distracting an intervertebral space, the dynamic trial 300 is provided as an additional or alternate distraction tool. Further, while the static trials described herein are useful for determining the appropriate size of an artificial intervertebral disc to be implanted (or whether a particular size can be implanted), the dynamic trial 300 is provided as an additional or alternate sizing tool.

More specifically, the dynamic trial 300 includes a shaft 302 having a bifurcated trial 304 at a distal end of the shaft 302. The trial 304 has an exterior that is preferably formed like the artificial intervertebral disc that it is meant to approximate. Accordingly, each half 306*a-b* of the bifurcated trial 304 has on its outwardly facing surface a convex dome 308*a-b* that is shaped like the convex dome of the corresponding baseplate of the artificial intervertebral disc that the dynamic trial 300 approximates (e.g., the convex domes 184*a-b* of the baseplates 168*a-b* of the artificial intervertebral disc 160 of FIGS. 13-20). Preferably, each convex dome 308*a-b* is smooth, rather than having a porous coating that is preferred for the convex domes 184*a-b* of the artificial intervertebral disc 160, and each half 306*a-b* does not have stabilizing spikes such as the stabilizing spikes 188*a-b* on the outwardly facing surfaces 186*a-b* of the artificial intervertebral disc 160. The omission of these device stabilizing and bone ingrowth encouraging structures and surfaces on the dynamic trial 300 enables the surgeon to test the size of the artificial intervertebral disc 160 to be implanted without invading the vertebral body endplates. The shaft 302 includes an inner shaft portion 310 that centrally divides at a fulcrum 311 into upper and lower distal extensions 312*a-b*. The lower distal extension 312*b* is fixed to the upper distal extension 312*a* at the fulcrum 311, preferably by screws 313*a-b* that are plug welded in place. Preferably, as shown, at least the most proximal screw 313*b* extends above the top surface of the upper distal extension 312*a* to serve as a backup stop to prevent extreme forward movement of the control knob 318 that is operated to separate the distal extensions 312*a-b* (described below).

From the point of division to their distal ends, each of the upper and lower distal extensions 312*a-b* are spring biased (preferably by the formation of the fulcrum 311 in combination with the strength of the material of which the extensions 312*a-b* are made, although the use of other types of springs is contemplated by the present invention) toward positions in which they converge toward one another (in the figures, the extensions 312*a-b* are shown in these positions). The lower distal extension 312*b* is connected (preferably fixed as shown) to the lower half 306*b* of the bifurcated trial 304, and the upper distal extension 312*a* is connected to the upper half 306*a* of the bifurcated trial 304. Preferably, as shown, the upper half 306*a* is adjustably connected to the upper distal extension 312*a* by a pivot pin 315 that allows the upper half 306*a* to rotate about a lateral axis that passes through the longitudinal and lateral center of the bifurcated trial 304. This axis of rotation allows the upper half 306*a*, when separating from the lower half 306*b*, to adjust to the orientation of the upper (adjacent) vertebral bone without causing the bone to hinge relative to the lower vertebral bone (the bone adjacent the lower half 306*b*).

In order to effect the separation of the upper and lower halves 306*a-b*, the shaft 302 further includes an outer shaft potion 314 that is longitudinally translatable adjacent the inner shaft portion 310. The outer shaft portion 314 preferably straddles the inner shaft portion 310 as shown, and includes a pin 316 that passes between the distal extensions 312*a-b*. The outer shaft portion 314 is preferably translatable distally by the forward movement of a control knob 318 near the proximal end of the shaft 302, and translatable proximally by backward movement of the control knob 318. That is, when the control knob 318 is pushed distally, the outer shaft portion 314 is moves distally, and accordingly the pin 316 moves distally. If the pushing force is great enough to overcome the bias of the divided extensions 312*a-b* (their bias toward one another), the divided extensions 312*a-b* will separate as the pin 316 moves between them (to make room for the pin 316). The separation of the extensions 312*a-b* will correspondingly separate the halves 306*a-b* of the bifurcated trial 304. It should be understood that preferably, if the control knob 318 is released, the bias of the divided extensions 312*a-b* will press against the pin 316, causing the pin 316 (and correspondingly the outer shaft portion 314 and the control knob 318) to move proximally to allow the divided extensions 312*a-b* to return to their biased position, which will bring the halves 306*a-b* of the trial 304 back together so they can be removed from the intervertebral space. Preferably, markings 320 are provided on the inner shaft portion 310 (preferably on its top surface so that the surgeon can more easily see the markings 320) to quantify the depth (to which the bifurcated trial 304 is expanded)

corresponding to the distance that the outer shaft portion 314 is translated with respect to the inner shaft portion 310.

It is anticipated that the pushing force required to separate the halves 306*a-b* will increase as they separate, due to the compression of the spine seeking to close the intervertebral space and the annulus seeking to prevent the adjacent vertebral discs from separating beyond a certain point. Therefore, to provide a mechanical advantage to the operator in the event that greater distraction is required, but the operator cannot push the control knob 318 farther with unaided human effort, an fine control knob 322 is provided. The fine control knob 322 is preferably threaded onto the proximal end of the inner shaft portion 310, proximal to the control knob 318. Thus, rotation of the fine control knob 322 about the longitudinal axis of the inner shaft portion 310 will cause the body of the fine control knob 322 to press against the control knob 318 to move it farther distally. The interference of the threads of the fine control knob-inner shaft portion interface prevents the fine control knob 322 from backing up proximally unless the fine control knob 322 is reverse rotated to effect that result.

Preferably, as shown, the proximal end 324 of the shaft 302 is preferably flanged to serve as a slap hammer for impaction (by hitting the proximal end 324 with a mallet with a distally directed force, e.g.), if necessary for proper positioning of the bifurcated trial 304, and/or forced extraction of the bifurcated trial 304 (by hitting the flange of the proximal end 324 with a mallet with a proximally directed force, e.g.).

Accordingly, the dynamic trial 300 can be used as an additional or alternative distracting tool (e.g., to the distraction spacers), and/or as an alternative or additional sizing tool (e.g., to the static trials). As an example of a use for the dynamic trial 300 as an alternative or additional distraction tool and an alterative sizing tool, once the intervertebral space is distracted to (or, without distraction, is at) a depth that is at least equal to the depth of the closed bifurcated trial 304, the bifurcated trial 304 of the dynamic trial 300 can be inserted into the intervertebral space. (If the intervertebral space must be distracted initially because it starts out more shallow than the depth of the closed bifurcated trial 304, the distraction spacers of the '127 application and the methods disclosed therein can be used, e.g.) The control knob 318 and/or fine control knob 322 can be operated to separate the halves 306*a-b* of the bifurcated trial 304 to distract the space as clinically appropriate. Because the bifurcated trial 304 is shaped externally to approximate the artificial intervertebral disc to be implanted (e.g., the artificial intervertebral disc 160), and because the pivoting of the upper half 306*a* of the bifurcated trial 304 allows the halves 306*a-b* to appropriately lordotically orient themselves, when the surgeon determines the intervertebral space to be distracted to its proper dimension (based on how much compression is being experienced on the dynamic trial 300 and how tight the annulus is), he can read the markings 320 on the shaft 302 to determine what size of artificial intervertebral disc 160 is suitable for the dimensioned intervertebral space. A subsequent bringing together of the halves 306*a-b* and a removal of the dynamic trial 300 can then be followed by insertion of the appropriately sized artificial intervertebral disc 160 (e.g., in manners described below with regard to the inserter/impactors).

As an example of a use for the dynamic trial 300 as an alternative distraction tool and an additional sizing tool, after the surgeon has initially distracted the intervertebral space (preferably with the distraction spacers of the '127 application or the static trials described herein), and applied one or more of the static trials 100,1000 to the intervertebral space to determine the appropriate size of the artificial intervertebral disc to be implanted (e.g., the artificial intervertebral disc 160), the surgeon can apply the dynamic trial 300, expand it to the size of the static trial 100,1000 that was determined to be the appropriate size for the intervertebral space, and then further open the dynamic trial 300 for a final sizing. An example of a final sizing that would be useful would be to test the amount of farther distraction that is clinically possible, without having to remove and replace static trials 100,1000 when the compression force of the spine and the tension force of the annulus are at their higher levels. Also, the surgeon may wish to distract the space slightly more than the size of the appropriately sized static trial 100,1000 or artificial intervertebral disc 160, so that the artificial intervertebral disc 160 can be more easily inserted after removal of the static 100,1000 or dynamic trial 300 results in a compressive settling of the intervertebral space. The surgeon may also wish to distract the space slightly more than the size of the appropriately sized static trial 100,1000 or artificial intervertebral disc 160, to prepare it for easy insertion of the artificial intervertebral disc 160 to be implanted, with consideration for the height of the stabilizing spikes 188*a-b* on the outwardly facing surfaces 186*a-b* of the baseplates 168*a-b* of the artificial intervertebral disc 160. While the artificial intervertebral disc 160 having the spikes 188*a-b* can be implanted without the additional distraction, some surgeons may find such additional distraction useful or desirable for a particular case.

Preferred embodiments of inserter/impactors of the present invention will now be described.

Referring now to FIGS. 55-58, an inserter/impactor of the present invention is shown in side (FIG. 55), top (FIG. 56), side cutaway (FIG. 57) and perspective (FIG. 58) views. FIGS. 59-62 show side (FIG. 59), top (FIG. 60), side cutaway (FIG. 61), and perspective (FIG. 62) views of an inserter/impactor of the present invention holding a static trial of the present invention. FIGS. 63-64 show top views of an inserter/impactor of the present invention holding a static trial of the present invention in two alternative ways. FIGS. 65-68 show side (FIG. 65), top (FIG. 66), side cutaway (FIG. 67), and perspective (FIG. 68) views of an inserter/impactor of the present invention holding an exemplary artificial intervertebral disc of the present invention. FIGS. 69-70 show top views of an inserter/impactor of the present invention holding an exemplary artificial intervertebral disc of the present invention in two alternative ways.

Figure 78:
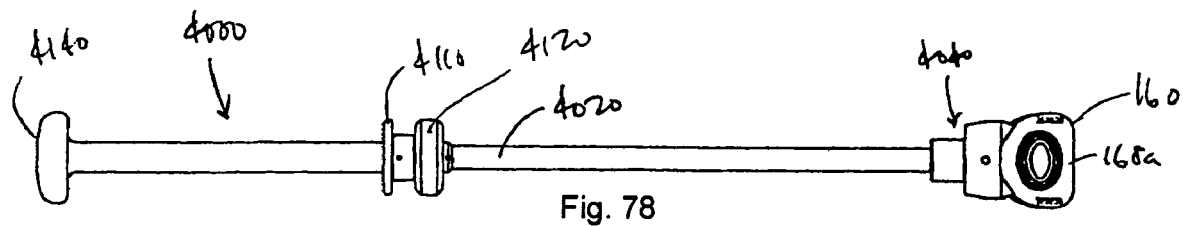
FIGS. 78-79 show top (FIG. 78) and side (FIG. 79) views of a wedge plate inserter/impactor of the present invention holding an exemplary artificial intervertebral disc.
Figure 79:
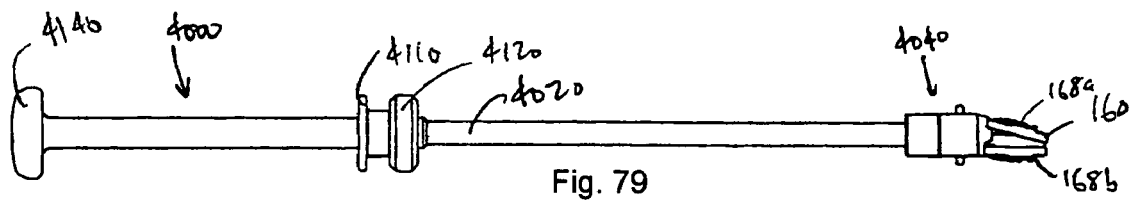
Figure 80:
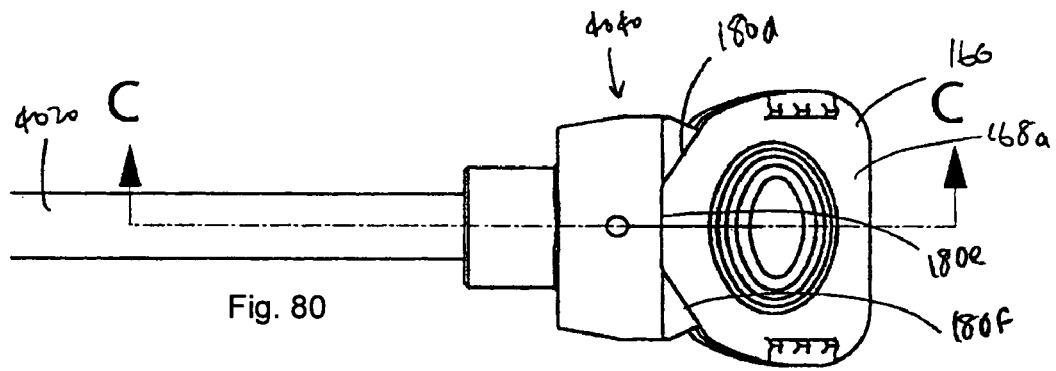
FIGS. 80-82 show top (FIG. 80), side (FIG. 81), and side cutaway (FIG. 82) views of a distal end of a wedge plate inserter/impactor of the present invention holding an exemplary artificial intervertebral disc.
Figure 81:
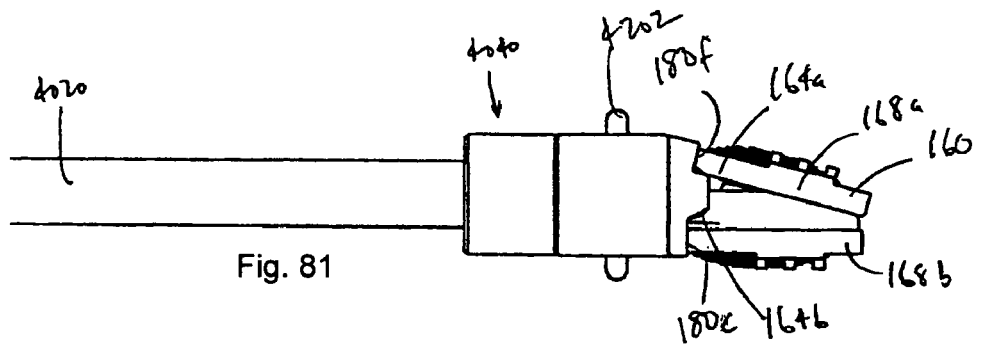
Figure 82:
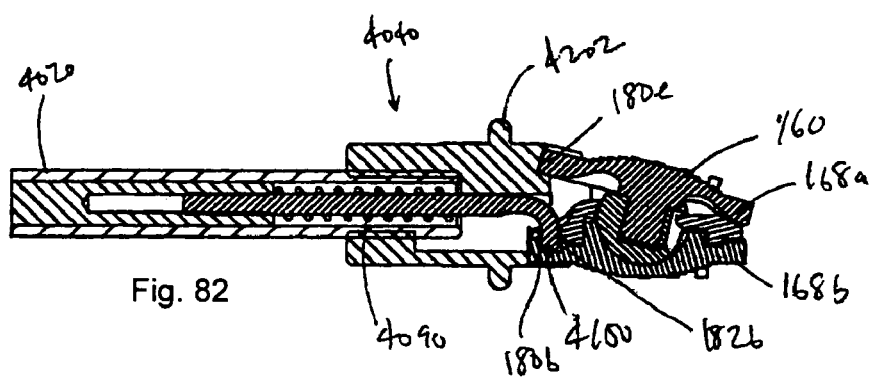

Referring now to FIGS. 71-82, side (FIG. 71), perspective (FIG. 72), and close-up perspective (FIG. 73) views of a wedge plate inserter/impactor of the present invention. FIGS. 74-77 show bottom (FIG. 74), side (FIG. 75), top (FIG. 76), and side cutaway (FIG. 77) views of a distal end of a wedge plate inserter/impactor of the present invention. FIGS. 78-79 show top (FIG. 78) and side (FIG. 79) views of a wedge plate inserter/impactor of the present invention holding an exemplary artificial intervertebral disc. FIGS. 80-82 show top (FIG. 80), side (FIG. 81), and side cutaway (FIG. 82) views of a distal end of a wedge plate inserter/impactor of the present invention holding an exemplary artificial intervertebral disc.

Each inserter/impactor 400,4000 is provided primarily for holding, inserting, repositioning, removing, impacting, extracting, and otherwise manipulating an artificial intervertebral disc having features suitable for being manipulated by the inserter/impactor. (However, they can also be used to hold, insert, reposition, remove, impact, extract, and otherwise manipulate the static trials 100,1000 as described above, as well as any other orthopedic device having suitable features therefor. For example, it should be understood that distraction of an intervertebral space can be accomplished in conjunction with a cooperating tool or spacer that can be gripped by the inserter/impactor.) Exemplary suitable artificial intervertebral discs include, but are not limited to, the artificial intervertebral disc 160 described herein and the artificial intervertebral discs described in the '160 and '528 applications with regard to FIGS. 8a-z, 9a-u, 10a-u, 11a-k, and 12a-p thereof and b accompanying descriptions therefor (e.g., embodiments identified as the first, second, third, fourth, and fifth preferred embodiments of the fourth embodiment family, etc.). Regarding the features suitable for being manipulated by the inserter/impactor 400,4000, such features include those discussed above as being suitable features on the static trials 100,1000 and disc 160, namely, an anteriorly facing flat surface on the second (e.g., lower) baseplate of the trial or disc, flanked by two anteriolaterally facing flat surfaces (one on each side of the anteriorly facing flat surface), and, to provide for holding of the trial or disc for an anterior insertion approach, a hole spaced from the anteriorly facing flat surface, the hole having a longitudinal axis parallel to the anteriorly facing flat surface. Further regarding the features suitable for being manipulated by the wedge plate inserter/impactor 4000, such features further include the inwardly facing surfaces of the baseplates of the trial or disc.

More particularly, the inserter/impactor 400,4000 includes a shaft 402,4020 having a distal end 404,4040 that has angled flat surfaces 420*a-c*,4200*a-f* corresponding to and fittable against angled flat surfaces of the static trial (e.g., the surfaces 120*a-f*,1200*a-f* of the static trial 100,1000) or artificial intervertebral disc (e.g., the surfaces 180*a-f* of the artificial intervertebral disc 160) to be implanted. For example, in an anterior approach for the trial 100,1000 (as shown in FIGS. 59-62 as an example of how either static trial 100,10000 can be engaged by either inserter/impactor 400,4000), 120*a*,1200*a* and 120*d*,1200*d* facing 420*a* (or 4200*a* and 4200*d*), 120*b*,1200*b* and 120*e*,1200*e* facing 420*b* (or 4200*b* and 4200*e*), and 120*c*,1200*c* and 120*f*,1200*f* facing 420*c* (or 4200*c* and 4200*f*, and in an anterior approach for the disc 160 (as shown in FIGS. 65-68 as an example of how the disc 160 can be engaged by either inserter/impactor 400,4000), 180*a* and 180*d* facing 420*a* (or 4200*a* and 4200*d*), 180*b* and 180*e* facing 420*b* (or 4200*b* and 4200*e*), and 180*c* and 180*f* facing 420*c* (4200*c* and 4200*f*. Additionally with regard to the wedge plate inserter/impactor 4000, the distal end 4040 has a wedge-shaped extension 4042 including upper 4200*g* and lower 4200*h* wedge surfaces corresponding to and fittable against the inwardly facing surfaces of the artificial intervertebral disc (e.g., the lower surface 164*a* of the upper baseplate 168*a* of the disc 160, and the upper surface 164*b* of the lower baseplate 168*b* of the disc 160, respectively) to be implanted, causing the baseplates to be angled at a 15 degree lordosis angle, with the lower surface 164*a* of the upper baseplate 168*a* held against the upper surface 4200*g*, and the upper surface of the shield being held against the lower surface 4200*h*, as best shown in FIGS. 78-82

In particular with regard to the wedge plate inserter/impactor 4000, the inserter/impactor 4000 holds the disc 160 in a preferred position with respect to the inserter/impactor 4000. (It should be understood that the surfaces of the wedge-shaped extension 4042 can be modified within the scope of the present invention to hold the disc 160 (or another orthopedic device) at positions other than those illustrated herein.) In the illustrated embodiment of the inserter/impactor 4000 in use with the disc 160, the preferred position is with the baseplates 168*a,b* of the disc 160 angle at 15 degrees of lordosis with respect to one another. More particularly, as best shown in FIGS. 78-82, preferably, the upper and lower surfaces (e.g., 4200*g* and 4200*h*) of the wedge-shaped extension 4042 protrude from the distal end 4040 and are formed to hold the baseplates 168*a,b* such that they are angled at 15 degrees of lordosis with respect to one another. A surface (e.g., lower surface 4200*h*) of the wedge-shape extension 4042 that mates with an inwardly facing surface of a baseplate (e.g., the lower baseplate 168*b*) of a disc (e.g., 160) may be correspondingly shaped (e.g., curved or flat) for interaction or mating with the disc baseplate (e.g., the lower surface 4200*h* of the wedge-shaped extension as illustrated is curved to accommodate the surface of the shield of the disc). Preferably, the forward surface 4200*i* of the wedge-shaped extension 4042 has a concave curvature towards the shaft 4020 of the inserter/impactor 4000, also for accommodating the curvature of the surface of the shield of the disc.

Also preferably with regard to the wedge plate inserter/impactor 4000 and this preferred postioning, the wedge surfaces of the distal end 4040 protrude from a distance midway with respect to the top and bottom of the distal end 4040 and span (e.g., right to left or vice-versa) the entire distal face of the distal end 4040, and the surfaces 4200*d-f* above the wedge on the distal end 4040 are respectively perpendicular to the wedge's upper surface 4200*g* such that each is disposed in parallel with its respective corresponding surface of the disc 160 when the disc 160 is held by the inserter/impactor 4000 at the appropriate lordosis angle. (And, accordingly, are angled approximately 15 degrees with respect to the surfaces below the wedge 4200*a-c*.) Preferably, for an anterior approach, the wedge-shaped extension 4042 is designed and shaped to fit with its antero-lateral confronting surfaces (4200*d,f* and 4200*a,c*) tightly against the correspondingly antero-laterally facing surfaces (180*d,f* and 180*a,c*) of the disc 160, but such that its anterior confronting surfaces (4200*e* and 4200*b*) are slightly spaced from the anteriorly facing surfaces (180*d* and 180*b*) of the disc 160, when the disc is held by the inserter/impactor 4000. This is primarily to address manufacturing issues (in some instances, tolerances may not be adequately defined to ensure that all of those surfaces fit tightly against their corresponding surfaces), so that if there are manufacturing anomalies, any slight tolerance differences that may exist are nevertheless still adequate to ensure at least the tight fitting of the antero-lateral confronting surfaces, so that manipulation of the disc 160 is possible (e.g., in the manner of a wrench against an angled nut). This can be achieved, e.g., by designing the anterior confronting surfaces (4200*e* and 4200*b*) to each be slightly greater in length than the corresponding anteriorly facing surfaces (180*e* and 180*b*) of the disc baseplates, while still being angled with respect to the antero-lateral confronting surfaces (4200*d,f* and 4200*a,c*) at the same angle the antero-laterally facing surfaces (180*d,f* and 180*a,c*) of the disc baseplates are angled with respect to the anteriorly facing surfaces (180*e* and 180*b*) of the disc. The increased length of the anterior confronting surfaces on the wedge extension results in the slight clearance between the anteriorly facing surfaces (180*e* and 180*b*) of the disc and the corresponding anterior confronting surface (4200*e* and 4200*b*) of the wedged distal end, thereby ensuring that the disc will be fully seated against the antero-lateral confronting surfaces of the distal end despite possible manufacturing, material or other inevitable variations in tolerances of the artificial intervertebral disc or the inserter/ impactor. As noted above, similar in this regard to the manner in which a wrench engages a nut, this fitting increases the mechanical advantage toward repositioning the disc in the intervertebral space. It should be noted, inasmuch as the inserter/impactor 4000 described herein can engage the disc from the antero-lateral angles as well, the anterior confronting surfaces (4200e and 4200b) should also be longer than the antero-laterally facing surfaces (180d,f and 180a,c) of the disc, so that a similar fitting occurs when the disc is held from the antero-lateral angles. Stated broadly, the primary confronting surfaces (e.g., the anterior confronting surfaces) of the inserter/impactor are preferably slightly longer than the primary confronted surfaces(e.g., anteriorly facing surfaces) of the disc for any given holding orientation.

Each inserter/impactor 400,4000 includes a holding pin 408,4080 that extends from the center flat surface 420b, 4200b along a longitudinal axis of the shaft 402,4020, the pin 408,4080 having a distal end 410,4100 that is bent downwardly. The holding pin 408,4080 is spring loaded (by a spring 409,4090) in a central channel of the shaft 402, 4020, so that it is biased toward and against the shaft 402,4020 (preferably, the bent end 410,4100 of the pin 408,4080 prevents it from entering the central channel). With regard to the wedge plate inserter/impactor 4000, the holding pin 4080 is restricted from upwardly lateral movement with respect to the distal end of the inserter/impactor 4000 by the presence of the wedge-shaped extension 4042 of the distal end 4040 of the inserter/impactor 4000. More particularly, with any attempted upward movement of the holding pin 4080, the pin encounters the upper surface of the channel in which the pin 4080 travels, preventing any such upward movement. On both inserter/impactors 400,4000, the holding pin 408,4080 is preferably heat treated (e.g., cold formed) to increase material quality (e.g., strength).

A flange 411,4110, mechanically connected to the pin 408,4080 and translating adjacent the shaft 402,4020, can be pushed distally to overcome the bias of the spring 409,4090 to space the pin 408,4080 away from the central flat surface 420b,4200b. (An alternative configuration is one in which the flange 411,4110 and the pin 408,4080 are formed from a single piece, rather than being mechanically connected.) In this extended position, the pin 408,4080 can be inserted in the hole 122b,1220b,182b in the base plate 108b,1080b, 168b of the static trial 100,1000 or artificial intervertebral disc 160. Releasing the flange 411,4110 allows the spring 409,490 to pull the pin 408,4080 back, causing the anteriorly facing surface 120b,1200b,180b of the baseplate 108b, 1080b,168b to be held against the central flat surface 420b of the inserter/impactor 400 (or against the lower central flat surface 420b of the inserter/impactor 4000) and the anterioloaterally facing flat surfaces 128a,c,1200a,c,180a,c of the static trial 100,1000 or artificial intervertebral disc 160 to be held against the other corresponding flat surfaces 420a,c of the inserter/impactor 400 (or against the other corresponding flat surfaces 4200a,c of the inserter/impactor 4000). Further and simultaneously, with regard to the wedge plate inserter/impactor 4000, the anteriorly facing surface 180e of the baseplate 168a is pulled against the upper central flat surfaces 4200e of the inserter/impactor 4000 and the anterioloaterally facing flat surfaces 180d,f of the artificial intervertebral disc 160 is pulled against the other corresponding flat surfaces 4200d,f of the inserter/impactor 4000. Additionally with regard to the wedge plate inserter/impactor 4000, as noted above, the upper and lower wedge surfaces (4200g,h) interfere between inwardly facing surfaces 164a,b of the disc baseplates causing the baseplates to be angled at a 15 degree lordosis angle, with the lower surface 164a of the upper baseplate 168a held against the upper surface 4200g, and the upper surfaces of the shield being held against the lower surface 4200h, as best shown in FIGS. 78-82.

A knob 412,4120, threaded on the shaft 402,4020, can be rotated about the longitudinal axis of the shaft 402,4020 to push the flange 411,4110 farther proximally, to pull the pin 409,4090 tighter and therefore lock its position (the interference of the threads of the knob-shaft interface prevents the knob 412,4120 from moving distally unless the knob 412,4120 is reverse rotated to effect that result) to more securely hold the baseplate 108b,1080b,168b, and reverse rotated to unlock and loosen the pin 409,4090.

When the static trial 100,1000 or disc 160 is held in this manner, rotation of the static trial 100,1000 or disc 160 about a longitudinal axis (of the static trial 100,1000 or disc 160) relative to the inserter/impactor 400,4000 is prevented by interference of the corners of the static trial's 100,1000 or disc's 160 flat surfaces 120a-c,1200a-c,180a-c and the corners of the inserter/impactor's 400,4000 flat surfaces 420a,4200a-f, similar to the manner in which a wrench holding a nut prevents rotation of the nut relative to the wrench. Further, the holding of the static trial 100,1000 or disc 160 in this manner allows for some repositioning of the static trial 100,1000 or disc 160 in the intervertebral space via rotation of the static trial 100,1000 or disc 160 in either direction about the longitudinal axis of the intervertebral space.

Further, with regard to the wedge plate inserter/impactor 4000, when the static trial 100,1000 or disc 160 is held in this manner, rotation of the static trial 100,1000 or disc 160 about a lateral axis (of the static trial 100,1000 or disc 160) relative to the inserter/impactor 4000 is prevented by interference of the inwardly facing surface (e.g., 164a) of the first baseplate (e.g., upper baseplate) of the static trial 100,1000 or disc 160 and the upper surface 4200g of the wedge on the distal end 4040, and by interference of the inwardly facing surface (e.g., 164b) of the second baseplate (e.g., lower baseplate) of the static trial 100,1000 or disc 160 and the lower surface 4200h of the wedge on the distal end 4040. Accordingly, the holding of the static trial 100,1000 or disc 160 in this manner allows for some repositioning of the static trial 100,1000 or disc 160 in the intervertebral space via rotation of the static trial 100,1000 or disc 160 in either direction about the longitudinal or latitudinal axis of the intervertebral space.

In some embodiments of the wedge plate inserter/impactor 4000, when the artificial intervertebral disc 160 is held by the inserter/impactor 4000, the flat surfaces 180a are more closely confronted by the angled flat surfaces 4200a-c of the inserter/impactor 4000, compared with the flat surfaces 180d-f being less closely confronted by the angled flat surfaces 4200d-f of the inserter/impactor 4000. As such, the structure of the artificial intervertebral disc 160 having the flat surfaces 180d-f (e.g., the upper baseplate 168a) has slightly more rotation and angulation freedom relative to the inserter/impactor 4000 when being held, compared to the structure of the artificial intervertebral disc 160 having the flat surfaces 180a-c (e.g., the lower baseplate 168b). This permits the artificial intervertebral disc 160 to adjust to the intervertebral space (e.g., to the angulation of the adjacent vertebral endplates, defining the intervertebral space, relative to one another) as it is being inserted thereinto. That is, typically, the adjacent vertebral endplates will be lordotically angled with respect to one another as a result of the intervertebral space being prepared and distracted.

Preferably, both of the baseplates of the static trial 100, 1000 or disc 160 have similarly configured flat surfaces. For example, the lower baseplate's 108b,1080b,168b flat surfaces 120a-c,1200a-c,180a-c have similarly configured and similarly oriented counterpart flat surfaces 120d-f,1200d-f, 180d-f on the upper baseplate 108a,1080a,168a. Further preferably, both baseplates' 108a-b,1080a-b,168a-b flat surfaces 120a-f,1200a face the angled flat surfaces 420a-c, 4200a-f of the inserter/impactor 400,4000 when the static trial 100,1000 or disc 160 is held by the inserter/impactor 400,4000. For example, in an anterior approach for the trial 100,1000 (as shown in FIGS. 59-62 as an example of how either trial 100,1000 can be held by either inserter/impactor 400,4000), 120a,1200a and 120d,1200d facing 420a (or 4200a and 4200d), 120b,1200b and 120e,1200e facing 420b (or 4200b and 4200e), and 120c,1200c and 120f,1200f facing 420c (or 4200c and 4200f), and in an anterior approach for the disc 160 (as shown in FIGS. 65-68), 180a and 180d facing 420a (or 4200a and 4200d), 180b and 180e facing 420b (or 4200b and 4200e), and 180c and 180f facing 420c (or 4200c and 4200f).

It should be noted that preferably, when the static trial 100,1000 is held by the inserter/impactor 400,4000, the flat surfaces 120a-c,1200a-c and the counterpart flat surfaces 120d-f,1200d-f are tightly held against the angled flat surfaces 420a-c,4200a-f of the inserter/impactor 400,4000 as described above. It is also preferable that the baseplates 108a-b,1080a-b of each of the plurality of static trials 100,1000 be appropriately lordotically angled relative to one another to ease insertion of the static trial 100,1000 into the intervertebral space and to mimic how the artificial intervertebral disc 160 will typically be oriented as it is being inserted using the inserter/impactor 400,4000. While not shown in FIGS. 1-6 or FIGS. 7-12, in some embodiments, when the static trials 100,1000 are formed in such a lordotically oriented configuration, it is preferable that the flat surfaces 120d-f,1200d-f on the first (e.g., upper) baseplate 108a,1080a be parallel to the flat surfaces 120a-c,1200a-c of the second (e.g., lower) baseplate 108b,1080b in the static trial's 100,1000 appropriately lordotically oriented configuration, so that when the static trial 100,1000 is held tightly by the inserter/impactor 400,4000, the flat surfaces 120a-f, 1200a-f are flush with the flat surfaces 420a-c,4200a-f of the inserter/impactor 400,4000 even though the baseplates 108a-b,1080a-b are lordotically oriented configuration, it is preferable that the flat surfaces 120d-f,1200d-f on the first (e.g., upper baseplate 108a,1080a be parallet to the flat surfaces 120a-c,1200a-c of the second (e.g., lower) base plate 108b,1080b in the static trial's 1000,1000 appropriately lordotically oreiented configuration, so that when the static trial 100,1000 is held tightly by the inserter/inpactor 400,4000, the flat surfaces 120a-f,1200a-f are flush with the flat surfaces 420a-c,4200a-f of the inserter/impactor 400, 4000 even though the baseplates 108a-b,1080a-b are lordotically angled with respect to one another.

With regard to the inserter/impactor 400, by contrast, preferably, when the artificial intervertebral disc 160 is held by the inserter/impactor 400, the flat surfaces 180a-c are tightly held against the angled flat surfaces 420a-c of the inserter/impactor 400 as described above, but the counterpart flat surfaces 180d-f are loosely held against the angled flat surfaces 420a-c of the inserter/impactor 400. As such, the structure of the artificial intervertebral disc 160 having the counterpart flat surfaces 180d-f (e.g., the upper baseplate 168a) is able to angulate and rotate to a limited extent relative to the structure of the artificial intervertebral disc 160 having the flat surfaces 180a-c. This permits the artificial intervertebral disc 160 to adjust to the intervertebral space (e.g., to the angulation of the adjacent vertebral endplates, defining the intervertebral space, relative to one another) as it is being inserted thereinto. That is, typically, the adjacent vertebral endplates will be lordotically angled with respect to one another as a result of the intervertebral space being prepared and distracted. As the artificial intervertebral disc 160 is then inserted into the intervertebral space using the inserter/impactor 400, then, the baseplates 168a-b will be permitted to lordotically angle with respect to one another to squeeze into the intervertebral space.

With regard to the wedge plate inserter/impactor 4000, when the artificial intervertebral disc 160 is held by the inserter/impactor 4000, the wedge surfaces of the distal end 4040 protrude from a distance midway with respect to the top and bottom of the distal end 4040 and span (e.g., right to left or vice-versa) the entire distal face of the distal end 4040, and the surfaces 4200d-f above the wedge on the distal end 4040 are respectively perpendicular to the wedge's upper surface 4200g such that each is disposed in parallel with its respective corresponding surface of the disc 160 when the disc 160 is held by the inserter/impactor 4000 at the appropriate lordosis angle. (And, accordingly, are angled approximately 15 degrees with respect to the surfaces below the wedge 4200a-c.) Preferably, for an anterior approach, the wedge-shaped extension 4042 is designed and shaped to fit with its antero-lateral confronting surfaces (4200d,f and 4200a,c) tightly against the correspondingly antero-laterally facing surfaces (180d,f and 180a,c) of the disc 160, but such that its anterior confronting surfaces (4200e and 4200b) are slightly spaced from the anteriorly facing surfaces (180d and 180b) of the disc 160, when the disc is held by the inserter/ impactor 4000. This is primarily to address manufacturing issues (in some instances, tolerances may not be adequately defined to ensure that all of those surfaces fit tightly against their corresponding surfaces), so that if there are manufacturing anomalies, any slight tolerance differences that may exist are nevertheless still adequate to ensure at least the tight fitting of the antero-lateral confronting surfaces, so that manipulation of the disc 160 is possible (e.g., in the manner of a wrench against an angled nut). This can be achieved, e.g., by designing the anterior confronting surfaces (4200e and 4200b) to each be slightly greater in length than the corresponding anteriorly facing surfaces (180e and 180b) of the disc baseplates, while still being angled with respect to the antero-lateral confronting surfaces (4200d,f and 4200a, c) at the same angle the antero-laterally facing surfaces (180d,f and 180a,c) of the disc baseplates are angled with respect to the anteriorly facing surfaces (180e and 180b) of the disc. The increased length of the anterior confronting surfaces on the wedge extension results in the slight clearance between the anteriorly facing surfaces (180e and 180b) of the disc and the corresponding anterior confronting surface (4200e and 4200b) of the wedged distal end, thereby ensuring that the disc will be fully seated against the antero-lateral confronting surfaces of the distal end despite possible manufacturing, material or other inevitable variations in tolerances of the artificial intervertebral disc or the inserter/impactor. As noted above, similar in this regard to the manner in which a wrench engages a nut, this fitting increases the mechanical advantage toward repositioning the disc in the intervertebral space. It should be noted, inasmuch as the inserter/impactor 4000 described herein can engage the disc from the antero-lateral angles as well, the anterior confronting surfaces (4200e and 4200b) should also be longer than the antero-laterally facing surfaces (180d,f and 180a,c) of the disc, so that a similar fitting occurs when the disc is held from the antero-lateral angles. Stated broadly, the primary confronting surfaces (e.g., the anterior confronting surfaces) of the inserter/impactor are preferably slightly longer than the primary confronted surfaces (e.g., anteriorly facing surfaces) of the disc for any given holding orientation.

Also preferably, in order to provide for a holding of the static trial 100,1000 or disc 160 for two additional (here, anteriolateral) insertion approaches, each static trial 100, 1000 or disc 160 also includes two additional holes 122a, 1220a,182a and 122c,1220c,182c, one (e.g., 122a,1220a, 182a) spaced apart from one of the anteriolaterally facing flat surfaces (e.g., 120a,1200a,180a), and the other (e.g., 122c,1220c,182c) spaced apart from the other of the anteriolaterally facing flat surfaces (e.g., 120c,1200c,180c). Accordingly, operation of the inserter/impactor 400,4000 can fit the holding pin 408,4080 into either of these two additional holes 122a,1220a,182a or 122c,1220c,182c, and hold the associated anteriolaterally facing flat surface (the one associated with the hole into which the pin 408,4080 is fit) of the static trial 100,1000 or disc 160 against the flat surface of the inserter/impactor 400,4000 opposite the pin 408,4080. For example, in a first anteriolateral approach for the trial 0.100,1000 (as shown in FIG. 63 as an example of how either trial 100,1000 can be engaged by either inserter/impactor 400,4000), 120a,1200a and 120d,1200d not confronted, 120b,1200b and 120e,1200e facing 420a (or 4200a and 4200d), and 120c,1200c and 120f,1200f facing 420 (or 4200b and 4200e), and a first anteriolateral approach for the disc 160 (as shown in FIG. 69 as an example of the how the disc 160 can be engaged by either inserter/impactor 400, 4000), 180a and 180d not confronted, 180b and 180e facing 420a (or 4200a and 4200d), and 180c and 180f facing 420b (or 4200b and 4200e). And, for example, in a second anteriolateral approach for the trial 100 (as shown in FIG. 64 as an example of how either trial 100,1000 can be engaged by either inserter/impactor 400,4000), 120a,1200a and 120d,1200d facing 420b (or 4200b and 4200e), 120b,1200b and 120e,1200e facing 420c (or 4200c and 4200f), and 120c,1200c and 120f,1200f not confronted, and a second anteriolateral approach for the disc 160 (as shown in FIG. 70 as an example of how the disc 160 can be engaged by either inserter/impactor 400,4000), 180a and 180d facing 420b (or 4200b and 4200e), 180b and 180e facing 420c (or 4200c and 4200f), and 180c and 180f not confronted.

It should be understood that preferably, in order to facilitate these additional approaches, the angle separating the anteriorly facing flat surface of the static trial 100,1000 or disc 160 and one of the anteriolaterally facing flat surfaces of the static trial 100,1000 or disc 160 is equal to the angle separating the anteriorly facing flat surface and the other of the anteriolaterally facing flat surfaces. Preferably, the surfaces are angled with respect to one another at an angle of 33.4 degrees.

It should also be understood that the inclusion of additional adjacent angulated surfaces (or placing the angulated surfaces in other locations on the trial or disc or other orthopedic device), and/or including corresponding holes adjacent to such surfaces, can provide the surgeon with additional approaches, e.g., other anteriolateral approaches, directly lateral approaches, posteriolateral approaches, and/or directly posterior approaches. For example, a trial or disc can have angled surfaces (and corresponding holes) along the entire perimeter of one or both of the baseplates, and thus enable the surgeon to engage the trial or disc from a number of angles, including anterior, posterior, lateral, anteriolateral, and posteriolateral angles.

The inserter/impactor 400,4000 further includes at a proximal end a cap 414,4140 for use as an impact surface if the trial 100,1000 or disc 160 must be impacted further into the intervertebral space after insertion, or forcibly extracted from the intervertebral space. A mallet can be used to strike the cap 414,4140 (in a distal direction for impaction, or in a proximal direction (using the flange of the cap 414,4140) for extraction). It should be noted a striking of the cap 414,4140 will translate the striking force to the baseplates through the shaft 402,4020 and the flat surfaces, but will not damage the holding pin 408,4080 because the holding pin 408,4080 is spring loaded in the central channel and thus buffered from the striking force thereby. The distal end 404,4040 of the inserter/impactor 400,4000 further preferably includes at least one vertebral body stop (e.g., 4202) that protrudes longitudinally with respect to the shaft 402,4020, from the surfaces of the distal end. The stops help prevent the inserter/impactor from being used to insert the disc (or other orthopedic device) too far into the intervertebral space.

Accordingly, the inserter/impactor 400,4000 can be used to grip either the static trials or the artificial intervertebral disc to be implanted, and hold the same during insertion and/or removal of the same, and is useful for a variety of surgical approach angles.

Preferred embodiments of a repositioner/extractor of the present invention will now be described.

Figure 83:
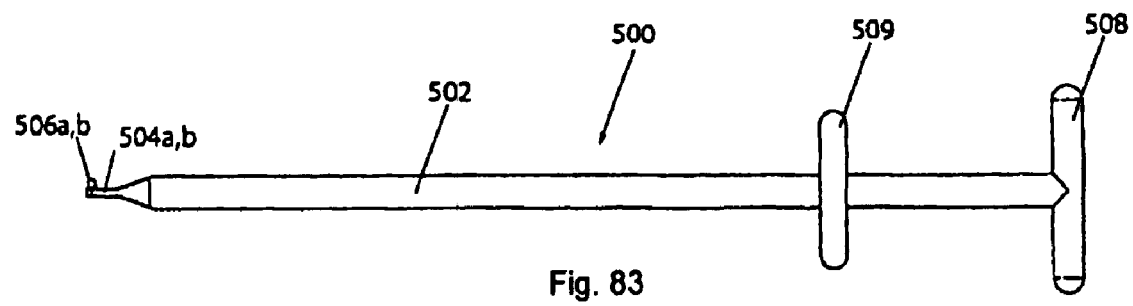
FIGS. 83-85 show side (FIG. 83), top (FIG. 84), and perspective (FIG. 85) views of a symmetric repositioner/extractor of the present invention.
Figure 84:
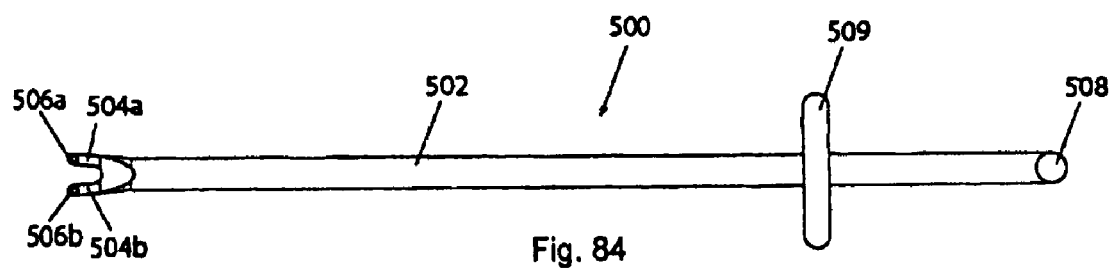
Figure 85:
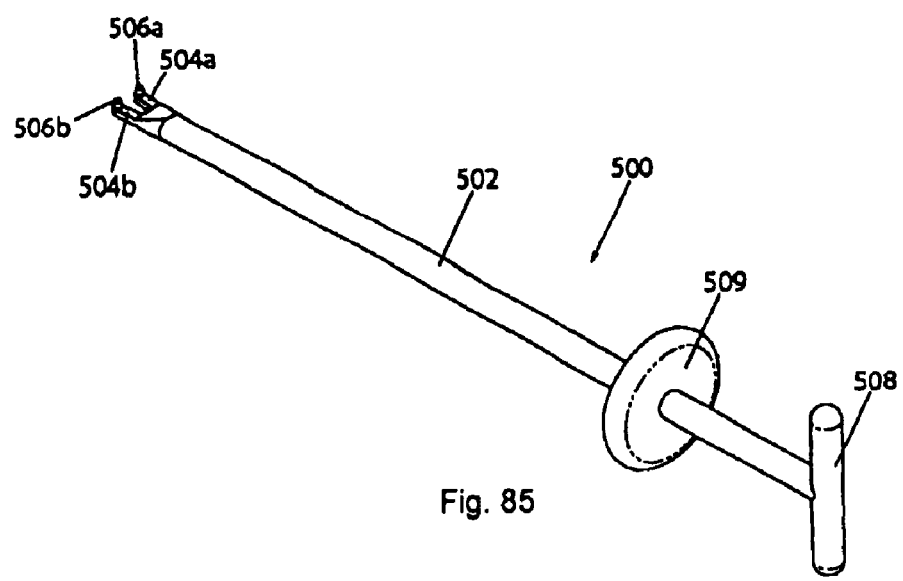
Figure 86:
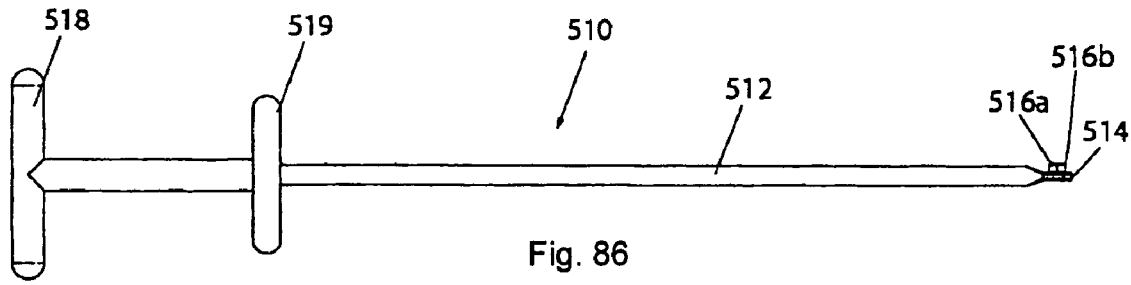
FIGS. 86-88 show side (FIG. 86), top (FIG. 87), and perspective (FIG. 88) views of an offset left repositioner/extractor of the present invention.
Figure 87:
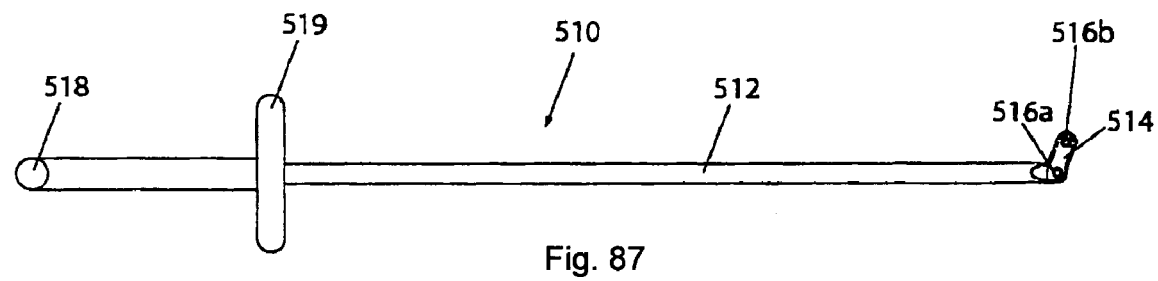
Figure 88:
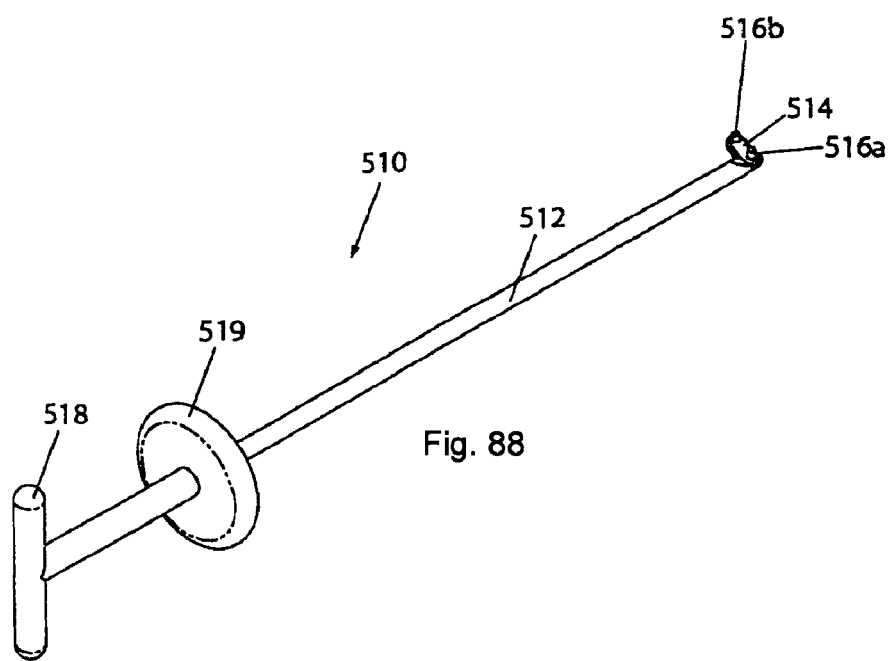
Figure 89:
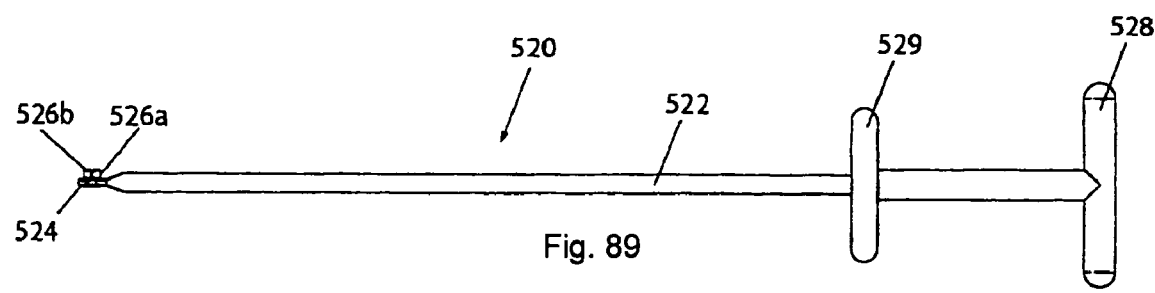
FIGS. 89-91 show side (FIG. 89), top (FIG. 90), and perspective (FIG. 91) views of an offset right repositioner/extractor of the present invention.
Figure 90:
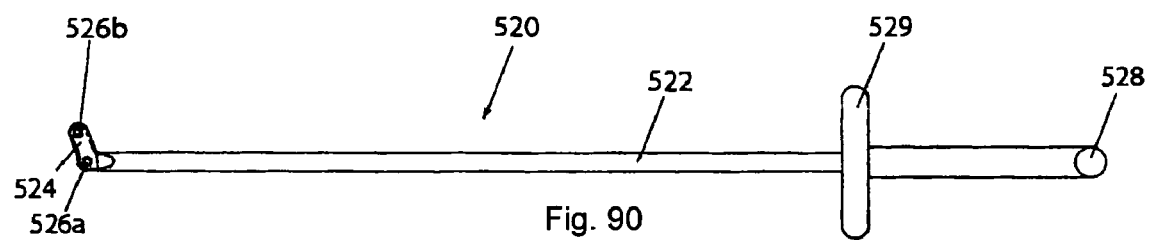
Figure 91:
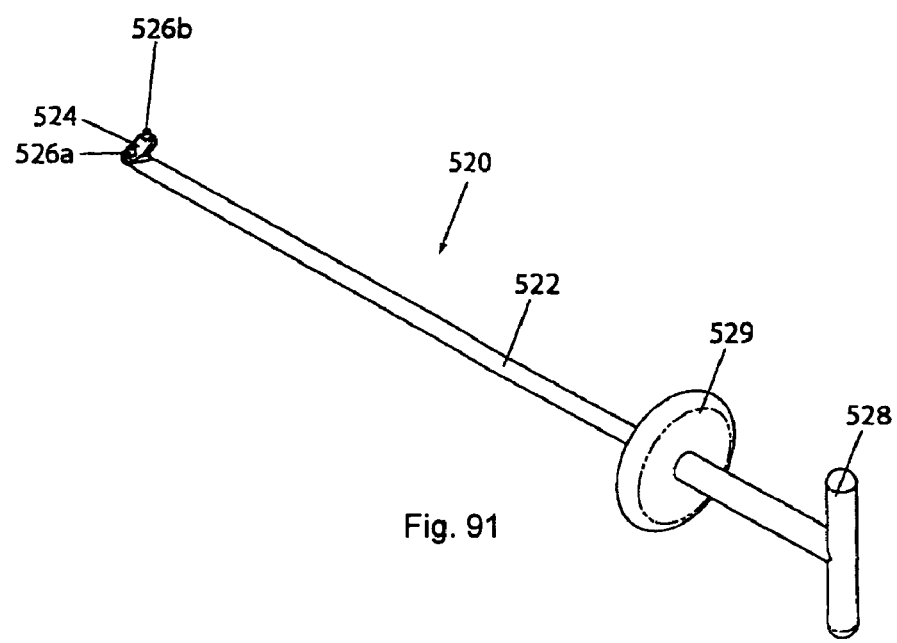
Figure 92:
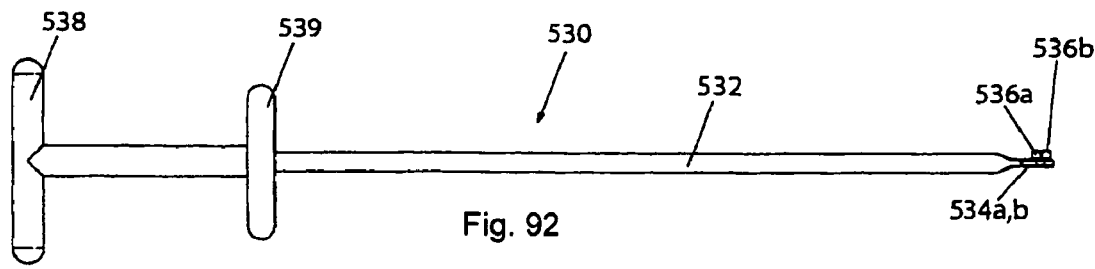
FIGS. 92-94 show side (FIG. 92), top (FIG. 93), and perspective (FIG. 94) views of an alternative offset left repositioner/extractor of the present invention.
Figure 93:
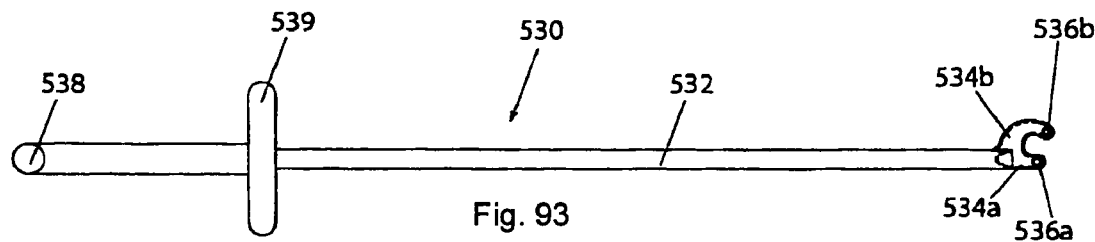
Figure 94:
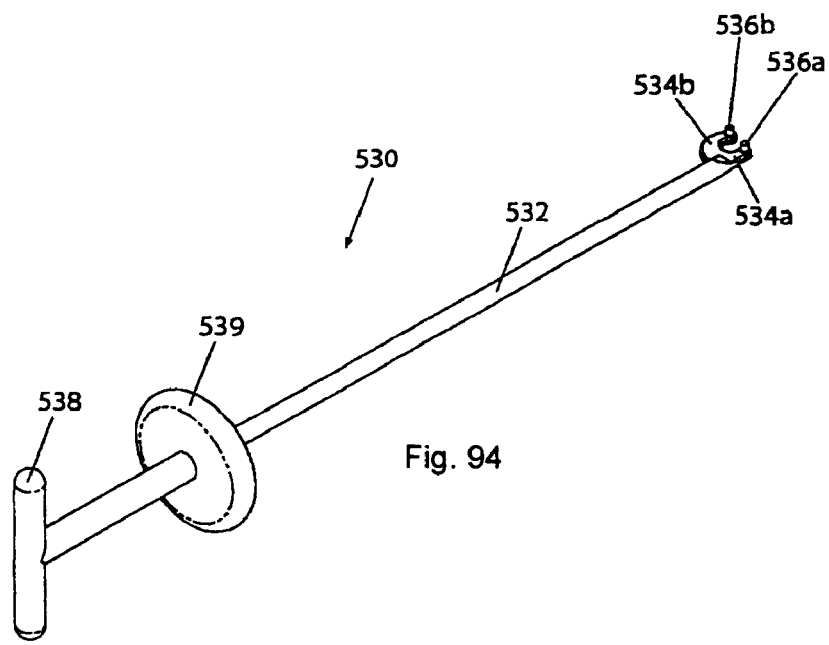
Figure 95:
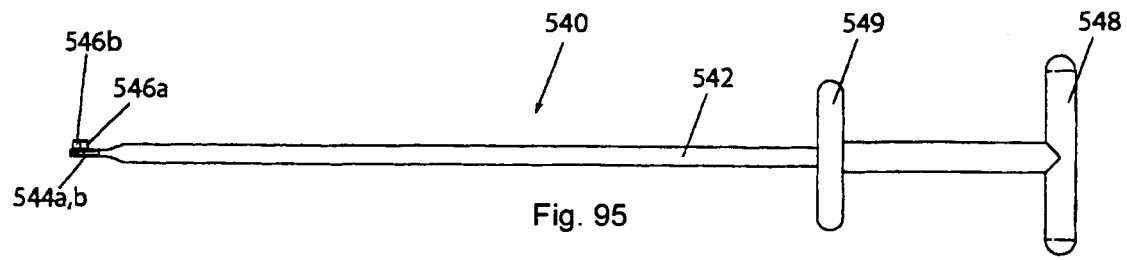
FIGS. 95-97 show side (FIG. 95), top (FIG. 96), and perspective (FIG. 97) views of an alternative offset right repositioner/extractor of the present invention.
Figure 96:
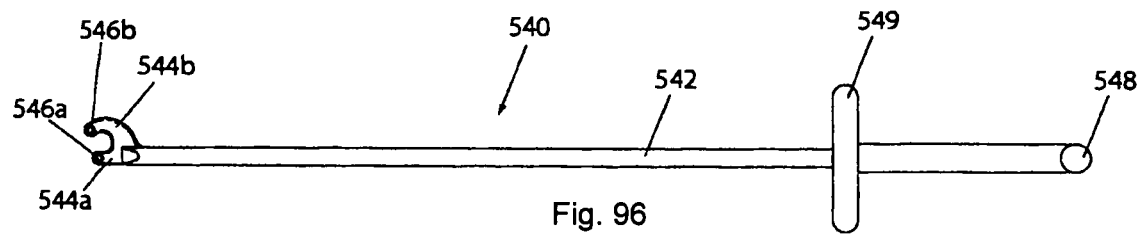
Figure 97:
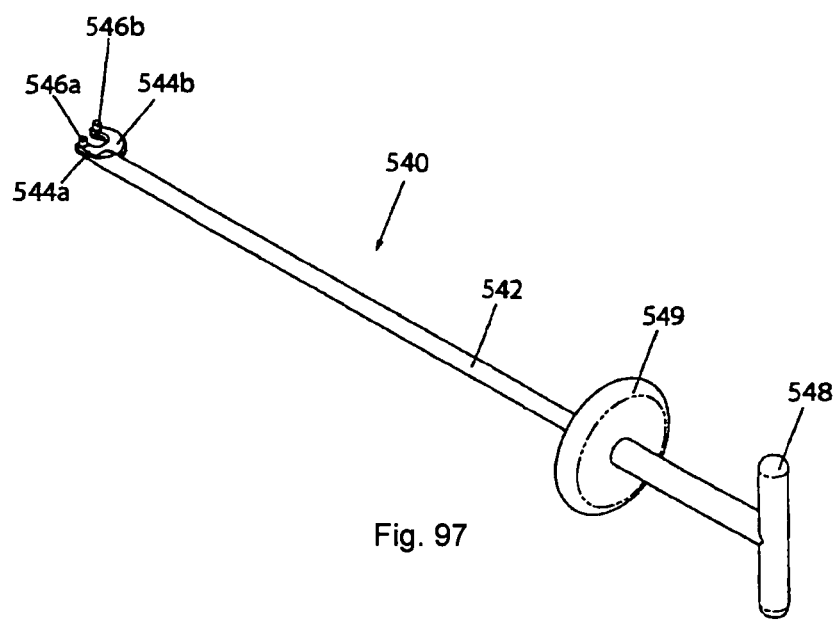

Referring now to FIGS. 83-85, a symmetric repositioner/extractor of the present invention is shown in side (FIG. 83), top (FIG. 84), and perspective (FIG. 85) views. And referring now to FIGS. 86-88, an offset left repositioner/extractor of the present invention is shown in side (FIG. 86), top (FIG. 87), and perspective (FIG. 88) views. And referring now to FIGS. 89-91, an offset right repositioner/extractor of the present invention is shown in side (FIG. 89), top (FIG. 90), and perspective (FIG. 91) views. And referring now to FIGS. 92-94, an alternative offset left repositioner/extractor of the present invention is shown in side (FIG. 92), top (FIG. 93), and perspective (FIG. 94) views. And referring now to FIGS. 95-97, an alternative offset right repositioner/extractor of the present invention is shown in side (FIG. 95), top (FIG. 96), and perspective (FIG. 97) views.

Each repositioner/extractor is provided primarily for repositioning and/or extracting a static trial or artificial intervertebral disc having features suitable for being manipulated by the repositioner/extractor. Exemplary suitable artificial intervertebral discs are described in the '160 and '528 applications with regard to FIGS. 8a-z, 9a-u, 10a-u, 11a-k, and 12a-p thereof and by the accompanying descriptions therefor (e.g., embodiments identified as the first, second, third, fourth, and fifth preferred embodiments of the fourth embodiment family, etc.). Regarding the features suitable for being manipulated by each repositioner/extractor, such features include at least two holes extending longitudinally into one of the baseplates of the static trial or artificial intervertebral disc from the inwardly facing surface of the baseplate. More than two holes can be used to provide for multiple repositioning/extracting approaches. Preferably, in order for the same repositioning/extracting tool to be used for multiple approaches on the same trial or artificial intervertebral disc, adjacent holes should be separated by the same distance separating other adjacent holes.

In order to engage the two holes, each repositioner/extractor has two pins extending in parallel from a central shaft, perpendicular to the longitudinal axis of the central shaft. The pins are spaced to engage the two holes simultaneously, and each pin has a diameter smaller than the diameter of the hole it is to engage. Therefore, the pins can be inserted into the holes, and pulling or pushing on the central shaft along its longitudinal axis when the holes are engaged pulls or pushes the static trial or artificial intervertebral disc in the intervertebral space. Further, because two holes are engaged, the static trial or artificial intervertebral disc can be rotated in either direction about a longitudinal axis passing through the intervertebral space, by rotating of the central shaft of the repositioner/extractor about its distal end, about an axis parallel to the longitudinal axes of the pins. A handle at a proximal end of the central shaft is useful for pushing or pulling on the shaft. A flange adjacent the proximal end of the shaft is useful for impaction (either with a distally directed force or a proximally directed force), if necessary to manipulate the shaft.

On each repositioner/extractor, the pins are formed on prongs that extend laterally from the central shaft. The direction of the prongs, and the location of the pins relative to the central shaft, determine the angle or angles of surgical approach for which a particular repositioner/extractor can be used. Further, the number and location of holes further determine the angle or angles of surgical approach for which a particular repositioner/extractor can be used. Accordingly, the present invention contemplates a variety of repositioner/extractors, and a variety of holes configurations, to provide the surgeon with a variety of possible surgical approach angles.

For example, three repositioner/extractors are illustrated, and, for example, two hole configurations are illustrated.

The first, symmetric, repositioner/extractor 500, shown in FIGS. 83-85, includes a shaft 502 having a distal end that is symmetrically divided into two prongs 504a-b, each of the prongs having a pin 506a-b extending upwardly and parallel to the pin on the other prong. The second and third, left offset and right offset, repositioners/extractors 510,520, shown in FIGS. 86-88 and 89-91, respectively, each include a shaft 512,522 having a distal end that bends diagonally laterally, the left offset distal end 514 bending in one direction (e.g., to the left), the right offset distal end 524 bending in an opposite direction (e.g., to the right). The distal end of each of the second and third repositioners/extractors 510,520 has two pins 516a-b,526a-b serially spaced on the bent portion, and each of the pins extends upwardly and parallel to the other pin. (As shown in FIGS. 92-94 and 95-97, alternative embodiments 530,540 of the second and third, left offset and right offset, repositioners/extractors each include a shaft 532,542 having a distal end that has a straight prong 534a,544a and a curved lateral prong 534b,544b, where the curved lateral prong 534b extends in one direction (e.g., left) for the alternative left offset repositioner/extractor 530, and where the curved lateral prong 544b extends in an opposite direction (e.g., right) for the alternative right offset repositioner/extractor 540. Each of the prongs 534a-b,544a-b has a pin 536a-b,546a-b extending upwardly and parallel to the pin on the other prong. The alternative repositioners/extractors 530,540, each having a space between the pins 536a,b,546a,b, provides for avoidance of any structures on the static trial or artificial intervertebral disc that may be present between the holes.) On each of the repositioners/extractors 500,510,520,530,540, the pins are spaced so that they simultaneously each fit into a respective one of the two adjacent holes in the baseplate of the static trial or artificial intervertebral disc. Each of the repositioners/extractors 500,510,520,530,540 has a handle 508,518,528,538,548 at a proximal end of the central shaft which is useful for pushing or pulling on the shaft, and a flange 509,519,529,539,549 adjacent the proximal end of the shaft that is useful for impaction (either with a distally directed force or a proximally directed force), if necessary to manipulate the shaft.

As noted above, the repositioner/extractor that is appropriate or desired for a given case depends at least in part on the configuration of the holes in the baseplates. Two hole configurations are disclosed, as examples of suitable configurations, although other configurations are possible and contemplated by the present invention. A first hole configuration includes three holes on one of the baseplates, the holes being configured so that a first hole is located in the anterior-posterior plane, and the adjacent (second and third) holes are located in respective opposing anteriolateral planes on either side of the first hole. This hole configuration is shown in FIGS. 98-103, each of which shows a top cutaway view of the artificial intervertebral disc of FIGS. 13-20, showing its lower baseplate, having the first hole configuration, engaged by one of the repositioners/extractors 500, 510,520. Each view of the lower baseplate shows the first hole 550, the second hole 552, and the third hole 554 of the first hole configuration.

A second hole configuration includes four holes on one of the baseplates, the holes being configured so that first and second holes straddle the anterior-posterior plane, a third hole is located so that the third hole and the first hole straddle one of the opposing anteriolateral planes, and a fourth hole is located so that the fourth hole and the second hole straddle the other of the opposing anteriolateral planes. This hole configuration is shown in FIGS. 104-112, each of which shows a bottom cutaway view of the artificial intervertebral disc of FIGS. 13-20, showing its upper baseplate, having the second hole configuration, engaged by one of the repositioners/extractors 500,510,520. Each view of the upper baseplate shows the first hole 560, the second hole 562, the third hole 564, and the fourth hole 566, of the second hole configuration.

It should be understood that configurations having more or fewer holes, and in a variety of locations, are contemplated by the invention, and the detailed descriptions of only two hole configurations is not meant to limit the invention to only these two configurations. Importantly, the invention encompasses using a hole or any number of holes, bored at any suitable angle, whether parallel to other holes or not, in any number of locations on a spacer, a trial or an artificial intervertebral disc (not limited to locations on the baseplates), for purposes of enabling the spacer, trial, or disc to be engaged by a manipulation instrument (not limited to a repositioner/extractor) that engages the hole, and/or to enable the surgeon to work from a variety of approaches. For example, as described in more detail below, the first and second hole configurations described herein, in cooperation with the repositioner/extractors, provide the surgeon with the ability to work from a directly anterior approach, as well as several anteriolateral approaches. It should be understood that additional hole configurations can enable the surgeon to work from a directly posterior approach, posteriolateral approaches, directly lateral approaches, or anteriolateral approaches that are different that those illustrated. For example, the placement of one or more suitably spaced holes (or the addition of one or more holes) on the posterior edge, and/or one or both of the lateral edges of one or both of the baseplates, would enable the surgeon to use the repositioner/extractors of the present invention to achieve such approaches.

As noted above, and referring now FIGS. 98-112 it can be seen that each of the repositioner/extractors can be used in more than one manner depending on the tool desired and the approach desired. For example, with reference to FIGS.

Figure 98:
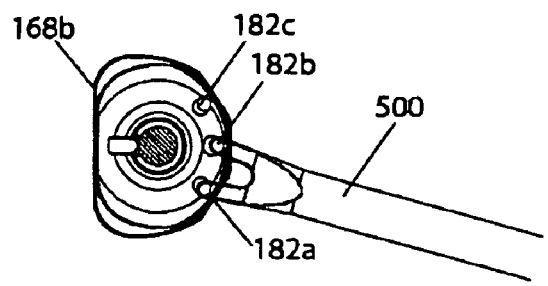
FIGS. 98-103 show exemplary various possible repositioner/extractor approach angles with a three hole configuration of the present invention.
Figure 99:
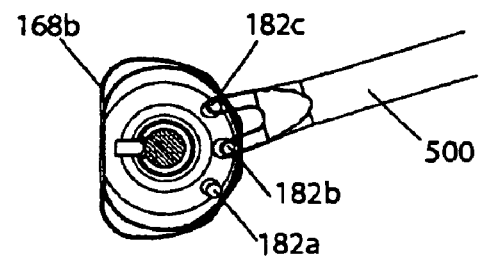

98-99. regarding the first hole configuration (three holes in one of the baseplates), the symmetric repositioner/extractor 500 can be used in -either of two anteriolateral approaches (see FIGS. 98-99). That is, the symmetric repositioner/extractor's shaft 502 can be inserted into the wound from either of the two anteriolateral approaches, and the pins 506a-b can be inserted into the first 550 and second 552 holes (for one of the two anteriolateral approaches) (FIG. 98) or the first 550 and third 552 holes (for the other of the two anteriolateral approaches) (FIG. 99) of the first hole configuration.

Figure 100:
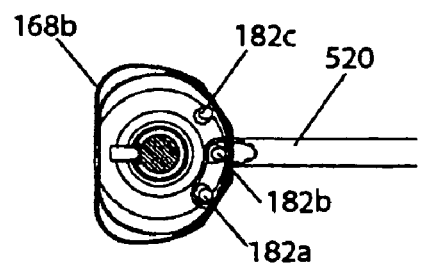
Figure 101:
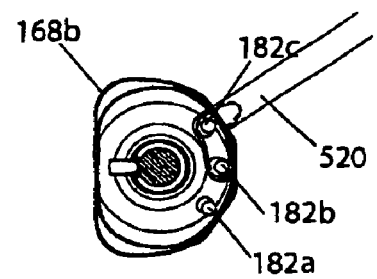
Figure 102:
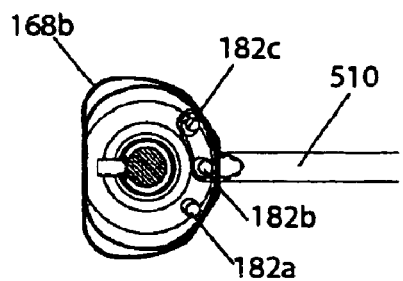
Figure 103:
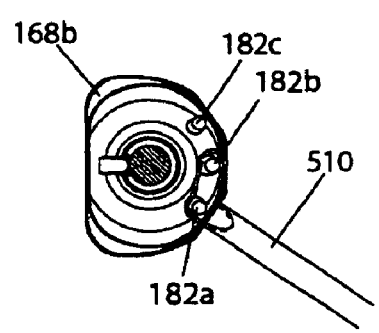

Also, for example, with reference to FIGS. 100-103 regarding the first hole configuration, each of the left offset repositioner/extractor 510 and the right offset repositioner/extractor 520 can be used in either a directly anterior approach (FIGS. 100,102) or a respective anteriolateral approach (FIGS. 101,103). That is, the right offset repositioner/extractor's shaft 522 can be inserted into the wound from a direct anterior approach, and the right offset repositioner/extractor's pins 526a-b can then be placed into the first 550 and second 552 holes of the first hole configuration (FIG. 100). And, the right offset repositioner/extractor's shaft 522 can be inserted into the wound from an anteriolateral approach, and the right offset repositioner/extractor's pins 526a-b can then be placed into the first 550 and third 554 holes of the first hole configuration (FIG. 101). And, the left offset repositioner/extractor's shaft 512 can be inserted into the wound from a direct anterior approach, and the left offset repositioner/extractor's pins 516a-b can then be placed into the first 550 and third 554 holes of the first hole configuration (FIG. 102). And, the left offset repositioner/extractor's shaft 512 can be inserted into the wound from an anteriolateral approach, and the left offset repositioner/extractor's pins 516a-b can then be placed into the first 550 and second 552 holes of the first hole configuration (FIG. 103). It should be noted that the alternate left offset 530 and alternate right offset 540 repositioners/extractors can also fit into the holes of the first hole configuration in the same manner as described here with regard to the left offset 510 and right offset 520 repositioners/extractors.

Figure 104:
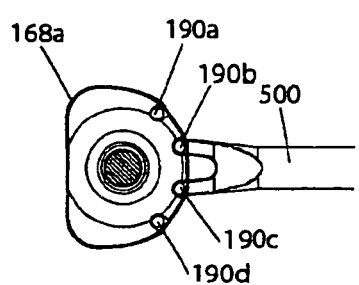
FIGS. 104-112 show exemplary various possible repositioner/extractor approach angles with a four hole configuration of the present invention.
Figure 105:
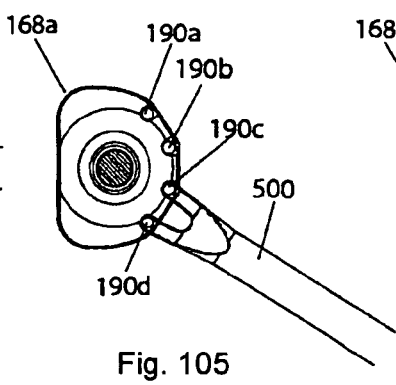
Figure 106:
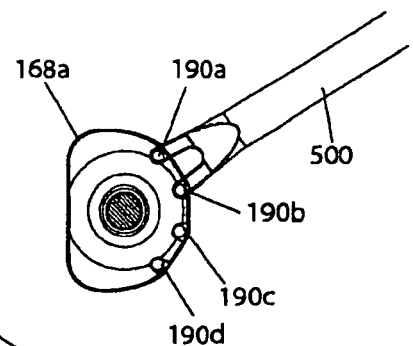
Figure 107:
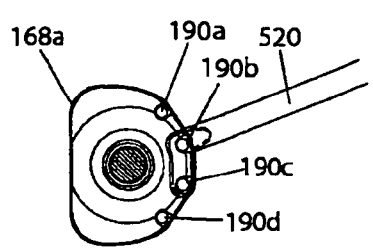
Figure 108:
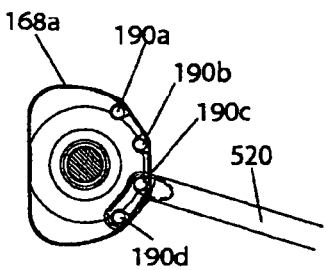
Figure 109:
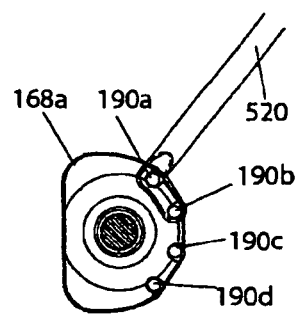
Figure 110:
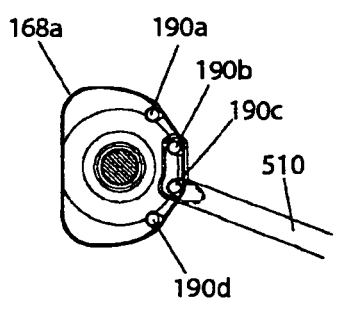
Figure 111:
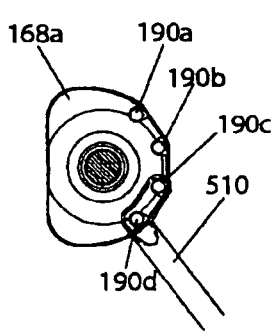
Figure 112:
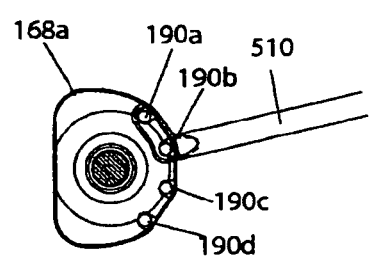
Figure 113:
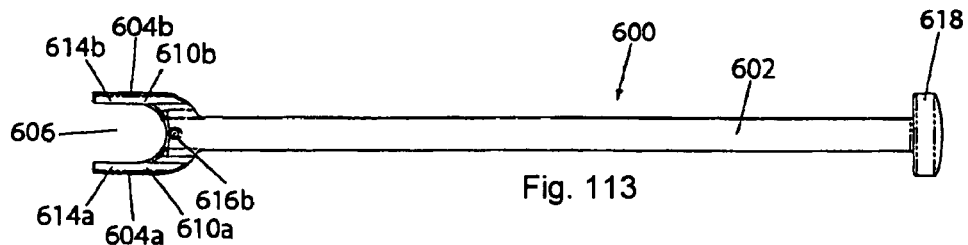
FIGS. 113-117 show bottom (FIG. 113), side (FIG. 114), front (FIG. 115), top partial perspective (FIG. 116), and bottom partial perspective (FIG. 117) views of a leveler of the present invention.
Figure 114:
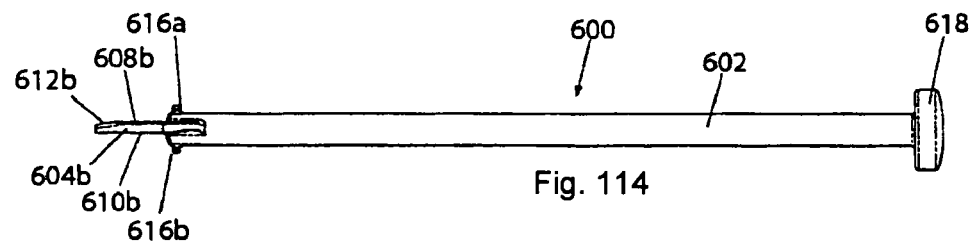
Figure 115:
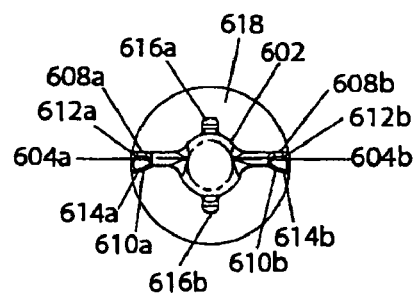

Also, for example, with reference to FIGS. 104-112, regarding the second hole configuration (four holes in one of the baseplates), the symmetric repositioner/extractor 500 can be used in a directly anterior approach (FIG. 104), and either of two anteriolateral approaches (FIGS. 105-106). That is, the symmetric repositioner/extractor's shaft 502 can be inserted into the wound from a directly anterior approach, and the pins 506a-b can be inserted into the first 560 and second 562 holes of the second hole configuration (FIG. 104). And, the symmetric repositioner/extractor's shaft 502 can be inserted into the wound from either of the two anteriolateral approaches, and the pins 506a-b can be inserted into the first 560 and third 564 holes (for one of the two anteriolateral approaches) (FIG. 105) or the second 562 and fourth 566 holes (for the other of the two anteriolateral approaches) (FIG. 106) of the second hole configuration.

Also, for example, with reference to FIGS. 107-112, regarding the second hole configuration, each of the left offset repositioner/extractor 510 and the right offset repositioner/extractor 520 can be used in any of three respective anteriolateral approaches. That is, the right offset repositioner/extractor's shaft 522 can be inserted into the wound from any of its three possible anteriolateral approaches, and the right offset repositioner/extractor's pins 526a-b can then be placed into the first 560 and second 562 holes (FIG. 107) (for a first of the three anteriolateral approaches), the first 560 and third 564 holes (FIG. 108) (for a second of the three anteriolateral approaches), or the second 562 and fourth 566 holes (FIG. 109) (for a third of the three anteriolateral approaches). And, the left offset repositioner/extractor's shaft 512 can be inserted into the wound from any of its three possible anteriolateral approaches, and the left offset repositioner/extractor's pins 516a-b can then be placed into the first 560 and second 562 holes (FIG. 110) (for a first of the three anteriolateral approaches), the first 560 and third 564 holes (FIG. 111) (for a second of the three anteriolateral approaches), or the second 562 and fourth 566 holes (FIG. 112) (for a third of the three anteriolateral approaches). It should be noted that the alternate left offset 530 and alternate right offset 540 repositioners/extractors can also fit into the holes of the second hole configuration in the same manner as described here with regard to the left offset 510 and right offset 520 repositioners/extractors.

It should be noted from the illustrations in FIGS. 98-112 that the anteriolateral approaches are at a variety of angles relative to the anterior-posterior plane, and further that the illustrated angles are merely exemplary. That is, the invention encompasses additional approach angles, in that such additional approach angles are possible by (as described above) adding or deleting holes, and/or changing the location of holes, and/or changing the spacing between holes (in conjunction with changing the spacing between pins), and/or changing the angle at which the offset repositioner/extractors' pins are placed relative to one another and to the shaft of such repositioner/extractors.

As discussed above, once the pins are established in the two adjenct holes, manipulating the shaft of the repositioner/extractor will repositon the static trial or artificial intervertebral disc in the intervertebral space and/or extract it from the intervertebral space. The use of more than one pin (versus one pin) enables the static trial or artificial intervertebral disc to be rotated ineither direction about a longtitudinal axis passing through the intervertebral space.

A preferred embodiment of a leveler of the present invention will now be described.

Figure 116:
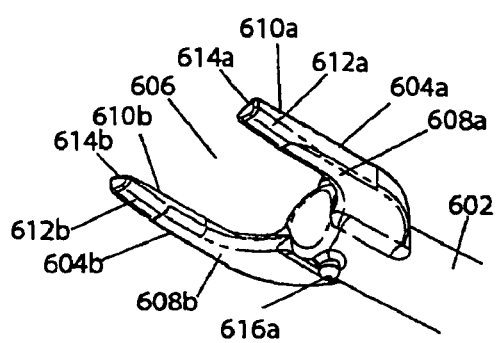
Figure 117:
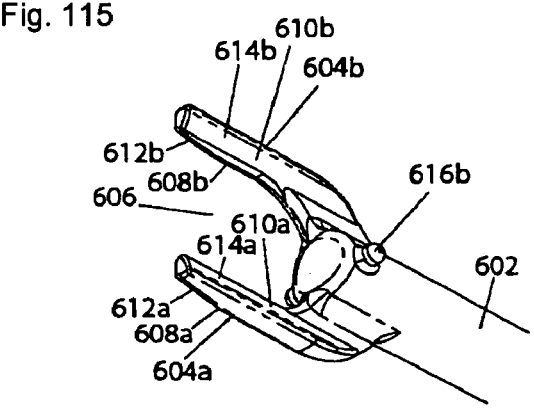

Referring now to FIGS. 113-117, a leveler of the present invention is shown in bottom (FIG. 113), side (FIG. 114), front (FIG. 115), top partial perspective (FIG. 116), and bottom partial perspective (FIG. 117) views. More particularly, FIG. 116 shows a top perspective view of the distal end of the leveler, and FIG. 117 shows a bottom perspective view of the distal end of the leveler.

The leveler is provided primarily for establishing a parallel orientation of the baseplates (relative to one another), and/or securing the purchase of the stabilizing spikes, of an artificial intervertebral disc having features suitable for being manipulated by the leveler. Exemplary suitable artificial intervertebral discs are described in the '160 and '528 applications with regard to FIGS. 8a-z, 9a-u, 10a-u, 11a-k, and 12a-p thereof and by the accompanying descriptions therefor (e.g., embodiments identifies as the first, second, third, fourth, and fifth preferred embodiments of the fourth embodiment family, etc.) Regarding the features suitable for being manipulated by the leveler, such features include suitably formed inwardly facing surfaces of the baseplates of the artificial intervertebral disc.

More particularly, the leveler 600 includes a shaft 602 having a forked distal end formed by two opposing tongs 604a-b that are symmetric to one another about a longitudinal axis of the shaft 602. Each of the tongs 604a-b has an extent that intially curves laterally outward away from the shaft 602 and from the other tong's extent, to define a central pocket 606 forward of the shaft 602 between the tongs' extents. Each tong's extent then resumes a distal direction to become parallel to the shaft 602 and to the other tong's extent.

Each tong's extent has an upper surface 608a-b and a lower surface 610a-b. The upper surface 608a-b is preferably shaped to conform against the inwardly facing surface of a first (e.g., upper) baseplate of an artificial intervertebral disc, and the lower surface 610a-b is preferably shaped to conform against the inwardly facing surface of a second (e.g., lower) baseplate of the artificial intervertebral disc, so that insertion of the forked distal end of the leveler 600 between the baseplates, with the central pocket 606 of the distal end avoiding the central portion of the artificial intervertebral disc, and with the upper 608a-b and lower surfaces 610a-b so engaging the inwardly facing surfaces of the baseplates, causes the baseplates to be placed in parallel orientation with respect to one another.

More particularly, for example for use with the exemplary artificial intervertebral disc of FIGS. 13-20, the upper surface 608a-b of each extent is flat, except for a tapered section 612a-b at the distal tip of the extent, which tapered section narrows the tip, and the lower surface 610a-b of each extent is curved to form opposing concave contours 614a-b that are cooperatingly shaped to conform against the inwardly facing surface of the convex structure of the artificial intervertebral disc.

The preferred use of the leveler 600 is as follows. As discussed above, once the intervertebral space has been prepared and distracted to a dimension that will accept the artificial intervertebral disc to be implanted, the artificial intervertebral disc 160 is engaged at its lower baseplate 168b by the inserter/impactor 400,4000 discussed above. During insertion (and, if necessary, impaction) of the artificial intervertebral disc 160 into the intervertebral space, the upper baseplate 168a remains free to angulate with respect to the lower baseplate 168b, so that the angulation of the baseplates conforms to the angulation of the intervertebral space as the artificial intervertebral disc is being inserted thereinto. Typically, the endplates of the prepared and distracted intervertebral space will be lordotically angled with respect to one another, due to the use of the static trials 100,1000 as described above, which are formed to have a lordotic taper as discussed above. Thus, when the artificial intervertebral disc is inserted into the intervertebral space, its baseplates will be lordotically angled with respect to one another. Once the artificial intervertebral disc 160 is inserted, the inserter/impactor 400,4000 can be disengaged, and the repositioner/extractors 500,510,520,530,540 discussed above can be applied to the artificial intervertebral disc, if necessary to achieve a more optimal positioning.

Once the positioning is established, the leveler 600 is preferably applied to the artificial intervertebral disc 160. The forked distal end of the leveler 600 is inserted so that the extents 604a-b are placed between the inwardly facing surface 164a of the upper baseplate 168a and the inwardly facing surface 164b of the convex structure 162 on the lower baseplate 168b, and so that the central pocket 606 of the leveler 600 avoids the ball-and-socket joint of the artificial intervertebral disc 160. If the baseplates are lordotically angled with respect to one another, the tapered sections 612a-b of the upper surfaces 608a-b of the forked distal end will be approximately parallel to, and will first encounter, the angled inwardly facing surface 164a of the upper baseplate 168a. At the same time, the concave contours 614a-b of the lower surfaces 610a-b will accommodate the inwardly facing surface 164b of the convex structure 162 on the lower baseplate 168b. As the, tapered sections 612a-b press against the inwardly facing surface 164a of the upper baseplate 168a, and the concave contours 614a-b slip into place against the inwardly facing surface 164b of the convex structure 162 on the lower baseplate 168b, the tapers 612a-b will function as wedges to force the posterior portion of the upper baseplate 168a away from the posterior portion of the lower baseplate 168b. Accordingly, as the posterior portions are being separated, the stabilizing spikes 188a-b on the outwardly facing surfaces 186a-b of the baseplates 168a-b find or secure their purchase in the hard bone of the outer ring of the vertebral body endplates. When the forked distal end is fully seated (stops 616a-b are provided to butt up against the anterior portions of the baseplates 168a-b to prevent the forked distal end from being inserted too far), the extents of the tongs 604a-b hold the baseplates 168a-b parallel to one another, and so that the spikes 188a-b are fully engaged in the endplates. The surgeon then slips the leveler 600 out from between the baseplates 168a-b, and out from the wound and completes the procedure. A handle 618 is provided at a proximal end of the shaft 602 for pushing, pulling, and otherwise manipulating the leveler 600 as needed.

While there has been described and illustrated specific embodiments of instrumentation, it will be apparent to those skilled in the art that variations and modifications are possible without deviating from the broad spirit and principle of the invention. The invention, therefore, shall not be limited to the specific embodiments discussed herein.

What is claimed is:

1. A spinal orthopedic device and tool set, comprising an intervertebral spacer device having first and second baseplates mounted to one another such that the first and second baseplates are articulatable relative to one another, wherein at least one of the baseplates has at least one pair of engagement holes, each hole of the at least one pair being separated from the other hole of the at least one pair by a space having a length; and a manipulation tool having a handle, a proximal end and a distal end, the handle extending along a first longitudinal axis, the manipulation tool further including a first engagement post and a second engagement post, each engagement post positioned proximate the distal end of the manipulation tool, the first engagement post extending along a second longitudinal axis and the second engagement post extending along a third longitudinal axis, the first longitudinal axis being substantially perpendicular to the second and third longitudinal axes, the first engagement post being separated from the second engagement post by a second space having a length, said length of said second space being equivalent to said length of said space between the pair of engagement holes of the intervertebral spacer such that the first and second engagement posts are positionable in the at least one pair of engagement holes, said first and second engagement posts defining a pair of engagement posts.

2. The spinal orthopedic device and tool set of claim 1, wherein the at least one of the baseplates has at least two pairs of engagement holes; and wherein the pair of engagement posts is positionable in any pair of the at least two pairs of engagement holes.

3. The spinal orthopedic device and tool set of claim 2, wherein the at least two pairs of engagement holes comprise three engagement holes, a first of the three engagement holes being separated from a second of the three engagement holes by a space having the length, the second of the three engagement holes being separated from a third of the three engagement holes by a space having the length.

4. The spinal orthopedic device and tool set of claim 2, wherein the at least two pairs of engagement holes comprises three pairs of engagement holes, the three pairs of engagement holes comprising four engagement holes, a first of the four engagement holes being separated from a second of the four engagement holes by a space having the length, the second of the four engagement holes being separated from a third of the four engagement holes by a space having the length, the third of the four engagement holes being separated from a fourth of the four engagement holes by a space having the length.

5. The spinal orthopedic device and tool set of claim 1, wherein each baseplate has an inwardly facing surface and an outwardly facing surface; and wherein the baseplates are mounted to one another such that the inwardly facing surfaces face one another and the outwardly facing surfaces face away from one another; and wherein one of the inwardly facing surfaces has at least one pair of the at least one pair of engagement holes.

6. The spinal orthopedic device and tool set of claim 5, wherein the inwardly facing surface of the first baseplate has the at least one pair of the at least one pair of engagement holes, and wherein the inwardly facing surface of the second baseplate has at least one other pair of the at least one pair of engagement holes.

7. The spinal orthopedic device and tool set of claim 6, wherein the inwardly facing surface of the first baseplate has three pairs of engagement holes, and the inwardly facing surface of the second baseplate has two pairs of engagement holes; and wherein the pair of engagement posts is positionable in any of the pairs of engagement holes.

8. The spinal orthopedic device and tool set of claim 7, wherein the three pairs of engagement holes comprise four engagement holes, a first of the four engagement holes being separated from a second of the four engagement holes by a space having the length, the first of the four engagement holes being separated from a third of the four engagement holes by a space having the length, the second of the four engagement holes being separated from a fourth of the four engagement holes by a space having the length.

9. The spinal orthopedic device and tool set of claim 8, wherein the two pairs of engagement holes comprise three engagement holes, a first of the three engagement holes being separated from a second of the three engagement holes by a space having the length, the first of the three engagement holes being separated from a third of the three engagement holes by a space having the length.

10. The spinal orthopedic device and tool set of claim 9, wherein the first and second engagement holes of the four engagement holes are evenly distributed about an anterior aspect of the inwardly facing surface of the first baseplate, the first and third engagement holes of the four engagement holes are evenly distributed about a left antero-lateral aspect of the inwardly facing surface of the first baseplate, and the second and fourth engagement holes of the four engagement holes are evenly distributed about a right antero-lateral aspect of the inwardly facing surface of the first baseplate; and wherein the first engagement hole of the three engagement holes is centered at an anterior aspect of the inwardly facing surface of the second baseplate, the second engagement hole of the three engagement holes is centered at a left antero-lateral aspect of the inwardly facing surface of the second baseplate, and the third engagement hole of the three engagement holes is centered at a right antero-lateral aspect of the inwardly facing surface of the second baseplate.

11. The spinal orthopedic device and tool set of claim 10, wherein the anterior aspect of the inwardly facing surface of the first baseplate and the anterior aspect of the inwardly facing surface of the second baseplates are co-planar; and wherein the left antero-lateral aspect of the inwardly facing surface of the first baseplate and the left antero-lateral aspect of the inwardly facing surface of the second baseplates are co-planar; and wherein the right antero-lateral aspect of the inwardly facing surface of the first baseplate and the right antero-lateral aspect of the inwardly facing surface of the second baseplates are co-planar.

12. The spinal orthopedic device and tool set of claim 1, wherein the at least one pair of engagement holes comprises at least one engagement hole centered at a first desired surgical approach aspect of the at least one of the baseplates, and at least one engagement hole centered at a second desired surgical approach aspect of the at least one of the baseplates.

13. The spinal orthopedic device and tool set of claim 12, wherein the first desired surgical approach aspect is an anterior, aspect of the at least one of the baseplates, and the second desired surgical approach aspect is an antero-lateral aspect of the at least one of the baseplates.

14. The spinal orthopedic device and tool set of claim 12, wherein the at least one pair of engagement holes comprises two pairs of engagement holes, and the two pairs of engagement holes comprise three engagement holes, a first of the three engagement holes being separated from a second of the three engagement holes by a space having the length, the second of the three engagement holes being separated from a third of the three engagement holes by a space having the length; and wherein the second engagement hole of the three engagement holes is centered at the second desired surgical approach aspect of the at least one of the baseplates, and wherein the first engagement hole of the three engagement holes is positioned at the first desired surgical approach aspect of the at least one of the baseplates, and wherein the third engagement hole of the three engagement holes is positioned at a third desired surgical approach aspect of the at least one of the baseplates.

15. The spinal orthopedic device and tool set of claim 14, wherein the first desired surgical approach aspect is an anterior aspect of the at least one of the baseplates, the second desired surgical approach aspect is left antero-lateral aspect of the at least one of the baseplates, and the third desired surgical approach aspect is a right antero-lateral aspect of the at least one of the baseplates.

16. The spinal orthopedic device and tool set of claim 1, wherein the at least one pair of engagement holes comprises first and second engagement holes evenly distributed about a desired surgical approach aspect of the at least one of the baseplates.

17. The spinal orthopedic device and tool set of claim 16, wherein the desired surgical approach aspect is an anterior aspect of the at least one of the baseplates.

18. The spinal orthopedic device and tool set of claim 17, wherein the desired surgical approach aspect is a first desired surgical approach aspect; and wherein the at least one pair of engagement holes comprises at least three pairs of engagement holes, and the at least three pairs of engagement holes comprise four engagement holes, the four engagement holes comprising the first and second engagement holes distributed about the first desired surgical approach aspect of the at least one of the baseplates, the four engagement holes further comprising a third engagement hole positioned such that the first engagement hole and the third engagement hole are evenly distributed about a second desired surgical approach aspect of the at least one of the baseplates, the four engagement holes further comprising a fourth engagement hole positioned such that the second engagement hole and the fourth engagement hole are evenly distributed about a third desired surgical approach aspect of the at least one of the baseplates.

19. The spinal orthopedic device and tool set of claim 18, wherein the first desired surgical approach aspect is an anterior aspect of the at least one of the baseplates, the second desired surgical approach aspect is left antero-lateral aspect of the at least one of the baseplates, and the third desired surgical approach aspect is a right antero-lateral aspect of the at least one of the baseplates.

20. The spinal orthopedic device and tool set of claim 18, wherein the first of the four engagement holes is separated from the second of the four engagement holes by a space having the length, the first of the four engagement holes is separated from the third of the four engagement holes by a space having the length, and the second of the four engagement holes is separated from the fourth of the four engagement holes by a space having the length.

* * * * *

UNITED STATES PATENT AND TRADEMARK OFFICE
CERTIFICATE OF CORRECTION

PATENT NO. : 7,223,291 B2
APPLICATION NO. : 10/663492
DATED : May 29, 2007
INVENTOR(S) : Joseph P. Errico, Michael W. Dudasik and Rafail Zubok It is certified that error appears in the above-identified patent and that said Letters Patent is hereby corrected as shown below:

Column 28, line 57, delete the comma "," after the word "corners".
Column 41, line 47, insert a close parenthesis --)-- after the word "upper".
Column 41, line 47, delete the word "parallet" and insert the word --parallel--.
Column 49, line 67, delete the comma "," after the word "the".
Column 52, line 19, delete the comma "," after the word "anterior".

Signed and Sealed this

Twenty-sixth Day of August, 2008

JON W. DUDAS
*Director of the United States Patent and Trademark Office*